(12) United States Patent
Mayberry et al.

(10) Patent No.: US 8,764,812 B2
(45) Date of Patent: Jul. 1, 2014

(54) BIFURCATED GRAFT DEPLOYMENT SYSTEMS AND METHODS

(71) Applicant: Endologix, Inc., Irvine, CA (US)

(72) Inventors: Kevin Mayberry, Mission Viejo, CA (US); Trinh Pham, Westminster, CA (US); Stefan G. Schreck, Fallbrook, CA (US)

(73) Assignee: Endologix, Inc., Irvine, CA (US)

( * ) Notice: Subject to any disclaimer, the term of this patent is extended or adjusted under 35 U.S.C. 154(b) by 0 days.

(21) Appl. No.: 13/745,682

(22) Filed: Jan. 18, 2013

(65) Prior Publication Data

US 2013/0138200 A1 May 30, 2013

Related U.S. Application Data

(60) Division of application No. 13/046,541, filed on Mar. 11, 2011, now Pat. No. 8,357,192, which is a continuation of application No. 12/101,863, filed on Apr. 11, 2008, now Pat. No. 8,236,040.

(51) Int. Cl.
*A61F 2/06* (2013.01)

(52) U.S. Cl.
USPC ......................................... 623/1.11

(58) Field of Classification Search
USPC .......... 604/528; 600/585; 623/1.1, 1.13, 1.15, 623/1.16, 1.17, 1.18, 1.19, 1.2, 1.22, 1.23, 623/1.28, 1.29, 1.3, 1.31, 1.35; 606/108
See application file for complete search history.

(56) References Cited

U.S. PATENT DOCUMENTS

| | | | |
|---|---|---|---|
| 519,928 A | 5/1894 | Schanck | |
| 1,065,935 A | 7/1913 | Gail | |
| 2,127,903 A | 8/1938 | Bowen | |
| 2,335,333 A | 11/1943 | Wysong | |
| 2,437,542 A | 5/1944 | Krippendorf | |
| 2,845,959 A | 8/1958 | Sidebotham | |
| 2,990,605 A | 7/1961 | Demsyk | |
| 3,029,819 A | 4/1962 | Starks | |
| 3,096,560 A | 7/1963 | Liebig | |
| 3,805,301 A | 4/1974 | Liebig | |

(Continued)

FOREIGN PATENT DOCUMENTS

| | | |
|---|---|---|
| CA | 2007648 | 4/1991 |
| CA | 2127458 A1 | 7/1993 |

(Continued)

OTHER PUBLICATIONS

US 5,690,647, 11/1997, Osborne. (withdrawn).
US 6,413,270, 7/2002, Thornton et al. (withdrawn).
U.S. Appl. No. 10/690,227, filed Oct. 21, 2003, Shaolian et al.
U.S. Appl. No. 12/390,346, filed Feb. 20, 2009, Schreck et al.
U.S. Appl. No. 12/496,446, filed Jul. 1, 2009, Benjamin, et al.
U.S. Appl. No. 09/714,854, filed Nov. 15, 2000, Shaolian et al.
U.S. Appl. No. 12/769,506, filed Apr. 28, 2010, Mayberry, et al.

(Continued)

*Primary Examiner* — Ryan Severson
*Assistant Examiner* — Jonathan W Miles
(74) *Attorney, Agent, or Firm* — Knobbe Martens Olson & Bear LLP

(57) ABSTRACT

A method for deploying an endoluminal vascular prosthesis using a deployment catheter that has at least a main graft portion and a first branch graft portion. The deployment catheter preferably comprises an elongate, flexible catheter body having a proximal end and a distal end, and an outer sheath and an inner core that is axially moveable with respect to the outer sheath. The catheter preferably comprises a main graft restraint that has a main graft release mechanism comprising a main graft sheath and a suture threaded through a plurality of the openings in the main graft sheath. The catheter further comprises at least one branch graft restraint comprising at least one branch graft release mechanism.

22 Claims, 21 Drawing Sheets

(56) References Cited

U.S. PATENT DOCUMENTS

| | | |
|---|---|---|
| 3,994,149 A | 11/1976 | Dahlman |
| 4,362,156 A | 12/1982 | Feller, Jr. et al. |
| 4,473,067 A | 9/1984 | Schiff |
| 4,497,074 A | 2/1985 | Rey et al. |
| 4,501,263 A | 2/1985 | Harbuck |
| 4,503,568 A | 3/1985 | Madras |
| 4,525,157 A | 6/1985 | Vaillancourt |
| 4,562,596 A | 1/1986 | Kornberg |
| 4,580,568 A | 4/1986 | Gianturco |
| 4,592,754 A | 6/1986 | Gupte et al. |
| 4,617,932 A | 10/1986 | Kornberg |
| 4,756,307 A | 7/1988 | Crownshield |
| 4,800,882 A | 1/1989 | Gianturco |
| 4,816,028 A | 3/1989 | Kapadia et al. |
| 4,840,940 A | 6/1989 | Sottiurai |
| 4,856,516 A | 8/1989 | Hillstead |
| 4,878,906 A | 11/1989 | Lindemann et al. |
| 4,907,336 A | 3/1990 | Gianturco |
| 4,922,905 A | 5/1990 | Strecker |
| 4,981,478 A | 1/1991 | Evard et al. |
| 4,981,947 A | 1/1991 | Tomagou et al. |
| 4,994,069 A | 2/1991 | Ritchrt et al. |
| 4,994,071 A | 2/1991 | MacGregor |
| 5,019,090 A | 5/1991 | Pinchuk |
| 5,026,377 A | 6/1991 | Burton et al. |
| 5,035,706 A | 7/1991 | Giantureo et al. |
| 5,064,435 A | 11/1991 | Porter |
| 5,078,726 A | 1/1992 | Kreamer |
| 5,104,399 A | 4/1992 | Lazarus |
| 5,108,424 A | 4/1992 | Hoffman, Jr. et al. |
| 5,116,349 A | 5/1992 | Aranyi |
| 5,123,917 A | 6/1992 | Lee |
| 5,133,732 A | 7/1992 | Wiktor |
| 5,135,535 A | 8/1992 | Kramer |
| 5,135,536 A | 8/1992 | Hillstead |
| 5,156,619 A | 10/1992 | Ehrenfeld |
| 5,158,545 A | 10/1992 | Trudell et al. |
| 5,178,634 A | 1/1993 | Martinez |
| 5,195,978 A | 3/1993 | Schiffer |
| 5,197,976 A | 3/1993 | Herweck et al. |
| 5,201,757 A | 4/1993 | Heyn et al. |
| 5,211,658 A | 5/1993 | Clouse |
| 5,246,452 A | 9/1993 | Sinnott |
| 5,256,141 A | 10/1993 | Gencheff et al. |
| 5,263,932 A | 11/1993 | Jang |
| 5,275,622 A | 1/1994 | Lazarus et al. |
| 5,282,824 A | 2/1994 | Gianturco |
| 5,282,860 A | 2/1994 | Matsuno et al. |
| 5,304,200 A | 4/1994 | Spaulding |
| 5,314,444 A | 5/1994 | Gianturco |
| 5,314,472 A | 5/1994 | Fontaine |
| 5,316,023 A | 5/1994 | Palmaz et al. |
| 5,320,602 A | 6/1994 | Karpiel |
| 5,330,500 A | 7/1994 | Song |
| 5,342,387 A | 8/1994 | Summers |
| 5,354,308 A | 10/1994 | Simon et al. |
| 5,360,443 A | 11/1994 | Barone et al. |
| 5,366,504 A | 11/1994 | Anderson et al. |
| 5,370,683 A | 12/1994 | Fontaine |
| 5,383,892 A | 1/1995 | Cardon et al. |
| 5,387,235 A | 2/1995 | Chuter |
| 5,389,087 A | 2/1995 | Miraki |
| 5,397,355 A | 3/1995 | Marin et al. |
| 5,403,341 A | 4/1995 | Solar |
| 5,405,377 A | 4/1995 | Cragg |
| 5,405,378 A | 4/1995 | Strecker |
| 5,415,664 A | 5/1995 | Pinchuk |
| 5,423,886 A | 6/1995 | Arru et al. |
| 5,425,765 A | 6/1995 | Tiefenbrun et al. |
| 5,443,477 A | 8/1995 | Marin et al. |
| 5,443,498 A | 8/1995 | Fontaine |
| 5,443,500 A | 8/1995 | Sigwart |
| 5,453,090 A | 9/1995 | Martinez et al. |
| 5,456,713 A | 10/1995 | Chuter |
| 5,458,615 A | 10/1995 | Klemm et al. |
| 5,462,530 A | 10/1995 | Jang |
| 5,464,449 A | 11/1995 | Ryan et al. |
| 5,464,450 A | 11/1995 | Buscemi et al. |
| 5,472,417 A | 12/1995 | Martin et al. |
| 5,484,444 A | 1/1996 | Braunschweiler et al. |
| 5,489,295 A | 2/1996 | Piplani et al. |
| 5,496,365 A | 3/1996 | Sgro |
| 5,507,767 A | 4/1996 | Maeda et al. |
| 5,507,768 A | 4/1996 | Lau et al. |
| 5,507,769 A | 4/1996 | Marin et al. |
| 5,507,771 A | 4/1996 | Gianturco |
| 5,522,880 A | 6/1996 | Barone et al. |
| 5,522,881 A | 6/1996 | Lentz |
| 5,522,883 A | 6/1996 | Slater et al. |
| 5,545,211 A | 8/1996 | An et al. |
| 5,549,635 A | 8/1996 | Solar |
| 5,554,118 A | 9/1996 | Jang |
| 5,554,181 A | 9/1996 | Das |
| 5,562,697 A | 10/1996 | Christiansen |
| 5,562,726 A | 10/1996 | Chuter |
| 5,562,728 A | 10/1996 | Lazarus et al. |
| 5,571,169 A | 11/1996 | Plaia et al. |
| 5,571,172 A | 11/1996 | Chin |
| 5,571,173 A | 11/1996 | Parodi |
| 5,575,816 A | 11/1996 | Rudnick et al. |
| 5,575,818 A | 11/1996 | Pinchuk |
| 5,578,071 A | 11/1996 | Parodi |
| 5,578,072 A | 11/1996 | Barone et al. |
| 5,591,197 A | 1/1997 | Orth et al. |
| 5,591,198 A | 1/1997 | Boyle et al. |
| 5,591,226 A | 1/1997 | Trerotola et al. |
| 5,591,228 A | 1/1997 | Edoga |
| 5,591,229 A | 1/1997 | Parodi |
| 5,591,230 A | 1/1997 | Horn et al. |
| 5,593,417 A | 1/1997 | Rhodes |
| 5,599,305 A | 2/1997 | Hermann et al. |
| 5,604,435 A | 2/1997 | Foo et al. |
| 5,607,445 A | 3/1997 | Summers |
| 5,609,625 A | 3/1997 | Piplani et al. |
| 5,609,627 A | 3/1997 | Goicoechea et al. |
| 5,609,628 A | 3/1997 | Kerenen |
| 5,628,783 A | 5/1997 | Quiachonet et al. |
| 5,628,786 A | 5/1997 | Banas et al. |
| 5,628,788 A | 5/1997 | Pinchuk |
| 5,630,829 A | 5/1997 | Lauterjung |
| 5,630,830 A | 5/1997 | Verbeek |
| 5,632,763 A | 5/1997 | Glastra |
| 5,632,772 A | 5/1997 | Alcime et al. |
| 5,639,278 A | 6/1997 | Dereume et al. |
| 5,641,373 A | 6/1997 | Shannon et al. |
| 5,643,171 A | 7/1997 | Bradshaw et al. |
| 5,643,278 A | 7/1997 | Wijay |
| 5,643,339 A | 7/1997 | Kavteladze et al. |
| 5,647,857 A | 7/1997 | Anderson et al. |
| 5,649,952 A | 7/1997 | Lam |
| 5,651,174 A | 7/1997 | Schwartz et al. |
| 5,653,727 A | 8/1997 | Wiktor |
| 5,653,743 A | 8/1997 | Martin |
| 5,653,746 A | 8/1997 | Schmitt |
| 5,653,747 A | 8/1997 | Dereume |
| 5,653,748 A | 8/1997 | Strecker |
| 5,662,580 A | 9/1997 | Bradshaw et al. |
| 5,662,614 A | 9/1997 | Edoga |
| 5,662,700 A | 9/1997 | Lazarus |
| 5,662,701 A | 9/1997 | Plaia et al. |
| 5,662,702 A | 9/1997 | Keranen |
| 5,662,703 A | 9/1997 | Yurek et al. |
| 5,665,115 A | 9/1997 | Cragg |
| 5,665,117 A | 9/1997 | Rhodes |
| 5,669,880 A | 9/1997 | Solar |
| 5,669,924 A | 9/1997 | Shaknovich |
| 5,669,934 A | 9/1997 | Sawyer |
| 5,674,241 A | 10/1997 | Bley et al. |
| 5,674,276 A | 10/1997 | Anderson et al. |
| 5,676,685 A | 10/1997 | Razavi |
| 5,676,696 A | 10/1997 | Marcade |
| 5,676,697 A | 10/1997 | McDonald |
| 5,679,400 A | 10/1997 | Tuch |
| 5,681,345 A | 10/1997 | Euteneuer |

(56) References Cited

U.S. PATENT DOCUMENTS

| | | |
|---|---|---|
| 5,681,346 A | 10/1997 | Orth et al. |
| 5,683,448 A | 11/1997 | Cragg |
| 5,683,449 A | 11/1997 | Marcade |
| 5,683,450 A | 11/1997 | Goicoechea et al. |
| 5,683,451 A | 11/1997 | Lenker et al. |
| 5,683,452 A | 11/1997 | Barone et al. |
| 5,683,453 A | 11/1997 | Palmaz |
| 5,690,642 A | 11/1997 | Osborne et al. |
| 5,690,643 A | 11/1997 | Wijay |
| 5,690,644 A | 11/1997 | Yurek et al. |
| 5,693,066 A | 12/1997 | Rupp et al. |
| 5,693,084 A | 12/1997 | Chuter |
| 5,693,086 A | 12/1997 | Goicoechea et al. |
| 5,693,087 A | 12/1997 | Parodi |
| 5,693,088 A | 12/1997 | Lazarus |
| 5,695,516 A | 12/1997 | Fischell et al. |
| 5,695,517 A | 12/1997 | Marin et al. |
| 5,697,948 A | 12/1997 | Marin et al. |
| 5,709,703 A | 1/1998 | Lukic et al. |
| 5,713,917 A | 2/1998 | Leonhardt |
| 5,716,365 A | 2/1998 | Goicoechea et al. |
| 5,716,393 A | 2/1998 | Lindenberg et al. |
| 5,718,724 A | 2/1998 | Goicoechea et al. |
| 5,718,973 A | 2/1998 | Lewis et al. |
| 5,720,735 A | 2/1998 | Dorros |
| 5,720,776 A | 2/1998 | Chuter et al. |
| 5,723,004 A | 3/1998 | Dereume et al. |
| 5,733,267 A | 3/1998 | Del Toro |
| 5,733,325 A | 3/1998 | Robinson et al. |
| 5,746,766 A | 5/1998 | Edoga |
| 5,746,776 A | 5/1998 | Smith et al. |
| 5,749,880 A | 5/1998 | Banas et al. |
| 5,755,770 A | 5/1998 | Ravenscroft |
| 5,755,771 A | 5/1998 | Penn et al. |
| 5,755,777 A | 5/1998 | Chuter |
| 5,765,682 A | 6/1998 | Bley et al. |
| 5,766,203 A | 6/1998 | Imran et al. |
| 5,769,885 A | 6/1998 | Quiachon et al. |
| 5,769,887 A | 6/1998 | Brown et al. |
| 5,782,855 A | 7/1998 | Lau et al. |
| 5,782,909 A | 7/1998 | Quiachon et al. |
| 5,800,456 A | 9/1998 | Maeda et al. |
| 5,800,508 A | 9/1998 | Goicochea et al. |
| 5,800,526 A | 9/1998 | Anderson et al. |
| 5,800,540 A | 9/1998 | Chin |
| 5,810,836 A | 9/1998 | Hussein et al. |
| 5,817,100 A | 10/1998 | Igaki |
| 5,824,037 A | 10/1998 | Fogarty et al. |
| 5,824,039 A | 10/1998 | Piplani et al. |
| 5,824,040 A | 10/1998 | Cox et al. |
| 5,824,053 A | 10/1998 | Khosravi et al. |
| 5,843,160 A | 12/1998 | Rhodes |
| 5,843,162 A | 12/1998 | Inoue |
| 5,843,164 A | 12/1998 | Frantzen et al. |
| 5,843,167 A | 12/1998 | Dwyer et al. |
| 5,851,228 A | 12/1998 | Pinheiro |
| 5,855,599 A | 1/1999 | Wan |
| 5,860,998 A | 1/1999 | Robinson et al. |
| 5,865,844 A | 2/1999 | Plaia et al. |
| 5,867,432 A | 2/1999 | Toda |
| 5,868,783 A | 2/1999 | Tower |
| 5,871,536 A | 2/1999 | Lazarus |
| 5,876,432 A | 3/1999 | Lau et al. |
| 5,879,321 A | 3/1999 | Hill |
| 5,879,366 A | 3/1999 | Shaw et al. |
| 5,891,193 A | 4/1999 | Robinson et al. |
| 5,893,868 A | 4/1999 | Hanson et al. |
| 5,893,887 A | 4/1999 | Jayaraman |
| 5,902,334 A | 5/1999 | Dwyer et al. |
| 5,906,640 A | 5/1999 | Penn et al. |
| 5,906,641 A | 5/1999 | Thompson et al. |
| 5,916,263 A | 6/1999 | Goicoechea et al. |
| 5,919,225 A | 7/1999 | Lau et al. |
| 5,925,075 A | 7/1999 | Myers et al. |
| 5,928,279 A | 7/1999 | Shannon et al. |
| 5,935,161 A | 8/1999 | Robinson et al. |
| 5,938,696 A | 8/1999 | Goicoechea et al. |
| 5,948,018 A | 9/1999 | Dereume et al. |
| 5,957,973 A | 9/1999 | Quiachon et al. |
| 5,961,546 A | 10/1999 | Robinson et al. |
| 5,961,548 A | 10/1999 | Shmulewitz |
| 6,001,125 A | 12/1999 | Golds et al. |
| 6,004,347 A | 12/1999 | McNamara et al. |
| 6,004,348 A | 12/1999 | Banas et al. |
| 6,017,363 A | 1/2000 | Hojeibane |
| 6,019,777 A | 2/2000 | Mackenzie |
| 6,019,785 A | 2/2000 | Strecker |
| 6,027,508 A | 2/2000 | Ren et al. |
| 6,027,779 A | 2/2000 | Campbell et al. |
| 6,027,811 A | 2/2000 | Campbell et al. |
| 6,030,414 A | 2/2000 | Taheri |
| 6,030,415 A | 2/2000 | Chuter |
| 6,039,749 A | 3/2000 | Marin et al. |
| 6,039,755 A | 3/2000 | Edwin et al. |
| 6,039,758 A | 3/2000 | Quiachon et al. |
| 6,045,557 A | 4/2000 | White et al. |
| 6,051,020 A | 4/2000 | Goicoechea et al. |
| 6,053,940 A | 4/2000 | Wijay |
| 6,056,722 A | 5/2000 | Jayaraman |
| 6,059,813 A | 5/2000 | Vrba et al. |
| 6,063,092 A | 5/2000 | Shin |
| 6,063,113 A | 5/2000 | Kavteladze et al. |
| 6,070,589 A | 6/2000 | Keith et al. |
| 6,074,398 A | 6/2000 | Leschinsky |
| 6,077,296 A | 6/2000 | Shokoohi et al. |
| 6,077,297 A | 6/2000 | Robinson et al. |
| 6,080,191 A | 6/2000 | Summers |
| 6,086,611 A | 7/2000 | Duffy et al. |
| 6,090,128 A | 7/2000 | Douglas |
| 6,090,135 A | 7/2000 | Plaia et al. |
| 6,093,194 A | 7/2000 | Mikus et al. |
| 6,093,203 A | 7/2000 | Uflacker |
| 6,096,027 A | 8/2000 | Layne |
| 6,106,548 A | 8/2000 | Roubin et al. |
| 6,113,607 A | 9/2000 | Lau et al. |
| 6,117,167 A | 9/2000 | Goicoechea et al. |
| 6,123,722 A | 9/2000 | Fogarty et al. |
| 6,123,723 A | 9/2000 | Konya et al. |
| 6,126,685 A | 10/2000 | Lenker et al. |
| 6,129,756 A | 10/2000 | Kugler et al. |
| 6,143,016 A | 11/2000 | Bleam et al. |
| 6,146,389 A | 11/2000 | Geitz |
| 6,152,944 A | 11/2000 | Holman et al. |
| 6,159,195 A | 12/2000 | Ha et al. |
| 6,162,237 A | 12/2000 | Chan |
| 6,165,195 A | 12/2000 | Wilson et al. |
| 6,165,214 A | 12/2000 | Lazarus |
| 6,168,610 B1 | 1/2001 | Marin et al. |
| 6,171,281 B1 | 1/2001 | Zhang |
| 6,183,481 B1 | 2/2001 | Lee et al. |
| 6,183,509 B1 | 2/2001 | Dibie |
| 6,187,036 B1 | 2/2001 | Shaolian |
| 6,187,037 B1 | 2/2001 | Satz |
| 6,192,944 B1 | 2/2001 | Greenhalgh |
| 6,193,726 B1 | 2/2001 | Vanney |
| 6,197,049 B1 | 3/2001 | Shaolian et al. |
| 6,203,735 B1 | 3/2001 | Edwin et al. |
| 6,210,422 B1 | 4/2001 | Douglas |
| 6,210,429 B1 | 4/2001 | Vardi et al. |
| 6,214,038 B1 | 4/2001 | Piplani et al. |
| 6,221,081 B1 | 4/2001 | Mikus et al. |
| 6,221,090 B1 | 4/2001 | Wilson |
| 6,221,098 B1 | 4/2001 | Wilson |
| 6,221,102 B1 | 4/2001 | Baker et al. |
| 6,224,627 B1 | 5/2001 | Armstrong et al. |
| 6,231,563 B1 | 5/2001 | White et al. |
| 6,238,410 B1 | 5/2001 | Vrba et al. |
| 6,254,609 B1 | 7/2001 | Vrba et al. |
| 6,254,628 B1 | 7/2001 | Wallace et al. |
| 6,261,316 B1 | 7/2001 | Shaolian et al. |
| 6,264,682 B1 | 7/2001 | Wilson et al. |
| 6,273,909 B1 | 8/2001 | Kugler et al. |
| 6,280,466 B1 | 8/2001 | Kugler et al. |
| 6,280,467 B1 | 8/2001 | Leonhardt |

(56) References Cited

U.S. PATENT DOCUMENTS

| | | |
|---|---|---|
| 6,283,991 B1 | 9/2001 | Cox et al. |
| 6,287,329 B1 | 9/2001 | Duerig et al. |
| 6,299,634 B1 | 10/2001 | Bergeron |
| 6,312,406 B1 | 11/2001 | Jayaraman |
| 6,315,792 B1 | 11/2001 | Armstrong et al. |
| 6,331,184 B1 | 12/2001 | Abrams |
| 6,331,190 B1 | 12/2001 | Shokoohi et al. |
| 6,348,066 B1 | 2/2002 | Pinchuk et al. |
| 6,350,278 B1 | 2/2002 | Lenker et al. |
| 6,352,553 B1 | 3/2002 | Van der Burg et al. |
| 6,352,561 B1 | 3/2002 | Leopold et al. |
| 6,355,060 B1 | 3/2002 | Lenker et al. |
| 6,361,544 B1 | 3/2002 | Wilson et al. |
| 6,361,555 B1 | 3/2002 | Wilson |
| 6,361,557 B1 | 3/2002 | Gittings et al. |
| 6,361,559 B1 | 3/2002 | Houser et al. |
| 6,361,637 B2 | 3/2002 | Martin et al. |
| 6,380,457 B1 | 4/2002 | Yurek et al. |
| 6,383,213 B2 | 5/2002 | Wilson et al. |
| 6,387,120 B2 | 5/2002 | Wilson et al. |
| 6,395,017 B1 | 5/2002 | Dwyer |
| 6,395,018 B1 | 5/2002 | Castaneda |
| 6,395,019 B2 | 5/2002 | Chobotov |
| 6,398,807 B1 | 6/2002 | Chouinard et al. |
| 6,409,750 B1 | 6/2002 | Hyodoh et al. |
| 6,409,757 B1 | 6/2002 | Trout, III et al. |
| 6,416,474 B1 | 7/2002 | Penner et al. |
| 6,416,529 B1 | 7/2002 | Holman et al. |
| 6,416,542 B1 | 7/2002 | Marcade et al. |
| 6,428,567 B2 | 8/2002 | Wilson et al. |
| 6,432,130 B1 | 8/2002 | Hanson |
| 6,432,131 B1 | 8/2002 | Ravenscroft |
| 6,432,134 B1 | 8/2002 | Anson et al. |
| 6,440,161 B1 | 8/2002 | Madrid et al. |
| 6,447,540 B1 | 9/2002 | Fontaine et al. |
| 6,451,043 B1 | 9/2002 | McInnes et al. |
| 6,464,721 B1 | 10/2002 | Marcade et al. |
| 6,475,166 B1 | 11/2002 | Escano |
| 6,475,170 B1 | 11/2002 | Doron et al. |
| 6,482,211 B1 | 11/2002 | Choi |
| 6,485,513 B1 | 11/2002 | Fan |
| 6,491,719 B1 | 12/2002 | Fogarty et al. |
| 6,500,202 B1 | 12/2002 | Shaolian et al. |
| 6,508,833 B2 | 1/2003 | Pavcnik et al. |
| 6,508,835 B1 | 1/2003 | Shaolian et al. |
| 6,508,836 B2 | 1/2003 | Wilson et al. |
| 6,511,325 B1 | 1/2003 | Lalka et al. |
| 6,514,281 B1 | 2/2003 | Blaeser et al. |
| 6,517,569 B2 | 2/2003 | Mikus et al. |
| 6,517,572 B2 | 2/2003 | Kugler et al. |
| 6,517,573 B1 | 2/2003 | Pollock et al. |
| 6,520,988 B1 | 2/2003 | Colombo et al. |
| 6,524,335 B1 | 2/2003 | Hartley et al. |
| 6,533,811 B1 | 3/2003 | Ryan et al. |
| 6,544,278 B1 | 4/2003 | Vrba et al. |
| 6,551,350 B1 | 4/2003 | Thornton et al. |
| 6,558,396 B1 | 5/2003 | Inoue |
| 6,562,063 B1 | 5/2003 | Euteneuer et al. |
| 6,565,596 B1 | 5/2003 | White et al. |
| 6,565,597 B1 | 5/2003 | Fearnot et al. |
| RE38,146 E | 6/2003 | Palmaz et al. |
| 6,572,645 B2 | 6/2003 | Leonhardt |
| 6,576,005 B1 | 6/2003 | Geitz |
| 6,576,009 B2 | 6/2003 | Ryan et al. |
| 6,579,312 B2 | 6/2003 | Wilson et al. |
| 6,582,390 B1 | 6/2003 | Sanderson |
| 6,582,460 B1 | 6/2003 | Cryer |
| 6,585,758 B1 | 7/2003 | Chouinard et al. |
| 6,589,213 B2 | 7/2003 | Reydel |
| 6,592,548 B2 | 7/2003 | Jayaraman |
| 6,592,614 B2 | 7/2003 | Lenker et al. |
| 6,592,615 B1 | 7/2003 | Marcade et al. |
| 6,599,315 B2 | 7/2003 | Wilson |
| 6,607,552 B1 | 8/2003 | Hanson |
| 6,613,073 B1 | 9/2003 | White et al. |
| 6,616,675 B1 | 9/2003 | Evard et al. |
| 6,652,579 B1 | 11/2003 | Cox et al. |
| 6,656,213 B2 | 12/2003 | Solem |
| 6,660,030 B2 | 12/2003 | Shaolian et al. |
| 6,663,665 B2 | 12/2003 | Shaolian et al. |
| 6,669,718 B2 | 12/2003 | Besselink |
| 6,669,719 B2 | 12/2003 | Wallace et al. |
| 6,676,666 B2 | 1/2004 | Vrba et al. |
| 6,689,157 B2 | 2/2004 | Madrid et al. |
| 6,702,843 B1 | 3/2004 | Brown et al. |
| 6,722,705 B2 | 4/2004 | Korkor |
| 6,733,523 B2 | 5/2004 | Shaolian et al. |
| 6,755,855 B2 | 6/2004 | Yurek et al. |
| 6,761,733 B2 | 7/2004 | Chobotov et al. |
| 6,767,359 B2 | 7/2004 | Weadock |
| 6,790,224 B2 | 9/2004 | Gerberding |
| 6,800,065 B2 | 10/2004 | Duane et al. |
| 6,814,752 B1 | 11/2004 | Chuter |
| 6,818,014 B2 | 11/2004 | Brown et al. |
| 6,821,292 B2 | 11/2004 | Pazienza et al. |
| 6,827,726 B2 | 12/2004 | Parodi |
| 6,840,950 B2 | 1/2005 | Stanford et al. |
| 6,846,316 B2 | 1/2005 | Abrams |
| 6,849,086 B2 | 2/2005 | Cragg et al. |
| 6,858,038 B2 | 2/2005 | Heuser |
| 6,875,229 B2 | 4/2005 | Wilson et al. |
| 6,887,249 B1 | 5/2005 | Houser et al. |
| 6,887,251 B1 | 5/2005 | Suval |
| 6,896,699 B2 | 5/2005 | Wilson et al. |
| 6,899,727 B2 | 5/2005 | Armstrong et al. |
| 6,899,728 B1 | 5/2005 | Phillips et al. |
| 6,908,477 B2 | 6/2005 | McGuckin |
| 6,923,829 B2 | 8/2005 | Boyle et al. |
| 6,929,661 B2 | 8/2005 | Bolduc et al. |
| 6,932,837 B2 | 8/2005 | Amplatz et al. |
| 6,939,368 B2 | 9/2005 | Simso |
| 6,939,371 B2 | 9/2005 | Kugler et al. |
| 6,939,377 B2 | 9/2005 | Jayaraman et al. |
| 6,942,692 B2 | 9/2005 | Landau et al. |
| 6,942,693 B2 | 9/2005 | Chouinard et al. |
| 6,951,572 B1 | 10/2005 | Douglas |
| 6,953,475 B2 | 10/2005 | Shaolian et al. |
| 6,955,679 B1 | 10/2005 | Hendricksen et al. |
| 6,955,688 B2 | 10/2005 | Wilson et al. |
| 6,960,217 B2 | 11/2005 | Bolduc |
| 6,962,602 B2 | 11/2005 | Vardi |
| 6,981,982 B2 | 1/2006 | Armstrong et al. |
| 6,984,244 B2 | 1/2006 | Perez et al. |
| 6,991,639 B2 | 1/2006 | Holman et al. |
| 6,994,722 B2 | 2/2006 | DiCarlo |
| 7,004,926 B2 | 2/2006 | Navia et al. |
| 7,004,964 B2 | 2/2006 | Thompson et al. |
| 7,004,967 B2 | 2/2006 | Chouinard et al. |
| 7,014,653 B2 | 3/2006 | Ouriel et al. |
| 7,025,779 B2 | 4/2006 | Elliott |
| 7,029,496 B2 | 4/2006 | Rakos et al. |
| 7,074,236 B2 | 7/2006 | Rabkin et al. |
| 7,122,051 B1 | 10/2006 | Dallara et al. |
| 7,122,052 B2 | 10/2006 | Greenhalgh |
| 7,125,464 B2 | 10/2006 | Chobotov et al. |
| 7,144,422 B1 | 12/2006 | Rao |
| 7,160,318 B2 | 1/2007 | Greenberg et al. |
| 7,162,302 B2 | 1/2007 | Wang et al. |
| 7,163,715 B1 | 1/2007 | Kramer |
| 7,175,652 B2 | 2/2007 | Cook et al. |
| 7,175,657 B2 | 2/2007 | Khan et al. |
| 7,189,256 B2 | 3/2007 | Smith |
| 7,201,770 B2 | 4/2007 | Johnson et al. |
| 7,235,095 B2 | 6/2007 | Haverkost et al. |
| 7,244,444 B2 | 7/2007 | Bates |
| 7,261,733 B1 | 8/2007 | Brown et al. |
| 7,264,631 B2 | 9/2007 | DeCarlo |
| 7,264,632 B2 | 9/2007 | Wright et al. |
| 7,267,685 B2 | 9/2007 | Butaric et al. |
| 7,270,675 B2 | 9/2007 | Chun et al. |
| 7,285,130 B2 | 10/2007 | Austin |
| 7,314,483 B2 | 1/2008 | Landau et al. |
| 7,320,703 B2 | 1/2008 | DiMatteo et al. |
| 7,402,168 B2 | 7/2008 | Acosta et al. |

(56) References Cited

U.S. PATENT DOCUMENTS

| | | |
|---|---|---|
| 7,425,219 B2 | 9/2008 | Quadri et al. |
| 7,435,253 B1 | 10/2008 | Hartley et al. |
| 7,491,230 B2 | 2/2009 | Holman et al. |
| 7,520,895 B2 | 4/2009 | Douglas et al. |
| 7,537,606 B2 | 5/2009 | Hartley |
| 7,553,324 B2 | 6/2009 | Andreas et al. |
| 7,572,289 B2 | 8/2009 | Sisken et al. |
| 7,651,519 B2 | 1/2010 | Dittman |
| 7,691,135 B2 | 4/2010 | Shaolian et al. |
| 7,722,657 B2 | 5/2010 | Hartley |
| 7,892,277 B2 | 2/2011 | Douglas et al. |
| 2001/0001128 A1 | 5/2001 | Holman et al. |
| 2001/0025195 A1 | 9/2001 | Shaolian et al. |
| 2002/0029075 A1 | 3/2002 | Leohardt |
| 2002/0049412 A1 | 4/2002 | Madrid et al. |
| 2002/0052644 A1 | 5/2002 | Shaolian et al. |
| 2002/0123786 A1 | 9/2002 | Gittings et al. |
| 2002/0156516 A1 | 10/2002 | Vardi |
| 2002/0165602 A1 | 11/2002 | Douglas et al. |
| 2003/0004560 A1 | 1/2003 | Chobotov et al. |
| 2003/0023299 A1 | 1/2003 | Amplatz et al. |
| 2003/0065380 A1 | 4/2003 | Kugler et al. |
| 2003/0065385 A1 | 4/2003 | Weadock |
| 2003/0083738 A1 | 5/2003 | Holman et al. |
| 2003/0097169 A1 | 5/2003 | Brucker et al. |
| 2003/0149465 A1 | 8/2003 | Heidner et al. |
| 2003/0191491 A1 | 10/2003 | Duane et al. |
| 2003/0236565 A1 | 12/2003 | DiMatteo et al. |
| 2004/0010265 A1 | 1/2004 | Karpiel |
| 2004/0073289 A1 | 4/2004 | Hartley |
| 2004/0138735 A1 | 7/2004 | Shaolian et al. |
| 2004/0167618 A1 | 8/2004 | Shaolian et al. |
| 2004/0176832 A1 | 9/2004 | Hartley et al. |
| 2005/0033403 A1 | 2/2005 | Ward et al. |
| 2005/0038494 A1 | 2/2005 | Eidenschink |
| 2005/0049672 A1 | 3/2005 | Murphy |
| 2005/0058327 A1 | 3/2005 | Pieper |
| 2005/0059994 A1 | 3/2005 | Walak et al. |
| 2005/0060018 A1 | 3/2005 | Dittman |
| 2005/0080025 A1 | 3/2005 | Mackiewicz et al. |
| 2005/0080474 A1 | 4/2005 | Andreas et al. |
| 2005/0085842 A1 | 4/2005 | Eversull et al. |
| 2005/0085845 A1 | 4/2005 | Hilaire et al. |
| 2005/0113693 A1 | 5/2005 | Smith et al. |
| 2005/0113905 A1 | 5/2005 | Greenberg et al. |
| 2005/0113906 A9 | 5/2005 | Bolduc et al. |
| 2005/0119721 A1 | 6/2005 | Rabkin et al. |
| 2005/0119731 A1 | 6/2005 | Brucker et al. |
| 2005/0121043 A1 | 6/2005 | Abrams |
| 2005/0121120 A1 | 6/2005 | Van Kijk et al. |
| 2005/0131516 A1 | 6/2005 | Greenhalgh |
| 2005/0159803 A1 | 7/2005 | Lad et al. |
| 2005/0165480 A1 | 7/2005 | Jordan et al. |
| 2005/0171598 A1 | 8/2005 | Schaeffer |
| 2005/0216043 A1 | 9/2005 | Blatter et al. |
| 2005/0220848 A1 | 10/2005 | Bates |
| 2005/0228476 A1 | 10/2005 | Dimatteo et al. |
| 2005/0234542 A1 | 10/2005 | Melsheimer |
| 2005/0240153 A1 | 10/2005 | Opie |
| 2005/0240258 A1 | 10/2005 | Bolduc et al. |
| 2005/0240259 A1 | 10/2005 | Sisken et al. |
| 2005/0240260 A1 | 10/2005 | Bolduc |
| 2005/0273150 A1 | 12/2005 | Howell et al. |
| 2005/0288772 A1 | 12/2005 | Douglas |
| 2006/0030924 A1 | 2/2006 | Van Der Leest et al. |
| 2006/0074475 A1 | 4/2006 | Gumm |
| 2006/0100686 A1 | 5/2006 | Bolduc et al. |
| 2006/0142838 A1 | 6/2006 | Molaei et al. |
| 2006/0161244 A1 | 7/2006 | Seguin |
| 2006/0217794 A1 | 9/2006 | Ruiz et al. |
| 2006/0229700 A1 | 10/2006 | Acosta et al. |
| 2006/0233990 A1 | 10/2006 | Humphrey et al. |
| 2006/0233991 A1 | 10/2006 | Humphrey et al. |
| 2006/0264801 A1 | 11/2006 | Bolling et al. |
| 2006/0271163 A1 | 11/2006 | Shokoohi et al. |
| 2006/0287713 A1 | 12/2006 | Douglas et al. |
| 2007/0010867 A1 | 1/2007 | Carter et al. |
| 2007/0021822 A1 | 1/2007 | Boatman |
| 2007/0027522 A1 | 2/2007 | Chang et al. |
| 2007/0027526 A1 | 2/2007 | Demetriades et al. |
| 2007/0027531 A1 | 2/2007 | DiMatteo et al. |
| 2007/0112420 A1 | 5/2007 | LaDuca |
| 2007/0203571 A1 | 8/2007 | Kaplan et al. |
| 2007/0213805 A1 | 9/2007 | Schaeffer et al. |
| 2007/0244540 A1 | 10/2007 | Pryor |
| 2007/0260302 A1 | 11/2007 | Igaki |
| 2007/0299499 A1 | 12/2007 | Hartley |
| 2008/0015681 A1 | 1/2008 | Wilson |
| 2008/0071343 A1 | 3/2008 | Mayberry et al. |
| 2008/0086191 A1 | 4/2008 | Valencia |
| 2008/0109065 A1 | 5/2008 | Bowe |
| 2008/0172122 A1 | 7/2008 | Mayberry et al. |
| 2008/0269867 A1 | 10/2008 | Johnson |
| 2009/0012602 A1 | 1/2009 | Quadri |
| 2009/0105806 A1 | 4/2009 | Benjamin et al. |
| 2009/0216315 A1 | 8/2009 | Schreck et al. |
| 2009/0259298 A1 | 10/2009 | Mayberry et al. |
| 2010/0004730 A1 | 1/2010 | Benjamin et al. |
| 2010/0179636 A1 | 7/2010 | Pham et al. |
| 2010/0179638 A1 | 7/2010 | Shaolian et al. |
| 2011/0015718 A1 | 1/2011 | Schreck |
| 2011/0022153 A1 | 1/2011 | Schreck et al. |
| 2011/0054586 A1 | 3/2011 | Mayberry et al. |
| 2011/0054587 A1 | 3/2011 | Mayberry et al. |
| 2011/0054594 A1 | 3/2011 | Mayberry et al. |
| 2011/0224772 A1 | 9/2011 | Mayberry et al. |
| 2011/0224782 A1 | 9/2011 | Douglas et al. |
| 2012/0165917 A1 | 6/2012 | Schreck et al. |
| 2012/0226341 A1 | 9/2012 | Schreck et al. |
| 2012/0277846 A1 | 11/2012 | Schreck et al. |
| 2012/0277847 A1 | 11/2012 | Benjamin et al. |

FOREIGN PATENT DOCUMENTS

| | | |
|---|---|---|
| CA | 2133530 | 4/1995 |
| CA | 2220141 | 11/1996 |
| CA | 2287406 A3 | 12/1997 |
| DE | 295 21 548 U1 | 2/1995 |
| DE | 295 21 776 U1 | 2/1995 |
| DE | 100 17 147 | 10/2001 |
| EP | 0 282 175 B1 | 11/1991 |
| EP | 0 458 568 B1 | 11/1991 |
| EP | 0 323 176 B1 | 3/1994 |
| EP | 0 596 145 A1 | 5/1994 |
| EP | 0 177 330 B1 | 6/1994 |
| EP | 0 621 015 A1 | 10/1994 |
| EP | 0 659 389 A1 | 6/1995 |
| EP | 0 688 545 A1 | 12/1995 |
| EP | 0 689 806 A2 | 12/1995 |
| EP | 0 712 614 A1 | 5/1996 |
| EP | 0 732 089 A2 | 9/1996 |
| EP | 0 740 928 A2 | 11/1996 |
| EP | 0 747 020 A2 | 12/1996 |
| EP | 0 775 470 A1 | 5/1997 |
| EP | 0 782 841 A2 | 7/1997 |
| EP | 0 783 873 | 7/1997 |
| EP | 0 783 874 A2 | 7/1997 |
| EP | 0 880 938 A1 | 12/1998 |
| EP | 0 880 948 A1 | 12/1998 |
| EP | 0 904 745 A2 | 3/1999 |
| EP | 0 696 447 B1 | 1/2000 |
| EP | 0 974 314 A2 | 1/2000 |
| EP | 0 732 088 | 4/2000 |
| EP | 0 732 088 B1 | 4/2000 |
| EP | 1 433 438 | 6/2004 |
| ES | 1 038 606 | 7/1998 |
| JP | 04-25755 | 6/1990 |
| JP | H05-81257 | 11/1993 |
| JP | 07-47134 | 3/1994 |
| JP | 30-09638 | 4/1994 |
| JP | 08-52165 | 6/1995 |
| JP | 09-164209 | 12/1995 |
| JP | 08-336597 | 12/1996 |
| JP | 09-511160 | 11/1997 |

(56) References Cited

FOREIGN PATENT DOCUMENTS

| | | |
|---|---|---|
| JP | 2000-500047 | 1/2000 |
| WO | WO 93/13825 | 7/1993 |
| WO | WO 94/24961 | 2/1994 |
| WO | WO 95/21592 | 8/1995 |
| WO | WO 96/34580 | 11/1996 |
| WO | WO 96/38101 | 12/1996 |
| WO | WO 96/39999 | 12/1996 |
| WO | WO 96/41589 | 12/1996 |
| WO | WO 97/10757 | 3/1997 |
| WO | WO 97/10777 | 3/1997 |
| WO | WO 97/14375 | 4/1997 |
| WO | WO 97/17911 | 5/1997 |
| WO | WO 97/19652 | 6/1997 |
| WO | WO 97/26936 | 7/1997 |
| WO | WO 97/33532 | 9/1997 |
| WO | WO 97/45072 | 12/1997 |
| WO | WO 98/02100 | 1/1998 |
| WO | WO 98/20812 | 5/1998 |
| WO | WO 99/29262 | 6/1999 |
| WO | WO 99/44536 | 9/1999 |
| WO | WO 99/47077 | 9/1999 |
| WO | WO 99/58084 | 11/1999 |
| WO | WO 00/33769 | 6/2000 |
| WO | WO 00/53251 | 9/2000 |
| WO | WO/0067674 | 11/2000 |
| WO | WO 01/03762 A1 | 1/2001 |
| WO | WO 02/39888 A2 | 5/2002 |
| WO | WO 02/060345 A2 | 8/2002 |
| WO | WO 2005/037076 A2 | 4/2005 |
| WO | WO 2005/037141 A2 | 4/2005 |

OTHER PUBLICATIONS

U.S. Appl. No. 12/769,546, filed Apr. 28, 2010, Mayberry et al.
U.S. Appl. No. 12/769,581, filed Apr. 28, 2010, Mayberry et al.
Instructions for use of the Gore Excluder® AAA Prosthesis, pp. 1-17, Apr. 2009.
International Preliminary Report on Patentability; dated Oct. 12, 2010; International Application No. PCT/US2009/040239; 6 pages.
International Search Report and Written Opinion for International Application No. PCT/US09/40239, filed Apr. 10, 2009, Date of Issuance May 26, 2009, in 14 pages.
International Search Report for International Application No. PCT/US09/40239, filed Apr. 10, 2009, Date of Issuance May 26, 2009, in 3 pages.
Minion et al., "Technique of slow deployment of Gore Excluder endograft improves accuracy of placement", *J Vasc Surg* 43:852-4, 2006.
Patent Cooperation Treaty (PCT) International Search Report dated May 21, 2008 for International Application No. PCT/US2008/050915 Filed on Nov. 1, 2008, 7 pages.
Patent Cooperation Treaty (PCT) International Search Report, dated May 16, 2008 for International Application No. PCT/US2007/078565 Filed on Sep. 14, 2007, 7 pages.
Supplementary Partial European Search Report for Application No. EP 03790040, filed on Nov. 25, 2003, 3 pages.
Written Opinion of the International Searching Authority for International Application No. PCT/US09/40239, filed Apr. 10, 2009, Date of Completion of Opinion May 8, 2009, in 5 pages.
Japanese Office Action re JP Application No. JP 2011-504207, dated Jul. 9, 2013.
Japanese Office Action (Decision of Refusal) re JP Application No. JP 2011-504207, dated Dec. 4, 2013.

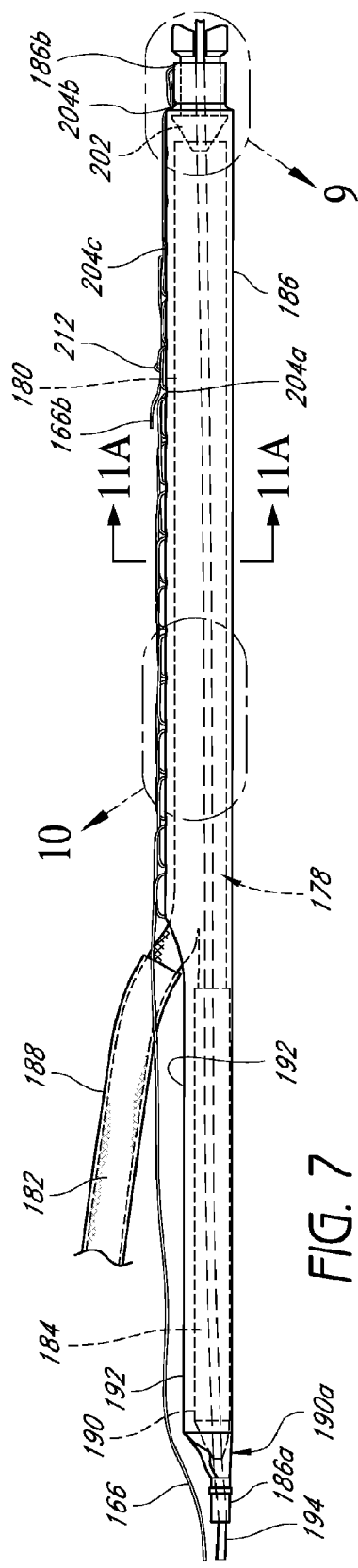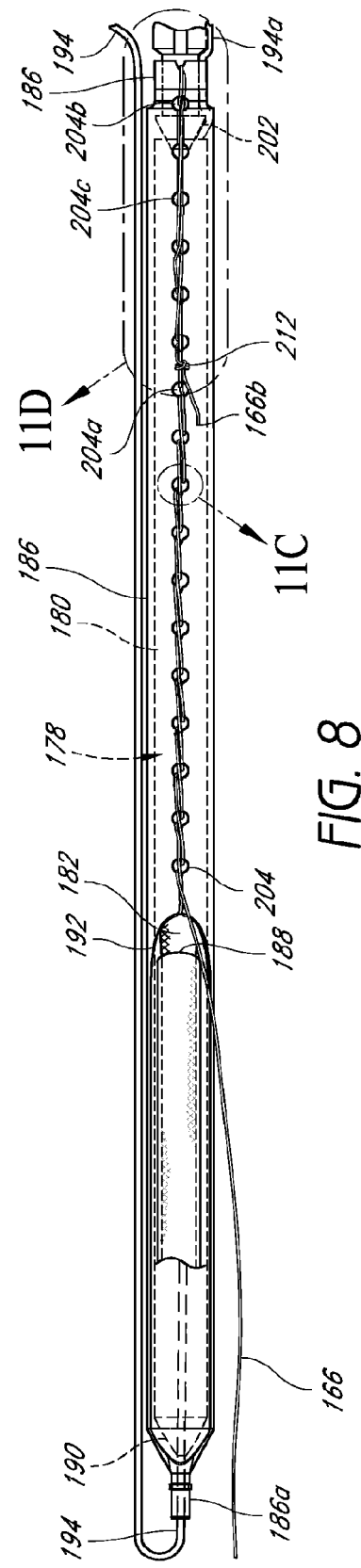

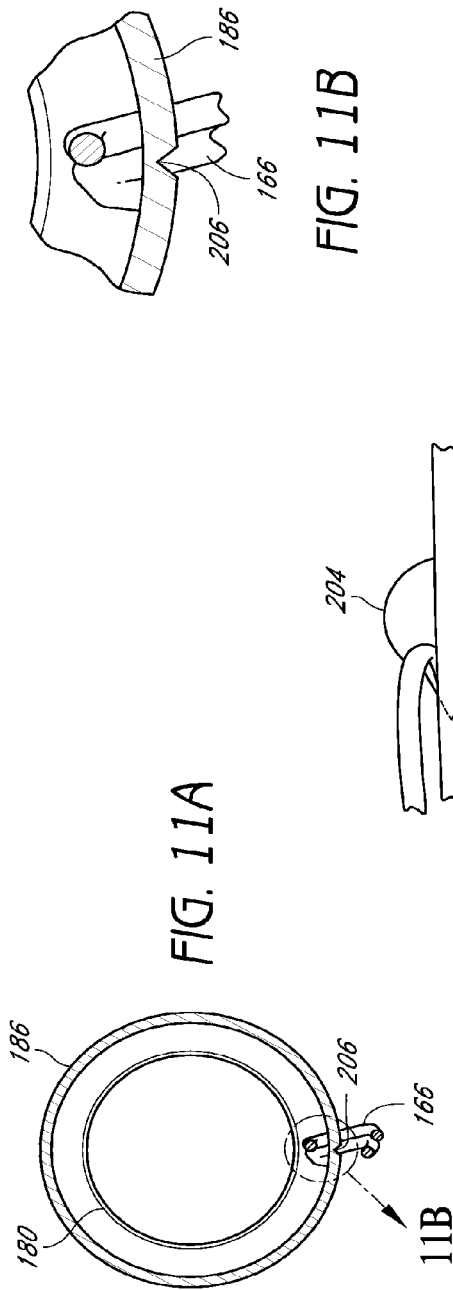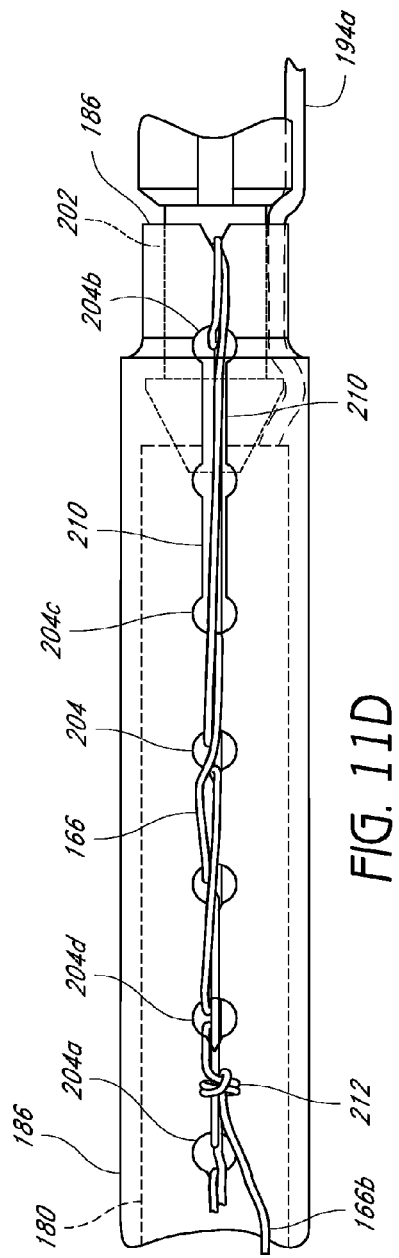

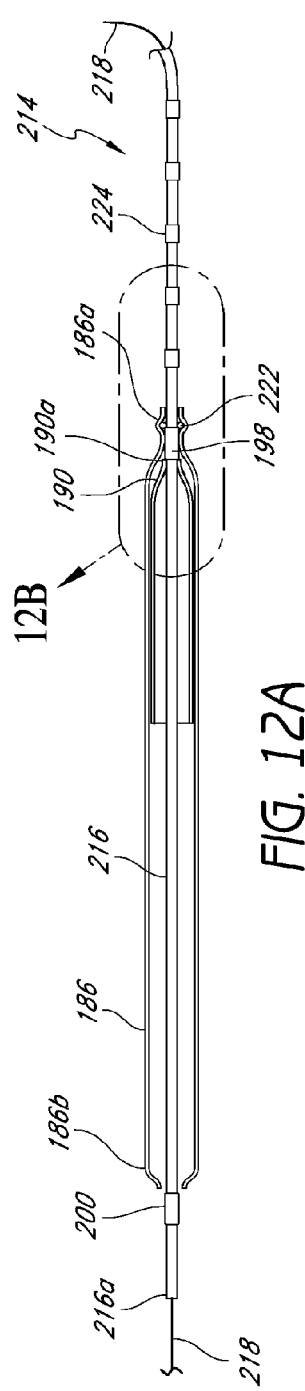
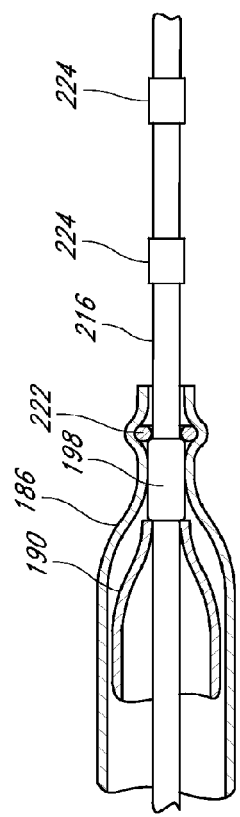
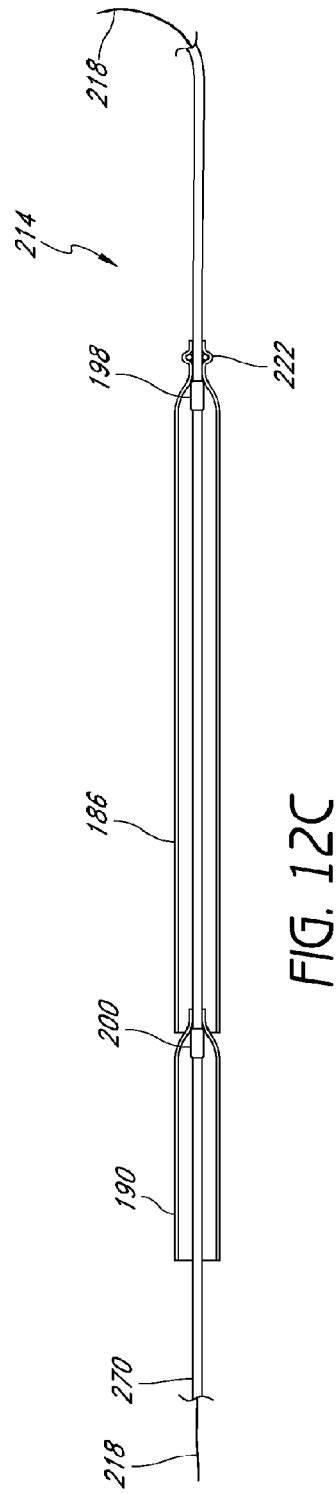
FIG. 12A
FIG. 12B
FIG. 12C

BIFURCATED GRAFT DEPLOYMENT SYSTEMS AND METHODS

This application is a divisional of U.S. patent application Ser. No. 13/046,541, filed Mar. 11, 2011, which is a continuation of U.S. patent application Ser. No. 12/101,863, filed Apr. 11, 2008, now U.S. Pat. No. 8,236,040, both of which are hereby incorporated by reference herein and made part of the present disclosure as if fully set forth herein.

BACKGROUND OF THE INVENTION

1. Technical Field

The present invention relates to endoluminal vascular prosthesis deployment, and in particular, to a deployment system for a bifurcated graft having at least one peelable sheath.

2. Description of the Related Art

An abdominal aortic aneurysm is a sac caused by an abnormal dilation of the wall of the aorta, a major artery of the body, as it passes through the abdomen. The abdomen is that portion of the body which lies between the thorax and the pelvis. It contains a cavity, known as the abdominal cavity, separated by the diaphragm from the thoracic cavity and lined with a serous membrane, the peritoneum. The aorta is the main trunk, or artery, from which the systemic arterial system proceeds. It arises from the left ventricle of the heart, passes upward, bends over and passes down through the thorax and through the abdomen to about the level of the fourth lumbar vertebra, where it divides into the two common iliac arteries.

The aneurysm usually arises in the infrarenal portion of the diseased aorta, for example, below the kidneys. When left untreated, the aneurysm may eventually cause rupture of the sac with ensuing fatal hemorrhaging in a very short time. High mortality associated with the rupture led initially to transabdominal surgical repair of abdominal aortic aneurysms. Surgery involving the abdominal wall, however, is a major undertaking with associated high risks. There is considerable mortality and morbidity associated with this magnitude of surgical intervention, which in essence involves replacing the diseased and aneurysmal segment of blood vessel with a prosthetic device which typically is a synthetic tube, or graft, usually fabricated of Polyester, Urethane, DACRON™, TEFLON™, or other suitable material.

To perform the surgical procedure requires exposure of the aorta through an abdominal incision which can extend from the rib cage to the pubis. The aorta must be closed both above and below the aneurysm, so that the aneurysm can then be opened and the thrombus, or blood clot, and arteriosclerotic debris removed. Small arterial branches from the back wall of the aorta are tied off. The DACRON™ tube, or graft, of approximately the same size of the normal aorta is sutured in place, thereby replacing the aneurysm. Blood flow is then reestablished through the graft. It is necessary to move the intestines in order to get to the back wall of the abdomen prior to clamping off the aorta.

If the surgery is performed prior to rupturing of the abdominal aortic aneurysm, the survival rate of treated patients is markedly higher than if the surgery is performed after the aneurysm ruptures, although the mortality rate is still quite high. If the surgery is performed prior to the aneurysm rupturing, the mortality rate is typically slightly less than 10%. Conventional surgery performed after the rupture of the aneurysm is significantly higher, one study reporting a mortality rate of 66.5%. Although abdominal aortic aneurysms can be detected from routine examinations, the patient may experience any pain from the condition. Thus, if the patient is not receiving routine examinations, it is possible that the aneurysm will progress to the rupture stage, wherein the mortality rates are significantly higher.

Disadvantages associated with the conventional, prior art surgery, in addition to the high mortality rate include the extended recovery period associated with such surgery; difficulties in suturing the graft, or tube, to the aorta; the loss of the existing aorta wall and thrombosis to support and reinforce the graft; the unsuitability of the surgery for many patients having abdominal aortic aneurysms; and the problems associated with performing the surgery on an emergency basis after the aneurysm has ruptured. A patient can expect to spend from one to two weeks in the hospital after the surgery, a major portion of which is spent in the intensive care unit, and a convalescence period at home from two to three months, particularly if the patient has other illnesses such as heart, lung, liver, and/or kidney disease, in which case the hospital stay is also lengthened. The graft must be secured, or sutured, to the remaining portion of the aorta, which may be difficult to perform because of the thrombosis present on the remaining portion of the aorta. Moreover, the remaining portion of the aorta wall is frequently friable, or easily crumbled.

Since many patients having abdominal aortic aneurysms have other chronic illnesses, such as heart, lung, liver, and/or kidney disease, coupled with the fact that many of these patients are older, the average age being approximately 67 years old, these patients are not ideal candidates for such major surgery.

More recently, a significantly less invasive clinical approach to aneurysm repair, known as endovascular grafting, has been developed. Parodi, et al. provide one of the first clinical descriptions of this therapy. Parodi, J. C., et al., "Transfemoral Intraluminal Graft Implantation for Abdominal Aortic Aneurysms," 5 Annals of Vascular Surgery 491 (1991). Endovascular grafting involves the transluminal placement of a prosthetic arterial graft within the lumen of the artery. The embodiments disclosed herein relate to the methods and apparatuses for deploying bifurcated and non-bifurcated grafts within the lumen or lumens of the blood vessels of the body.

SUMMARY OF SOME EXEMPLIFYING EMBODIMENTS

Certain embodiments described herein are directed to systems, methods and apparatuses for treating endovascular aneurysms or other endovascular defects. However, it will be appreciated that the systems, methods and apparatuses may have application to other fields. In some embodiments, the defects being treated may include, but are not limited to, abdominal aortic aneurysms, subclavian aneurysms, and thoracic aortic aneurysms, to name a few.

In some embodiments, such aneurysms are treated using an endoluminal vascular prosthesis deployment system for deploying an endoluminal vascular prosthesis having at least a main branch and a first branch, comprising a flexible catheter body that preferably comprises an outer sheath with a proximal and distal end, an inner core that extends through the outer sheath and is axially moveable with respect to the outer sheath, and a distal tip that is positioned adjacent the distal end of the outer sheath and is coupled to the inner core. In addition, in some embodiments, the deployment system preferably further comprises a main branch restraint that comprises a tubular member that surrounds and constrains at least the main branch portion, the tubular member having a first portion adjacent a first end of the tubular member, a second portion adjacent a second end of the tubular member, and an intermediate portion positioned between the first and second portions. In some embodiments, the tubular member preferably comprises a plurality of perforations.

In some embodiments, the deployment system preferably comprises a release wire extending through the plurality of perforations and configured to tear portions of the tubular member of the main branch restraint between the perforations to deploy the main branch portion when the release wire is proximally retracted by releasing at least one of the proximal portion or intermediate portion before the distal portion. Additionally, in some embodiments, the deployment system preferably comprises a first branch restraint that comprises a tubular member configured to releasably constrain the first branch portion, the first branch restraint being coupled to a first branch release mechanism.

In some embodiments, such aneurysms are treated using a method of deploying a bifurcated endoluminal vascular prosthesis comprising a main branch segment, a first branch segment, and a second branch segment in a patient's artery, the method comprising the following steps. Although the steps are presented in a particular order, such order is not required. Some of the steps listed below could be performed in a different order. The prosthesis could be deployed by positioning a hollow guidewire sheath across a bifurcation in a patient's artery and in a contralateral branch of the patient's artery, advancing the deployment catheter over through an iliac branch of the patient's artery, the deployment catheter comprising an outer sheath and an inner core that is axially moveable with respect to the outer sheath and configured to support the prosthesis within the outer sheath of the deployment catheter such that, when the inner core is distally advanced relative to the outer sheath, the prosthesis is caused to be exposed, axially positioning the inner core relative to the outer sheath such that the main branch segment, first branch segment, and second branch segment of the prosthesis is caused to be exposed, positioning the prosthesis in the bifurcation in the patient's artery by manipulating the inner core and/or the hollow guidewire sheath so that the main branch segment, first branch segment, and second branch segment of the prosthesis are in the desire position, deploying a main graft segment of the prosthesis by axially withdrawing a release wire that causes a main graft segment sheath constraining the main graft segment of the prosthesis to split and deploy the main graft segment, axially withdrawing the hollow guidewire sheath until the second branch restraint is withdrawn from the second branch segment and the second branch segment has been deployed, and axially withdrawing the inner core so as to axially withdraw a first branch restraint coupled thereto until the first branch has been deployed.

In some embodiments, the hollow guidewire sheath preferably comprises distal and proximal ends and a lumen extending therethrough. In some embodiments, the proximal end of the hollow guidewire assembly preferably extends from the contralateral branch outside the patient. In some embodiments, the hollow guidewire sheath is preferably positioned within the main branch segment and the second branch segment and is preferably configured to withdraw a second branch restraint removably positioned over the second branch segment after a predetermined length of the hollow guidewire has been axially withdrawn from the deployment catheter.

BRIEF DESCRIPTION OF THE DRAWINGS

These and other features, aspects and advantages will now be described in connection with certain embodiments, in reference to the accompanying drawings. The illustrated embodiments, however, are merely examples and are not intended to be limiting. The following are brief descriptions of the drawings.

FIG. 7 is a side view of the main branch portion restraint member of the embodiment of the deployment catheter shown in FIG. 3, before deployment of the main branch portion of the graft.

FIG. 8 is a top view of the main branch portion restraint member of the embodiment of the deployment catheter shown in FIG. 3, before deployment of the main branch portion of the graft.

FIG. 11A is a cross-sectional view of the main branch portion restraint member shown in FIG. 7 taken along line 11A-11A of FIG. 7.

FIG. 11B is an enlarged detail view of FIG. 11A taken along the curve 11B in FIG. 11A.

FIG. 11C is an enlarged detail view of FIG. 8 taken along the curve 11C in FIG. 8.

FIG. 11D is an enlarged detail view of FIG. 8 taken along the curve 11D in FIG. 8.

FIG. 12A is a schematic representation of the dual concentric guidewire assembly of the embodiment of the deployment catheter shown in FIG. 3, showing the position of the main branch restraint member and the contralateral branch restraint member before deployment of the main branch of the graft.

FIG. 12B is an enlarged detail view of FIG. 12A taken along the curve 12B in FIG. 12A.

FIG. 12C is a schematic representation of the dual concentric guidewire assembly (or guidewire sheath) of the embodiment of the deployment catheter shown in FIG. 3, showing the position of the main branch restraint member and the contralateral branch restraint member after deployment of the main branch portion of the graft.

DETAILED DESCRIPTION OF SOME EXEMPLIFYING EMBODIMENTS

Figure 1A:
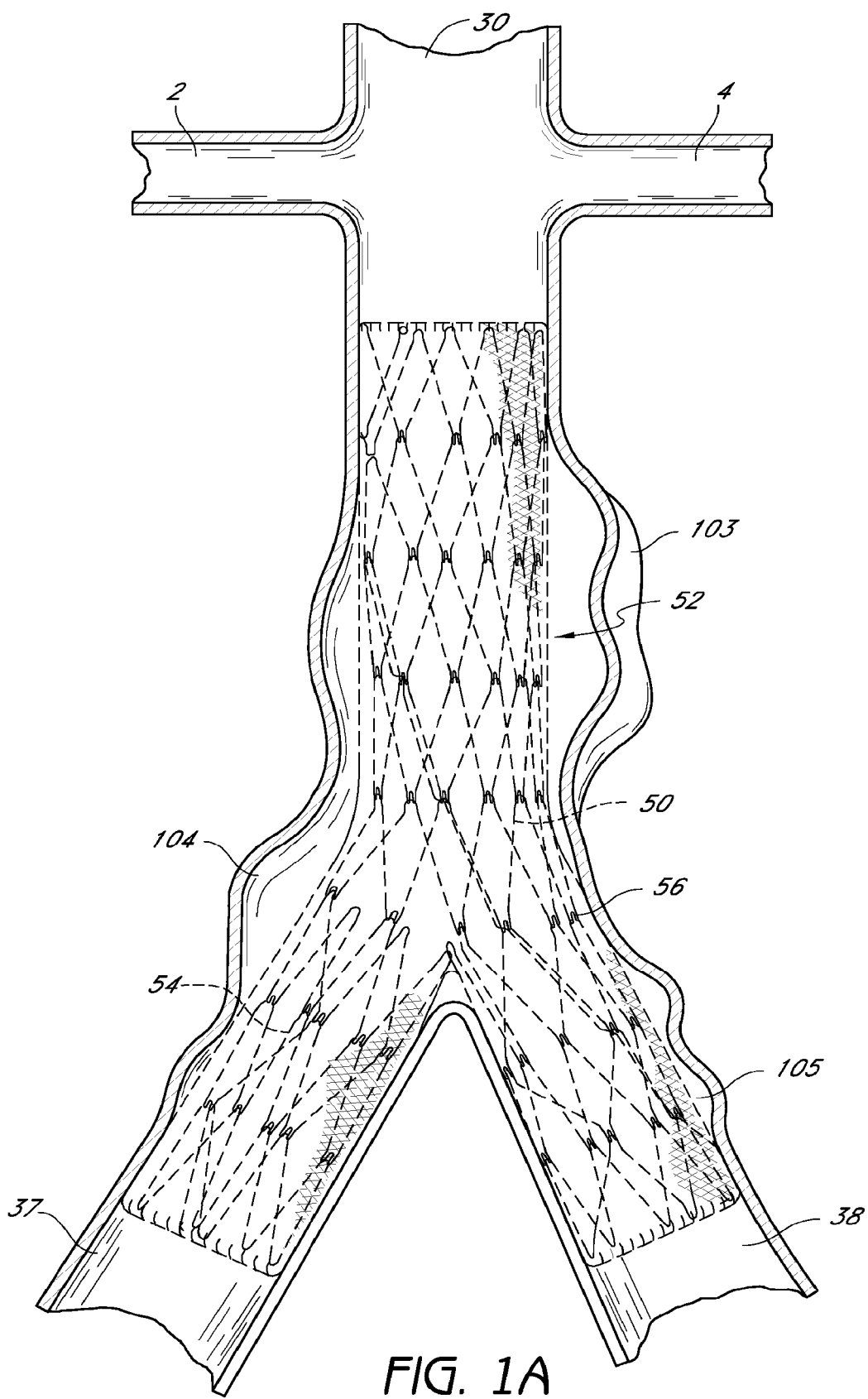
FIG. 1A is a schematic representation of an example of a bifurcated vascular prosthesis that can be used with deployment catheter disclosed herein, positioned at the bifurcation between the abdominal aorta and the right and left common iliac arteries.

The following detailed description is now directed to certain specific embodiments of the disclosure. In this description, reference is made to the figures wherein like parts are designated with like numerals throughout the description and the drawings. Described below are various embodiments of a delivery system for deploying a vascular graft including a deployment catheter and a hollow guidewire assembly which may be used to maintain access through an implanted vascular graft for subsequent catheterizations.

Endoluminal repair or exclusion of aortic aneurysms has been performed for the past several years. The goal of endoluminal aortic aneurysm exclusion has been to correct this life threatening disease in a minimally invasive manner in order to effectuate a patient's quick and complete recovery. Various vascular grafts exist in the prior art that have been used to exclude aortic aneurysms. In general, transluminally implantable prostheses adapted for use in the abdominal aorta comprise a tubular wire cage surrounded by a tubular PTFE or Dacron sleeve. Both balloon expandable and self-expandable support structures may be used to support the tubular sleeve. Without limitation, the deployment system disclosed herein can be used to deliver both straight and bifurcated endovascular prostheses adapted to treat both straight segment and bifurcated segment aneurysms.

Endoluminal implantation is an increasingly accepted technique for implanting vascular grafts. Typically, this procedure involves percutaneously inserting a vascular graft or prosthesis by using a delivery catheter. This process eliminates the need for major surgical intervention, thereby decreasing the risks associated with vascular and arterial surgery. Various embodiments of catheter delivery systems for prosthetic devices are described herein.

Certain current delivery systems for a bifurcated stent graft system or a graft having at least one branch portion may use two sheaths moving in opposing directions to deploy the distal segment of the graft before the proximal segment. The outer sheath is first retracted to deploy a portion of the midbody and the contralateral limb. Then, the front sheath is advanced distally to deploy the distal end of the graft. See e.g., U.S. Pat. No. 6,660,030. Other delivery systems, for example as disclosed in U.S. patent application Ser. No. 11/522,292, titled "A MULTI-SEGMENTED GRAFT DEPLOYMENT SYSTEM" and filed on Sep. 15, 2006 (the entirety of which is hereby incorporated by reference as if fully set forth herein) may use a plurality of axially spaced releasable restraint members temporarily connected by a pull wire to allow the distal main branch portion to be deployed before a proximal graft portion. Typically, these delivery systems are delivered to the aneurysm location over a guidewire. The guidewire may be further used to release a branch graft portion of the prosthesis, for example, by operably connecting a branch graft restraint mechanism to the guidewire and proximally withdrawing the guidewire from the vasculature.

Once the bifurcation graft has been deployed and implanted, a variety of procedures may desirably be accomplished. For example, it may be advantageous to implant a cuff on the proximal end of the main branch portion to secure the graft and thereby prevent movement or slippage of the main branch portion. Alternatively, it may be necessary to dilate the stenosis or touch up or re-establish the expansion of the graft. These procedures require advancing another catheter to the graft location along a guidewire. However, the positioning of a guidewire through the graft after the graft has been deployed is difficult since the tip of the guidewire will snag on the wire support cage of the graft. Thus, it may be advantageous to provide a guidewire assembly configured to remain placed through a graft once the graft has been deployed and to allow access through the expanded graft for subsequent catheterizations. Additionally, it may be advantageous to improve the configuration of the deployment catheter and/or the graft restraining members so as to improve the methods of deploying and positioning bifurcated and non-bifurcated grafts, as will be described herein.

As used herein, the relative terms "proximal" and "distal" shall be defined from the perspective of the delivery system. Thus, proximal refers to the direction of the control end of the delivery system and distal refers to the direction of the distal tip. In certain embodiments, the deployment catheter may be configured to deliver a graft that includes a main or distal graft portion and at least one branch or proximal graft portion. In certain embodiments, the hollow guidewire assembly may be associated with a restraint member for the branch segment, such that the branch segment may be deployed by the guidewire assembly. The guidewire assembly may be further configured such that it may be used to remove the restraint member from the branch segment while permitting placement and maintenance of a guidewire through the expanded branch segment and main body graft for subsequent catheterizations. Other embodiments of a graft deployment system and guidewire assembly will also be described below.

FIG. 1A is a schematic representation of an example of a bifurcated vascular prosthesis 50 that can be used with any embodiment of the deployment catheter disclosed herein, positioned at the bifurcation between the abdominal aorta and the right and left common iliac arteries. With reference to FIG. 1A, there is illustrated a schematic representation of the abdominal part of the aorta and its principal branches. In particular, the abdominal aorta 30 is characterized by a right renal artery 2 and left renal artery 4. The large terminal branches of the aorta 30 are the right and left common iliac arteries 37 and 38. Additional vessels (e.g., second lumbar, testicular, inferior mesenteric, middle sacral) have been omitted from FIG. 1A for simplification. One embodiment of an expanded bifurcated endoluminal vascular prosthesis is shown spanning aneurysms 103, 104 and 105. The expanded bifurcated endoluminal vascular prosthesis 50 can comprise a main branch portion 52 (also referred to herein as a main branch segment) for traversing the aorta, a first branch portion 54 (also referred to herein as a first branch segment or an ipsilateral branch portion) for spanning an ipsilateral iliac artery 37, and a second branch portion 56 (also referred to herein as a second branch segment or a contralateral branch portion) for spanning a contralateral iliac artery 38.

Note that the terms "first" and "second" branch portion can be used interchangeably and to refer to any branch vessel in the body, including but not limited to the ipsilateral vessel, the contralateral vessel, radial vessels, and subclavian vessels. Accordingly, in some embodiments, the "first" branch portion can refer to any branch portion including but not limited to the vessels set forth above. Similarly, the "second" branch portion can refer to any branch portion including but not limited to the vessels set forth above. In one embodiment, the first branch portion can refer to a downstream or upstream portion of a main branch vessel. For example, in one embodiment, the main branch portion and the first branch portion are configured to lie within at least a portion aortic arch (including, for example, the ascending and/or descending aorta) with main branch portion positioned closer to the heart while the second branch portion can be configured to extend into one of the branch vessels (left subclavian, right subclavian or carotid) that extend from the aortic arch.

Figure 1B:
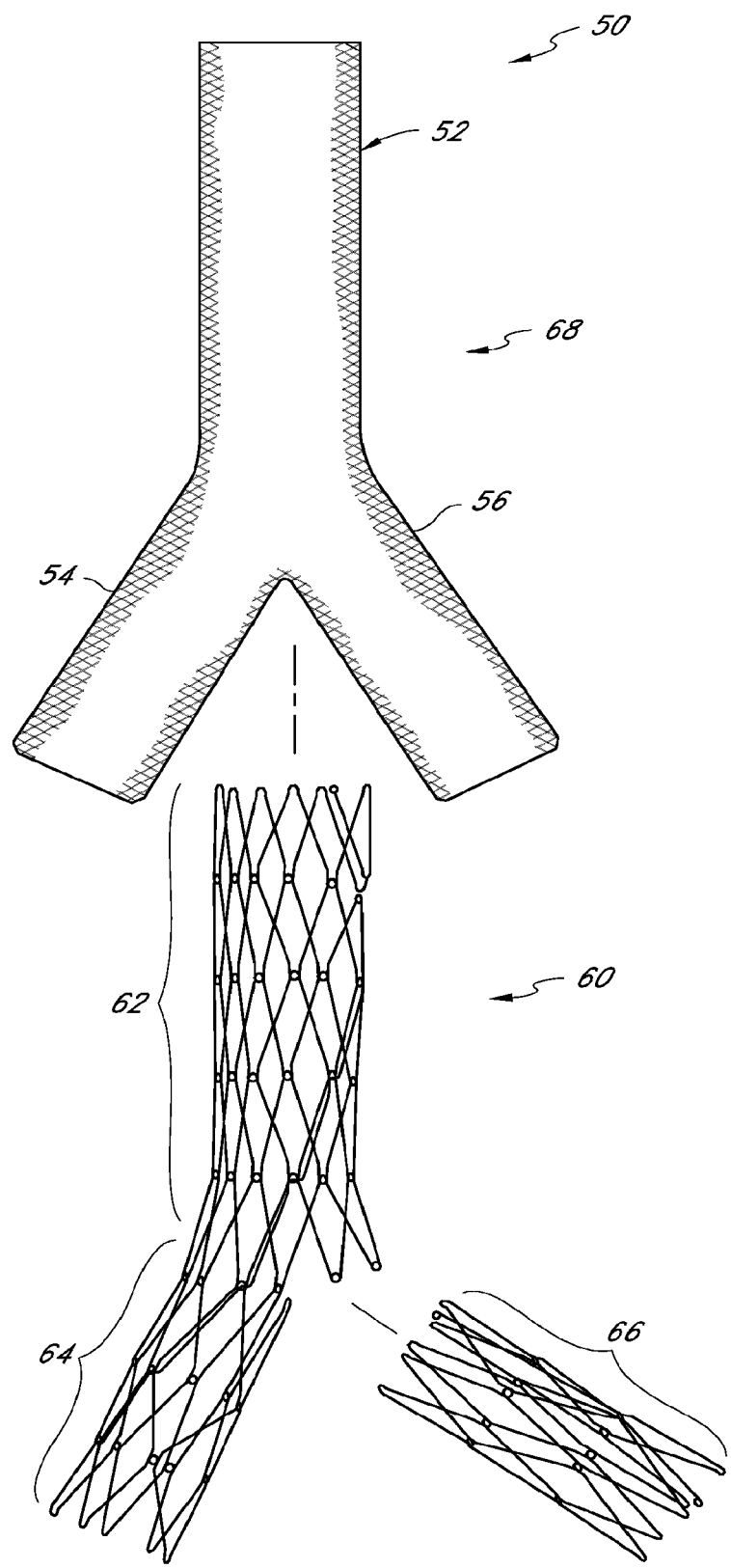
FIG. 1B is an exploded view of the bifurcated prosthesis of FIG. 1A, showing a self-expanding wire support cage separated from an outer polymeric sleeve.

FIG. 1B is an exploded view of the bifurcated prosthesis 50 of FIG. 1A, which can include a preferably self-expanding wire support (cage) 60 and an outer polymeric sleeve 68. In FIG. 1B, the wire support 60 is shown separated from an outer polymeric sleeve 68. In the illustrated embodiment, the polymeric sleeve 68 can be situated concentrically outside of the tubular wire support 60. However, other embodiments may include a sleeve positioned instead concentrically inside the wire support or positioned on both the inside and the outside of the wire support. Alternatively, the wire support may be embedded within a polymeric matrix or layer which makes up the sleeve. The sleeve 68 may be attached to the wire support 60 by any of a variety of suitable manners known to those skilled in the art.

The tubular wire support 60 can comprise a main branch portion 62 for traversing the aorta, a first branch portion 64 (also referred to herein as an ipsilateral branch portion) for spanning an ipsilateral iliac and a second branch portion 66 (also referred to herein as a contralateral branch portion) for spanning a contralateral iliac. The main branch portion 62 and first ipsilateral branch portion 64 can be formed from a continuous single length of wire having a proximal end, a distal end and a central lumen extending therebetween. Alternatively, the first ipsilateral branch portion 64 may be formed of one or more lengths of wire pivotably connected to the proximal end of the main branch portion 62. A second, contralateral branch portion 66 may be formed of one or more lengths of wire pivotably connected to the proximal end of the main branch portion 62. Each of the iliac branch components has a proximal end, a distal end and a central lumen extending therethrough. Construction of the graft from a three part cage conveniently facilitates the use of different gauge wire in the different components (e.g. 0.014 in. diameter main trunk and 0.012 in. diameter branch components).

In general, each of the components of the bifurcated endoluminal vascular prosthesis 50 may vary considerably in diameter, length, expansion coefficient, and other parameters or characteristics, depending upon the intended application. For implantation within the aorta of a typical adult, the main branch portion 52 will have a length within the range of from approximately 2 in. or less to approximately 5 in. or more, and, typically within the range of from approximately 3.5 in. to approximately 4 in. The unconstrained outside expanded diameter of the main branch portion 52 will typically be within the range of from approximately 0.75 in. to approximately 1.5 in. The unconstrained expanded outside diameter of the main branch portion 52 can be constant or substantially constant throughout the length, or can be tapered from a relatively larger diameter at the distal end to a relatively smaller diameter at the bifurcation. In general, the diameter of the proximal end of the main branch portion will be on the order of no more than approximately 95% and, preferably, no more than approximately 85% of the diameter of the distal end of the main branch portion. The iliac branch portions 54 and 56 will typically be bilaterally symmetrical, having a length within the range of from approximately 0.4 in. to approximately 2.6 in., and a diameter within the range of from approximately 0.04 in. to approximately 0.79 in.

The collapsed prosthesis for use in accordance with the present disclosure has a diameter in the range of approximately 0.08 in. to approximately 0.39 in. Preferably, the maximum diameter of the collapsed prosthesis is in the range of approximately 0.12 in. to approximately 0.24 in. (12 to 18 French). Some embodiments of the deployment catheter, including the prosthesis, can have a diameter in the range of from approximately 18 to approximately 20 or approximately 21 French. Other embodiments can have a diameter as low as approximately 19 French, approximately 16 French, approximately 14 French, or smaller. After deployment, the expanded endoluminal vascular prosthesis may radially self-expand to a diameter anywhere in the range of approximately 0.8 in. to approximately 1.6 in.

Although certain prosthesis configurations are disclosed herein, these are only examples of prostheses which are deployable using the embodiments of a deployment catheter and guidewire assembly described herein. In other embodiments, the delivery system described below may be used to deliver and deploy other types of self-expandable bifurcated or multi-segmented prosthesis having a main branch portion and at least one branch graft portion, as will be apparent to those of skill in the art in view of the disclosure herein. For example, in other embodiments, certain features and aspects of the deployment catheter and guidewire assembly can be used to deploy a graft without a branch graft portion, a graft with only one branch portion and/or a graft with more than one graft portions. Further details and additional embodiments of the prosthesis described above can be found in U.S. Pat. Nos. 6,007,296, 6,187,036, and 6,197,049, the entirety of which are hereby incorporated by reference herein.

It should also be appreciated that, although the illustrated embodiments are described in the context of a bifurcated graft configured for the abdominal aorta, certain features and aspects of the delivery systems and methods described herein can be used in other portions of the vascular system. For example, it is anticipated that certain features and aspects of the systems and methods described herein can be adapted for use in the thoracic aorta. Accordingly, in some embodiments, the deployment catheter 120 may be configured to treat defects that may include, but are not limited to, abdominal aortic aneurysms, subclavian aneurysms, and thoracic aortic aneurysms, to name a few. It is also anticipated that certain features and aspects of the system described herein may be adapted to deliver a single straight graft segment to the thoracic aorta or other vessels or arteries within the body.

The self-expandable bifurcation graft can be deployed at a treatment site with any of a variety of deployment catheters, as will be apparent to those of skill in the art. Any of the embodiments of the deployment catheters disclosed herein may comprise any of the materials, features, or other details of any deployment catheters suitable for deploying a self-expanding bifurcation graft known in the field, or in any of the embodiments disclosed in U.S. Pat. No. 6,090,128, U.S. Pat. No. 6,500,202, U.S. Pat. No. 6,660,030, U.S. patent application Ser. No. 11/522,292, titled "A MULTI-SEGMENTED GRAFT DEPLOYMENT SYSTEM" and filed on Sep. 15, 2006, and in U.S. patent application Ser. No. 11/623,022, titled "DUAL CONCENTRIC GUIDEWIRE AND METHODS OF BIFURCATED GRAFT DEPLOYMENT" and filed on Jan. 12, 2007. The entirety of the above-referenced patents and patent applications are hereby incorporated by reference in their entirety as if fully set forth herein.

Figure 2:
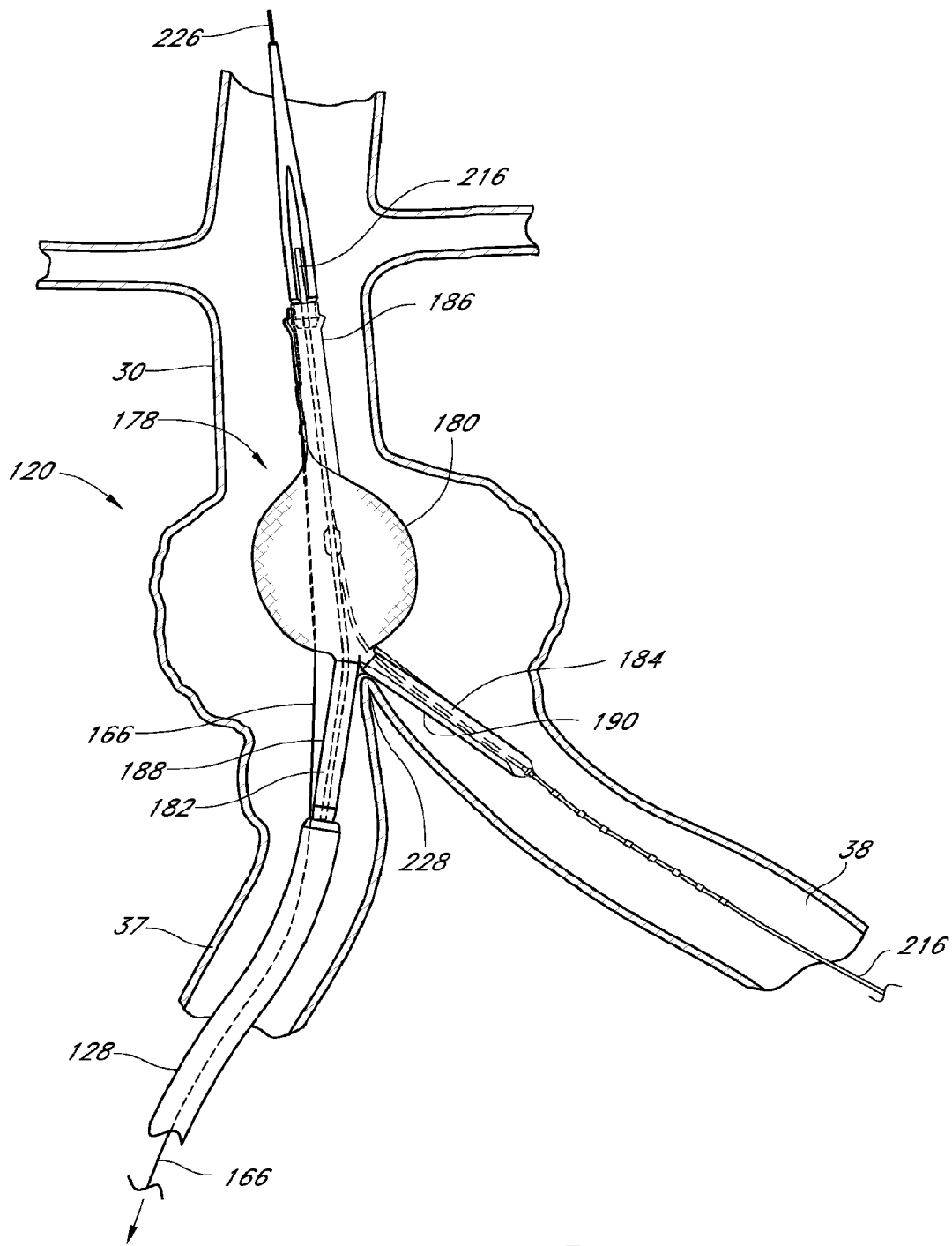
FIG. 2 is a schematic representation of an embodiment of the deployment catheter for delivering a bifurcated prosthesis, with a proximal portion of the main branch portion of the graft at least partially hidden in this deployed within the aorta.

With reference to FIG. 2, one method for using an embodiment of the deployment catheter 120 for treating an abdominal aortic aneurysm will be briefly described, without limitation. More detail regarding this deployment method will be described below. FIG. 2 is a schematic representation of an embodiment of a deployment catheter 120 for delivering a bifurcated prosthesis or graft 178, showing a proximal portion of the main branch portion 180 of the graft 178 at least partially deployed within the aorta for illustration purposes. As shown in FIG. 2, the deployment catheter 120 has preferably been introduced into a patient's vasculature through a puncture site in the patient's ipsilateral artery. The deployment catheter 120 is not limited to treatment of an abdominal aortic aneurysm, it can be configured to treat other aneurysms as discussed more fully herein. Additionally, depending on the clinical requirements, the deployment catheter 120 can be introduced into the patient's vasculature through puncture sites other than the ipsilateral artery. For example, without limitation, the deployment catheter 120 can be introduced into the patient's vasculature through the contralateral artery, through the radial artery, or through the subclavian artery.

As illustrated in FIG. 2, the deployment catheter 120 has preferably been advanced over a second guidewire 226 to the desired location within the patient's aorta. The graft 178 illustrated in FIG. 2 preferably comprises a main branch portion 180 constrained within a main branch sheath or member 186, an ipsilateral branch portion 182 constrained within and ipsilateral branch sheath or member 188, and a contralateral branch portion 184 constrained within a contralateral branch sheath or member 190. Prior to the deployment of the main branch portion 180 of the graft 178 as shown in FIG. 2, the entire graft was preferably constrained within an outer sheath 128 of the deployment catheter 120. In brief, the graft 178 was exposed by retracting the outer sheath 128, and the deployment catheter 120 was manipulated so as to position the contralateral branch portion 184 in the contralateral artery 38.

After positioning the graft 178 in the desired position, illustrated in FIG. 2, the main branch portion 180 of the graft 178 was deployed by retracting a sheath release wire 166, which caused the perforated main branch sheath 186 to tear along a side thereof. The remaining portion of the main branch portion 180 will preferably be deployed by further withdrawing the sheath release wire 166. In the illustrated embodiment, the contralateral branch portion 184 of the graft 178 will preferably be deployed by withdrawing the guidewire sheath 216 through a puncture site in the contralateral iliac artery 38, causing the contralateral branch sheath 190 to be withdrawn. The main branch sheath 186 is preferably also connected to the contralateral guidewire sheath 216 and is preferably withdrawn with the contralateral branch sheath 190. Similarly, in the final step in the deployment of the graft 178, the ipsilateral branch portion 182 of the graft 178 will preferably be deployed by withdrawing the deployment catheter 120 through a puncture site in the ipsilateral iliac artery 37, causing the ipsilateral branch sheath 188 to be withdrawn.

The deployment method described with reference to FIG. 2 is not intended to limit the applicability of the deployment catheter 120. The deployment catheter described herein may be configured to deploy a straight, bifurcated, or any other graft configuration into any portion of an artery or other blood vessel in the body. In some embodiments, the deployment catheter 120 may be used to deploy grafts having anchoring elements that help secure the graft to the vessel wall as well as grafts that do not have anchoring elements. With this brief, non-limiting overview of one method of using the deployment catheter 120 having been described, additional features and configurations of the deployment catheter 120 and additional details of this and other deployment methods will now be described.

Figure 3:
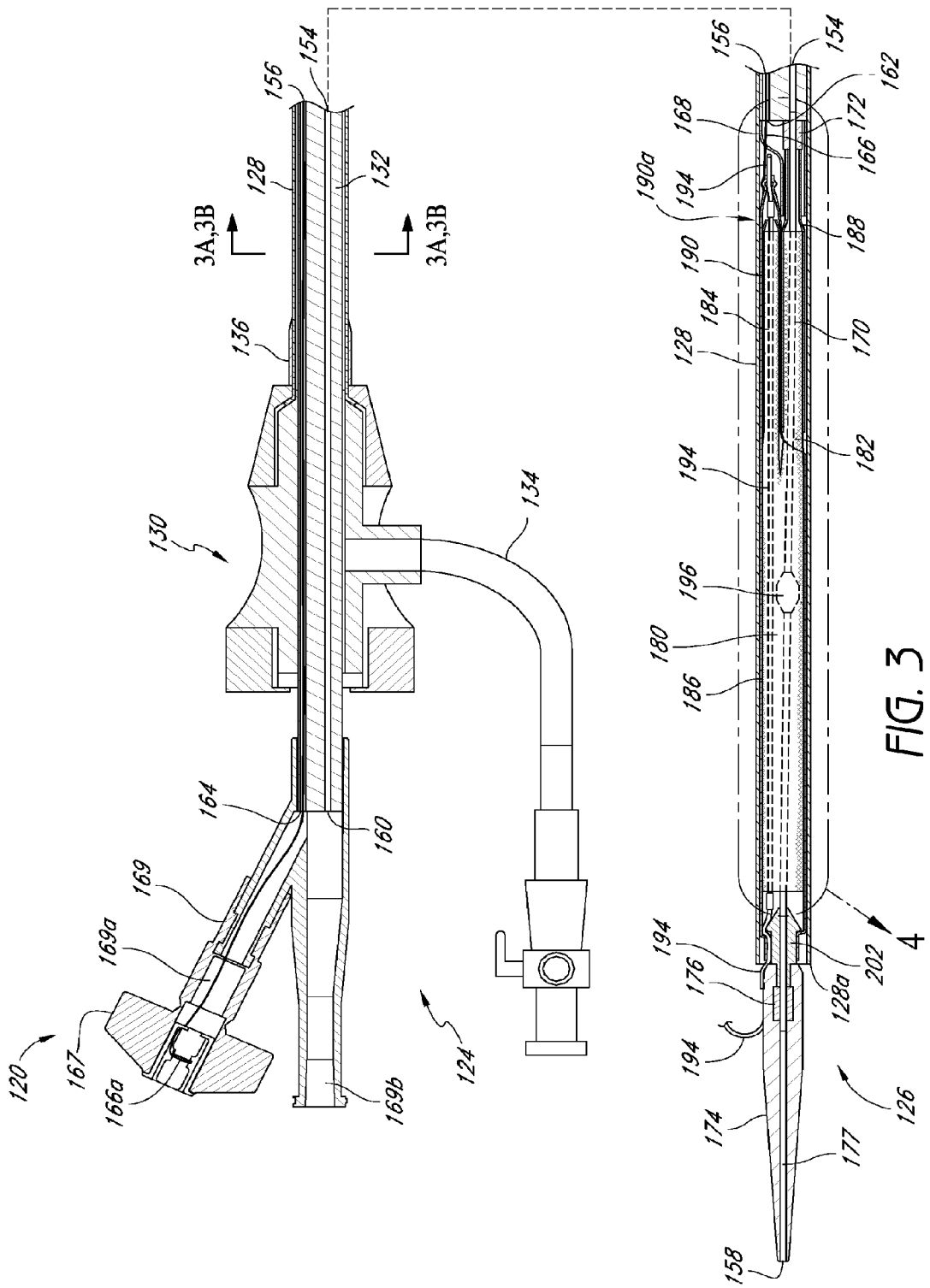
FIG. 3 is a cross-sectional view of an embodiment of a deployment catheter for delivering a bifurcated prosthesis.

FIG. 3 is a cross-sectional view of an embodiment of a deployment catheter 120 for delivering a bifurcated vascular prosthesis, such as but not limited to the prosthesis 50 described above. The deployment catheter 120 preferably comprises an elongate flexible, multi-component tubular body 122 having a proximal end 124 and a distal end 126. The tubular body 122 and other components of this system can be manufactured in accordance with any of a variety of techniques well known in the catheter manufacturing field. Suitable materials and dimensions can be readily selected taking into account the natural anatomical dimensions in the iliacs and aorta, together with the dimensions of the desired percutaneous access site.

In some embodiments, the elongate flexible tubular body 122 preferably comprises an outer sheath 128 that is preferably supported by a valve member 130. In the illustrated embodiment, the outer sheath 128 is preferably axially and radially supported by the valve member 130 so that the outer sheath 128 and valve member 130 translate and rotate in unison so that the rotation or translation of the valve member 130 preferably causes commensurate rotation or translation of the outer sheath 128. The tubular body 122 preferably also comprises a central inner core 132 that is preferably supported within the outer sheath 128 so as to be axially moveable within the outer sheath 128. Additionally, in some embodiments, as in the illustrated embodiment, a support sleeve 136 may be positioned adjacent to the valve member 130 and adhered or otherwise attached to the outside of the outer sheath 128 to provide additional stiffness or support to the outer sheath 128 adjacent to the valve member 130.

As mentioned above, the outer sheath 128 can comprise a valve member 130 at the proximal end of the outer sheath 128. In some embodiments, the valve member 130 preferably has a hemostatic valve 134 that can provide an access port for the infusion of drugs or contrast media as will be understood by those of skill in the art. In some embodiments, the outer tubular sheath 128 preferably comprises extruded PTFE, having an outside diameter of approximately 0.250 in. and an inside diameter of approximately 0.230 in. in some embodiments, the outer sheath 128 can have an outside diameter of between approximately 18 French and approximately 22

French. In some embodiments, the outer sheath 128 can be formed from PEBAX, nylon, polyethylene, or any other material that is suitable for endovascular delivery systems. In some embodiments, the outer sheath 128 is preferably a thin-walled, collapsible sheath. In some embodiments, the outer sheath 128 can comprise an inner liner, an outer layer, and an embedded metal braid or metal wire coil. In some embodiments, the inner liner can be comprised from PTFE or any other suitable material that preferably provides a low friction surface for passage of the inner core 132. The outer layer preferably formed from a soft, thin-walled plastic such as PEBAX, but can be made from any other suitable material. The outer layer is preferably formed from a material that is soft enough to permit the lumen of the outer sheath 128 to reopen after a kink or constriction has been formed in the outer sheath 128.

In some embodiments, the outer sheath 128 can be reinforced with a metal coil instead of the metal braid. The metal braid or coil can be formed from stainless steel, nitinol, or any other suitable material including, but not limited to, shape memory materials. In some embodiments, the sheath 128 preferably has sufficient memory to recoil from a collapsed position into a patent position such that any kinks in the outer sheath 128 are easily opened when the inner core 132, or other diagnostic or therapeutic catheter based devices known to the art, is passed through the outer sheath 128. As such, only a small force is preferably required to pass the inner core 132 through any portions of the outer sheath 128 that have become kinked or collapsed. In this configuration, the outer sheath 128 preferably provides a patent lumen suitable for highly tortuous anatomies where traditional outer sheath materials may kink or collapse.

In some embodiments, the liner preferably has a wall thickness less than or equal to approximately 0.002 in. However, in some embodiments, the liner can have a wall thickness from approximately 0.001 in. or less to approximately 0.003 in., or from approximately 0.003 in. to approximately 0.005 in. or more. In some embodiments, the metal braid or coil preferably has a thickness of less than or equal to approximately 0.002 in. However, in some embodiments, the metal braid or coil can have a wall thickness from approximately 0.001 in. or less to approximately 0.003 in., or from approximately 0.003 in. to approximately 0.005 in. or more. In some embodiments, the outer layer preferably has a wall thickness less than or equal to approximately 0.01 in. and a Durometer hardness value less than or equal to approximately 72 D. However, in some embodiments, the outer layer can have a wall thickness from approximately 0.005 in. to approximately 0.008 in., or from approximately 0.008 in. to approximately 0.011 in. or more, and a Durometer hardness value from approximately 55 D or less to approximately 65 D, or from approximately 65 D to approximately 75 D or more. However, the thickness, dimension, shape, hardness, and other aspects of the configurations of each of the materials comprising the outer sheath 128 are not limited to those described herein, but can be of any thickness, dimension, shape, or hardness suitable for endovascular delivery systems.

In some embodiments, the outer tubular sheath 128 preferably has an axial length within the range of from approximately 15 in. or less to approximately 22 in. or more. In one embodiment of the deployment catheter 120 having an overall length of 33 in., the axial length of the outer tubular sheath 128 is preferably approximately 15 in. and the outside diameter is preferably less than or equal to approximately 0.28 in. In some embodiments, the distal end 128*a* of the tubular sheath 128 may be located at least approximately 2 in. from the distal end of the distal tip 174 of the deployment catheter 120, in a prosthesis loaded configuration.

In some embodiments, as in the illustrated embodiment, the central inner core 132 is preferably axially and rotatably movable within the outer sheath 128. However, in some embodiments, the central inner core 132 may be rotationally fixed relative to the outer sheath 128. Rotational engagement can be accomplished in any of a variety of ways, normally involving complementary surface structures such as keys or splines on the associated components. For example, the central inner core 132 can be provided with a radially outwardly extending projection along a portion or all of its axial length. This projection would preferably be slidably received within a radially outwardly extending slot on the interior surface of the outer sheath 128. Alternatively, a radially inwardly extending projection on the outer sheath 128 or associated component can be received with an axially extending recess on the outer surface of the central inner core 132. Alternatively, any of a variety of non-round configurations for the central inner core 132 such as elliptical, ovular, triangular, square, polygonal, circular with flat sides, and the like, can be slidably received within a complementary-shaped aperture on or connected to the outer sheath 128.

Alternatively, in some embodiments the inner core 132 and the valve member 130 may define complementary flat surfaces or other features such as, but not limited to, those described above that prevent the inner core 132 from rotating relative to the valve member 130, while the inner lumen of the outer sheath 128 may be circular. Additionally, in some embodiments, the valve member 130 may be tightened around the outer surface of the inner core 132 so as to substantially prevent the inner core 132 from translating and/or rotating relative to the valve member 130.

Figure 3B:
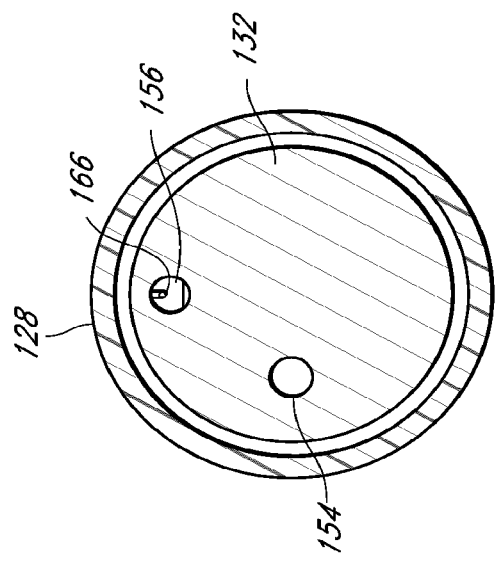
FIG. 3B is a cross-sectional view of an alternative of the embodiment of the deployment catheter shown in FIG. 3 taken along line 3B-3B of FIG. 3.
Figure 3A:
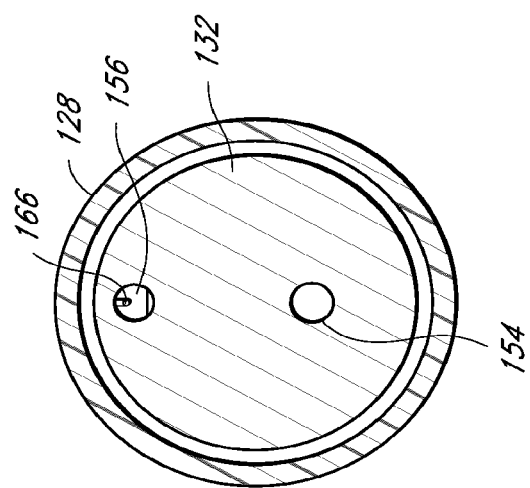
FIG. 3A is a cross-sectional view of the embodiment of the deployment catheter shown in FIG. 3 taken along line 3A-3A of FIG. 3.

FIG. 3A is cross-sectional view of the illustrated embodiment of the deployment catheter 120 taken along line 3A-3A of FIG. 3. As shown therein, in the illustrated embodiment, the cross-section of the central inner core 132 is preferably circular. However, in some embodiments as mentioned above, the cross-section of the central inner core 132 can deviate from a circular cross-section by the provision of one or two opposing flat sides extending axially along the length of the inner core 132. In the embodiments where the cross-section of the central inner core 132 deviates from a circular cross-section, an aperture with a corresponding cross-section may be provided in the outer sheath 128 and/or the valve member 130 such that the rotation of the outer sheath 128 or the valve member 130 will preferably cause a similar rotation of the central inner core 132.

With reference to FIGS. 3 and 3A, the inner core preferably comprises a guidewire lumen 154 and a sheath release lumen 156 extending longitudinally therethrough. In the illustrated embodiment, the guidewire lumen 154 preferably extends throughout the entire length of the tubular central core 132, having a distal exit port 158 and a proximal access port 160, as will be understood by those of skill in the art. In use, the deployment catheter 120 will preferably be advanced into position in the aorta over a guidewire extending through the guidewire lumen 154, as will be understood by those of skill in the art. A sheath release wire 166 (also referred to herein as a suture), which will be described in greater detail below, is preferably routed through the sheath release lumen 156. In the illustrated embodiment, the sheath release lumen 156 preferably extends through the entire length of the tubular inner (central) core 132, having a distal exit port 162 (shown most clearly in FIG. 4) and a proximal access port 164 (shown most clearly in FIG. 3), as will be understood by those of skill in the art.

In the embodiment of the deployment catheter 120 illustrated in FIG. 3A, the guidewire lumen 154 is preferably co-planar with the centerline axis of the inner core 132 and the sheath release lumen 156. However, this arrangement is not required. In some embodiments, as illustrated in FIG. 3B, which is a cross-sectional view of an alternative of the embodiment of the deployment catheter 120 shown in FIG. 3 taken along line 3B-3B of FIG. 3, the guidewire lumen 154 is preferably not coplanar with the centerline axis of the inner core 132 and the sheath release lumen 156. Therefore, as illustrated in FIG. 3B, the inner core 132 may be configured so that the guidewire lumen 154 and the sheath release lumen 156 are formed at any desired position in the cross-section of the inner core 132.

In the illustrated embodiment, the sheath release wire 166 is preferably attached to a tabbed handle 167 that is supported by a "Y" connector 169. In some embodiments, the handle 167 is configured to enable the user or medical practitioner to manipulate the sheath release wire 166. In some embodiments, the handle 167 is preferably removable from the "Y" connector 169 so that the medical practitioner or user can manipulate the handle 167 and, hence, the sheath release wire 166, independent of the "Y" connector 169. In some embodiments, the handle 167 may be threadedly and, hence, removably supported by the "Y" connector 169. In some embodiments, the handle 167 may be attached to, but configured to break away from, the "Y" connector 169 when the user or medical practitioner exerts a threshold force or to work on the handle 167 relative to the "Y" connector 169. In some embodiments, the handle 167 may be press fit into a complementary opening in the "Y" connector 169 so that the medical practitioner or user may remove the handle 167 from the "Y" connector 169 by pulling and/or turning the handle 167 relative to the "Y" connector 169.

The sheath release wire 166 preferably passes through a first port 169a in the "Y" connector 169 and so on through the sheath release lumen 156 as described above. The guidewire discussed above that can extend through the central guidewire lumen 154 can pass through a second port 169b in the "Y" connector 169. The "Y" connector 169 is preferably secured to the proximal end of the inner core 132 such as by thermal bonding, adhesive bonding, and/or any of a variety of other securing techniques known in the art.

An interface member 168 is preferably secured to the distal end of the inner core 132 such as by thermal bonding, adhesive bonding, and/or any of a variety of other securing techniques known in the art. The interface member 168 is preferably axially and rotationally secured to the inner core 132. The interface member 168 preferably axially and rotationally supports a central tube 170 so that the central tube 170 preferably cannot substantially rotate or translate axially relative to the inner core 132. In the illustrated embodiment, the central tube 170 preferably defines a lumen axially therethrough that is preferably axially aligned with the guidewire lumen 154 so that a guidewire that is advanced through the guidewire lumen 154 can also be advanced through the lumen of the central tube 170. A wire support 172 is preferably attached to the outside of the central tube 170 and supported by the interface member 168 to provide additional support to the central tube 170.

The tubing 170 may be formed from any suitable plastic or metal material, such as but not limited to stainless steel or nitinol, or any other material that is suitable for endovascular delivery systems. In some embodiments, the tubing 170 is preferably formed of braided metal so as to provide flexibility, tensile strength, and torsional strength. In some embodiments, the tubing 170 may be formed from multiple materials, including but not limited to being formed of a braided metal outer sheath that is lined with a plastic or other suitable material for support and/or to reduce frictional forces from a guidewire advanced therethrough.

A distal segment of the deployment catheter 120 preferably comprises an elongate, flexible tapered distal tip 174. In the illustrated embodiment, the distal tip 174 is preferably supported by the central tube 170. The distal tip 174 may over molded onto an anchor 176 that is secured to the outside surface of the central tube 170. Thus, in the illustrated embodiment, the distal tip 174 is preferably axially and rotationally supported on the central tube 170 so that the distal tip 174 is substantially prevented from any axial movement or rotation relative to the central tube 170. The central tube 170 is preferably configured to define a longitudinal opening therethrough, the longitudinal opening or lumen being preferably axially aligned with the guidewire lumen 154 such that a guidewire extending through the guidewire lumen 154 can also extend through the lumen in the central tube 170.

In the illustrated embodiment, the central tube 170 preferably protrudes into the distal tip 174 to a short distance beyond the location of the anchor 176. In some embodiments, however, at least a portion of the anchor 176 may extend all the way to the end of the distal tip 174, or beyond. In the illustrated embodiment, an aperture or opening 177 in the distal tip 174 is preferably axially aligned with the opening in the central tube 170, such that a guidewire passing through the opening in the central tube 170 may also pass through the opening 177 in the distal tip 174. In this configuration, the distal tip 174 is preferably substantially axially and rotationally fixed to the inner core 132 such that the axial and rotational positioning of the distal tip 174 can be controlled by the axial and rotational positioning of the inner core 132.

With reference to FIG. 3, the distal tip 174 preferably tapers from an outside diameter of approximately 0.225 in. at its proximal end to an outside diameter of approximately 0.070 in. at the distal end thereof. In some embodiments, the overall length of the distal tip 174 is approximately 2.5 in. However, the length and rate of taper of the distal tip 174 can be varied depending upon the desired trackability and flexibility characteristics, as well as other factors.

Figure 4:
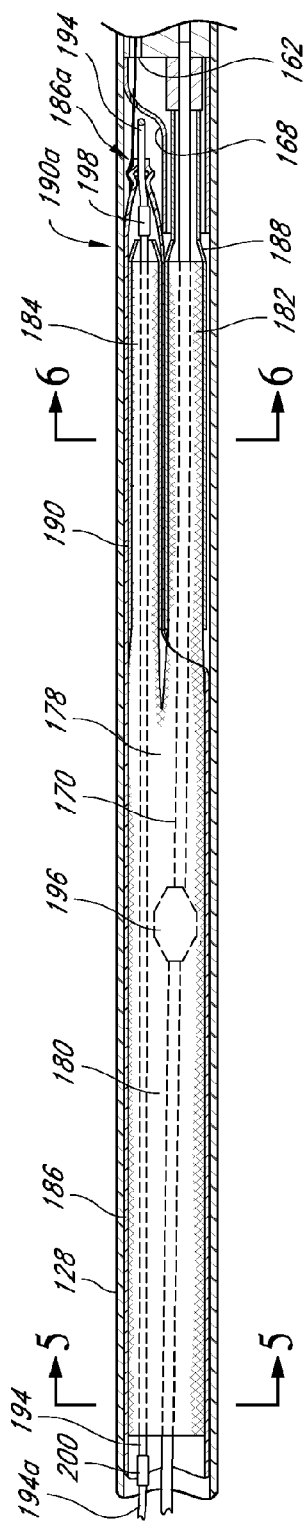
FIG. 4 is an enlargement of the portion delineated by the curve 4-4 in FIG. 3.
Figure 6:
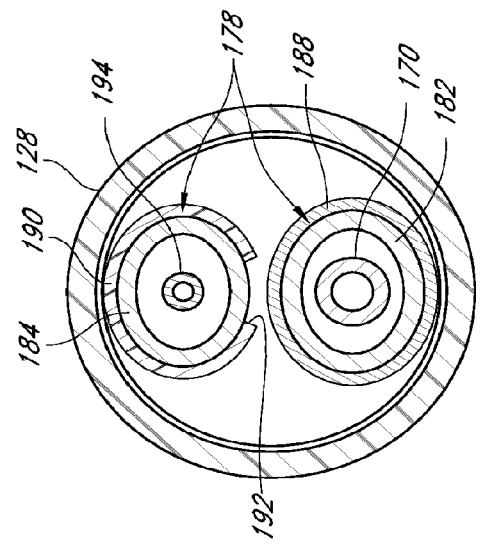
FIG. 6 is a cross-sectional view of the embodiment of the deployment catheter shown in FIG. 3 taken along line 6-6 of FIG. 4.
Figure 5:
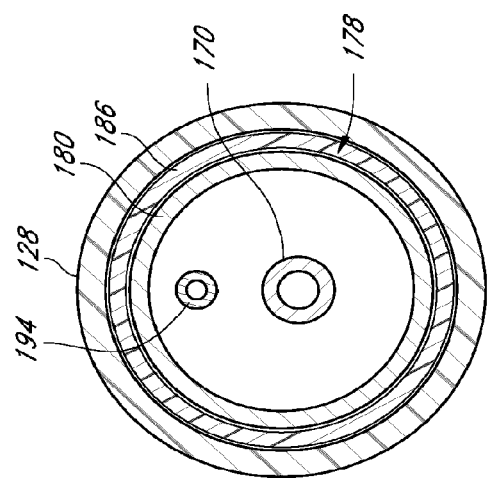
FIG. 5 is a cross-sectional view of the embodiment of the deployment catheter shown in FIG. 3 taken along line 5-5 of FIG. 4.

FIG. 4 is an enlargement of the portion delineated by the curve 4 in FIG. 3. FIGS. 5 and 6 are a cross-sectional view of the embodiment of the deployment catheter shown in FIG. 3 taken along line 5-5 and line 6-6, respectively, of FIG. 4. With reference to FIGS. 4-6, a bifurcated endoluminal graft 178 is illustrated in a compressed configuration within the deployment catheter 120, prior to the advancement of the inner core 132 relative to the other sheath 128. The graft 178 preferably comprises a distal aortic trunk or main branch portion 180, a proximal ipsilateral branch portion 182, and a proximal contralateral iliac portion 184. In the illustrated embodiment, the aortic main branch portion 180 of the graft 178 is preferably constrained within a main branch sheath 186. While the embodiment of main branch sheath 186 is shown with reference to compressing a main branch graft portion 180, it is envisioned that the main branch sheath 186 could alternatively be used to compress and deliver other portions of a multi-segmented vascular graft, such as a branch graft portion, the entire multi-segmented graft, or a single-segment, straight vascular graft. Further, in the illustrated embodiment, the ipsilateral branch portion 182 is preferably constrained with a preferably tubular ipsilateral branch sheath 188 (also referred to herein as the first branch sheath), and the contralateral branch portion 184 (also referred to herein as the second branch sheath) is preferably constrained within a preferably generally tubular contralateral branch sheath 190. In the illustrated embodiment, the ipsilateral branch sheath 188 and the contralateral branch sheath 190 are preferably open-ended tubular sheaths.

The ipsilateral branch sheath 188 preferably constrains substantially the entire length of the ipsilateral branch portion 182 of the bifurcated graft 178. Similarly, in the illustrated embodiment, the contralateral branch sheath 190 preferably constrains substantially the entire length of the contralateral branch portion 184 and of the bifurcated graft 178. However, in some embodiments, the ipsilateral branch sheath 188 and/or the contralateral branch sheath 190 may constrain substantially more or less than the entire length of the ipsilateral branch portion 182 or the contralateral branch portion 184, respectively, of the bifurcated graft 178.

With reference to FIG. 4, the main branch sheath 186 can be sized and configured to cover the entire length of the bifurcated graft 178. However, in some embodiments, the main branch sheath 186 is preferably configured to constrain only the length of the main branch portion 180 of the bifurcated graft 178. Thus, even though the main branch sheath 186 may extend to the distal end of the contralateral branch portion 184 of the graft 178, in some embodiments, the main branch sheath 186 is preferably configured so as to define a notch 192 along the portion of the length of the main branch sheath 186 that covers the contralateral branch portion 184. In some embodiments, the notch 192 can be a slit along a portion of the length of the main branch sheath 186. In some embodiments, as in the illustrated embodiment, the notch 192 preferably removes a portion of the main branch sheath 186 along a portion of the length of the main branch sheath 186 that can be less than or equal to approximately half of the perimeter of the main branch sheath 186. In some embodiments, the main branch sheath 186 can be skived to remove a suitable amount of the material comprising the main branch sheath 186 to allow the ipsilateral or contralateral branch portion 182, 184 of the graft 178 to deploy upon retraction of the outer sheath 128. Thus, in some embodiments, the main branch sheath 186 preferably does not constrain the ipsilateral or contralateral branch portion 182, 184 of the bifurcated endoluminal graft 178.

In some embodiments, as illustrated in FIG. 4, a torsion tab 196 is preferably integrally formed with the central tube 170, or secured thereto such as by thermal bonding, adhesive bonding, and/or any of a variety of other securing techniques known in the art. As is illustrated, the main branch portion 180 of the bifurcated endoluminal graft 178 is preferably constrained by the main branch sheath 186 around the torsion tab 196. In the illustrated embodiment, the torsion tab 196 preferably engages with the endoskeleton or, with reference to FIG. 1B, the wire support (cage) 60 of the bifurcated graft 178 and ensures that the bifurcated graft 178 substantially rotates with the inner core 132 of the deployment catheter 120. In other words, the torsion tab 196 preferably prevents the central tube 170 from rotating relative to the bifurcated graft 178. This preferably enhances the ability of the medical practitioner or user to rotate and, hence, maneuver, the graft 178 and the ipsilateral and/or contralateral branch portions 182, 184 within the patient's aorta by rotating the proximal end of the deployment catheter 120, in particular, by rotating the proximal end of the inner core 132 or the "Y" connector 169. As such, the torsion tab 196 preferably causes of the bifurcated endoluminal graft 178 to rotate substantially in unison with the central tube 170.

As will be discussed in greater detail, in some embodiments such as in the illustrated embodiment, the main branch sheath 186 will preferably be retracted through the contralateral iliac artery using a contralateral guidewire 194 after the main branch portion 180 of the bifurcated endoluminal graft 178 has been deployed. In some embodiments, the contralateral guidewire 194 preferably defines a lumen longitudinally therethrough, so that a smaller diameter guidewire can be advanced therethrough. Additionally, in some embodiments, the contralateral branch sheath 190 will preferably be deployed using the contralateral guidewire 194. The contralateral guidewire 194 and the constricted end portion 186a of the main branch sheath 186 are preferably configured so that the contralateral guidewire 194 is substantially permitted to slide through the opening in the constricted end portion 186a of the main branch sheath 186 while stops or tabs positioned on the guidewire 194 are prevented from sliding through constricted portion 186a.

Accordingly, in the illustrated embodiment, a tab 198 is preferably attached to the outside surface of the contralateral guidewire 194 such as by thermal bonding, adhesive bonding, and/or any of a variety of other securing techniques known in the art. The tab 198 is preferably positioned and configured such that, as the contralateral guidewire 194 slides through the constricted end portion 186a of the main branch sheath 186, the tab 198 is prevented from sliding through the constricted opening in the constricted end portion 186a of the main branch sheath 186. In this arrangement, with the main graft tab 198 abutted against the constricted end portion 186a of the main branch sheath 186, as the contralateral guidewire 194 is further retracted through the contralateral iliac artery, the main graft tab 198 will cause the main branch sheath 186 to also be retracted through the contralateral iliac artery. Additionally, a contralateral graft tab 200 is preferably positioned near to, or approximately adjacent to, the first end 194a of the contralateral guidewire 194 to engage and retract the contralateral branch sheath 190, as described in more detail below.

In the illustrated embodiment, the contralateral guidewire 194 is preferably approximately 160 cm. (63 in.) in length. In some embodiments, the contralateral guidewire 194 can be approximately 170 cm. (67 in.), or approximately 180 cm. (71 in.). Because the contralateral guidewire 194 is preferably positioned within or integrated into the deployment catheter 120 in the pre-deployment state, the contralateral guidewire 194 is preferably shorter than the conventional guidewires (e.g., the typical 300 cm. exchange length guidewires) that were typically inserted by the medical practitioner into a catheter for gaining access to, for example, the thoracic aortic region. In this configuration, a 0.014 in. guidewire may be advanced through the contralateral guidewire 194 and into the deep thoracic aortic region before (or after) the main branch portion 180 of the graft 178 is deployed. However, in any of the embodiments disclosed herein, the contralateral guidewire 194 may be configured so that a 0.018 in, or a 0.035 in., or any other suitable guidewire may be advanced therethrough. Accordingly, because the length of the contralateral guidewire 194 of this configuration can be short as 160 cm., the 0.014 in. guidewire that may be advanced through the contralateral guidewire 194 may similarly have a shorter length than the conventional guidewires that were used for this purpose. In the illustrated embodiment, a 0.014 in. guidewire having a length of approximately 180 cm. (71 in.) or 190 cm. (75 in.) may be used. However, the contralateral guidewire 194 and other guidewires disclosed herein can be formed in any suitable lengths and are not restricted to the dimensions disclosed herein.

The contralateral guidewire 194 preferably defines a first end (or also referred to as a distal end) 194a, as shown most clearly in FIG. 8, and a second end (or also referred to as a proximal end) 194b. In the illustrated embodiment, the second and 194b can be advanced through a puncture site in the patient's vasculature so that, when the delivery device 120 is positioned within the patient's vasculature, the second end 194b of the contralateral guidewire 194 is located outside of the patient's body and, hence, directly accessible by the medical practitioner or user. In some embodiments, as illustrated in FIG. 3, after the contralateral guidewire 194 passes away from the distal tip 174 through the main branch portion 180 and the contralateral branch portion 184 of the bifurcated graft 178, the guidewire 194 is preferably looped back around within the outer sheath 128 so as to be routed back toward the distal tip 174. In the illustrated embodiment, in the pre-deployment arrangement, the majority of the length of the guidewire 194 is preferably positioned outside of the deployment catheter 120, having exited the deployment catheter 120 between the distal end 128a of the tubular sheath 128 and the distal tip 174.

Figure 9:
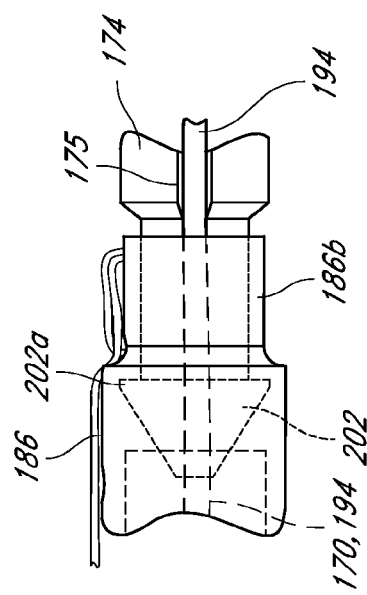
FIG. 9 is an enlarged detail view of FIG. 7 taken along the curve 9 in FIG. 7.

In the illustrated embodiment, as shown most clearly in FIG. 9, preferably linear grooves or depressions 175 can be formed in the distal tip 174 so that the contralateral guidewire 194 can pass between the distal tip 174 and the outer sheath 128 without substantially binding or obstructing the free axial movement of the distal tip 174 relative to the outer sheath 128. In the illustrated embodiment, both ends of the contralateral guidewire 194 are preferably arranged so as to pass between the distal tip 174 and the outer sheath 128 and are preferably positioned within the grooves or depressions 175 preferably formed in the distal tip 174.

Similarly, with reference to FIG. 12A, the contralateral guidewire 194 and the constricted end portion 190a of the contralateral branch sheath 190 are preferably configured so that the contralateral guidewire 194 is substantially permitted to slide through the opening in the constricted end portion 190a of the contralateral branch sheath 190. Accordingly, the tab 200 may be attached to the outside surface of the contralateral guidewire 194 such as by thermal bonding, adhesive bonding, and/or any of a variety of other securing techniques known in the art. The tab 200 is preferably positioned and configured such that, as the guidewire 194 slides through the constricted end portion 190a of the contralateral branch sheath 190, the tab 200 is prevented from sliding through the constricted opening in the constricted end portion 190a of the contralateral branch sheath 190. In this arrangement, with the contralateral graft tab 200 abutted against the constricted end portion 190a of the contralateral branch sheath 190, as the contralateral guidewire 194 is further retracted through the contralateral iliac artery, the contralateral graft tab 200 will cause the contralateral branch sheath 190 to also be retracted through the contralateral iliac artery. This will preferably cause the contralateral branch portion 184 of the graft 178 to be deployed.

Additionally, as is shown most clearly in FIG. 6, the central tube 170, the ipsilateral branch portion 182 of the bifurcated graft 178, and the ipsilateral branch sheath 188 are preferably offset within the outer sheath 128 from the centerline throughout a portion of the length deployment catheter 120. With reference to FIGS. 3A and 3B, the guidewire lumen 154 through which the central tube 170 preferably passes is also preferably offset within the inner core 132 to accommodate the offset of the central tube 170, the ipsilateral branch portion 182, and the ipsilateral branch sheath 188 from the centerline of that portion of the deployment catheter. Offsetting the central tube 170, the ipsilateral branch portion 182, and the ipsilateral branch sheath 188 provides more space within the outer sheath 128 for the contralateral guidewire 194, contralateral branch portion 184 of the bifurcated graft 178, the contralateral branch sheath 190, and the main branch sheath 186.

By offsetting the central tube 170, the ipsilateral branch portion 182, and the ipsilateral branch sheath 188 from the centerline of the deployment catheter, the radial forces exerted on the inside surface of the outer sheath 128 from the ipsilateral and contralateral iliac portions of the grafts and sheaths will preferably be reduced. Some of the results are, without limitation, that the ipsilateral and contralateral iliac portions of the grafts and sheaths will preferably be centered within the outer sheath, and the deployment forces will be reduced. In particular, in some embodiments, with the ipsilateral and contralateral iliac portions of the grafts and sheaths offset from the centerline of the deployment catheter 120, extending the inner core 132 relative to the outer sheath 128 will require less force than if not offset, and the compression forces on each of the branches and respective sheaths in the pre-deployment state will be reduced.

FIGS. 7 and 8 are a side view and top view, respectively, of the main branch sheath 186 (also referred to herein as a restraint member) of the embodiment of the deployment catheter 120 shown in FIG. 3, before the deployment of the main branch portion 180 of the graft 178. FIG. 9 is an enlarged detail view of FIG. 7 taken along the curve 9 in FIG. 7. With reference to FIGS. 7-9, the distal end 186b of the main branch sheath 186 is preferably tapered or constricted so as to define a smaller cross-sectional diameter or size as compared to the main body portion of the main branch sheath 186. The smaller diameter of the distal end 186b preferably ensures that the main branch sheath 186 will be secured around the distal anchor member 202 in a manner that will preferably prevent the main branch sheath 186 from moving or sliding relative to the distal anchor member 202. As such, the distal anchor member 202 preferably defines an annular protruding portion 202a that preferably substantially prevents the main branch sheath 186 from slipping relative to the distal tip 174. Additionally, in some embodiments, the distal anchor member 202 may comprise a linear groove or depression to accommodate the passage of the contralateral guidewire 194 (or, as explained below, one end of the guidewire sheath 216) that can pass between the distal anchor member 202 and the distal end portion 186b of the main branch sheath 186 in the pre-deployment state.

Any of the main branch sheath 186, the ipsilateral branch sheath 188, and the contralateral branch sheath 190 may be formed from balloon blown PEBAX, nylon, PET, PTFE, or any other suitable material. In some embodiments, the sheath material is preferably selected so as to increase the tensile strength of the sheath. Additionally, in some embodiments, the material selected to form any of the sheaths may be at least partially opaque or colored. This may be beneficial for any of the processing that the sheaths may undergo, such as, but not limited to, laser cutting, laser etching, perforating, drilling, threading with sutures, or any of the other processing steps disclosed herein. For example, many lasers that are commonly used for etching, cutting, perforating, or other procedures require the sheath material to be partially opaque for such laser processing.

Figure 10:
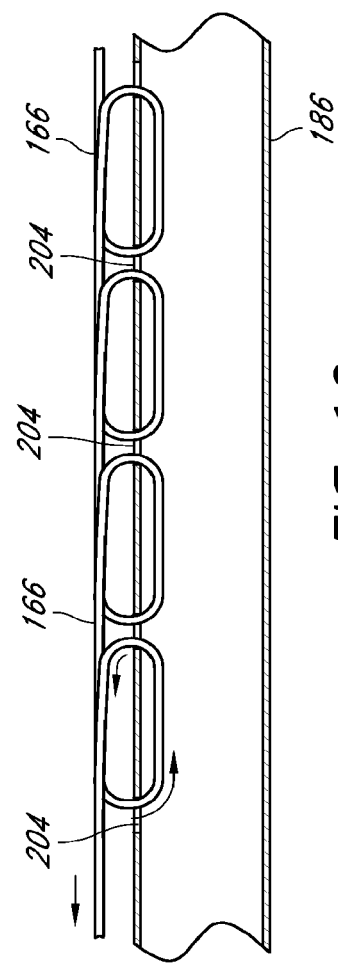
FIG. 10 is an enlarged section view through the axial centerline of the main branch sheath shown in FIG. 7 taken along the curve 10 in FIG. 7.

FIG. 10 is an enlarged section view through the axial centerline of the main branch sheath 186 shown in FIG. 7 taken along the curve 10 in FIG. 7. FIG. 11A is a cross-sectional view of the main branch sheath 186 shown in FIG. 7 taken along line 11A-11A of FIG. 7, and FIG. 11B is an enlarged detail view of FIG. 11A taken along the curve 11B in FIG. 11A. With reference to FIGS. 7-11B, additional detail regarding the main branch sheath 186 and the ipsilateral and contralateral branch portion sheaths 188, 190 will now be described. As previously discussed, in the illustrated embodiment, the main branch sheath 186 preferably partially or fully covers the entire length of the bifurcated graft 178, although the main branch sheath 186 may not cover the entire circumference of the graft 178 along the entire length of the graft 178. The notch 192 is preferably formed along the portion of the main branch sheath 186 that is approximately adjacent to the ipsilateral branch sheath 188. The notch 192 preferably allows the ipsilateral branch portion 182 of the bifurcated graft 178 to be manipulated away from the contralateral branch portion 184 of the bifurcated graft 178 before the main branch sheath 186 has been removed.

As discussed above, the portion of the main branch sheath 186 that preferably constrains the main branch portion 180 of the graft 178 is preferably generally tubular shaped, as shown most clearly in FIGS. 7, 8, and 11A. Perforations or openings 204 are preferably formed along one side of the main branch sheath 186. In some embodiments, as in the illustrated embodiment, the openings 204 are preferably linearly aligned. As will be described in greater detail below, the main branch portion 180 of the bifurcated graft 178 will preferably be deployed from the main branch sheath 186 by retracting sheath release wire 166 that is preferably threaded through each of the openings 204 as illustrated in FIG. 10, propagating a tear along the side of the main branch sheath 186 that has been perforated with the openings 204.

In the illustrated embodiment, the openings 204 are preferably spaced apart approximately 0.15 in. In some embodiments, the openings 204 may be spaced apart less than approximately 0.15 in., or from approximately 0.15 in. to approximately 0.2 in., or from approximately 0.2 in. to approximately 0.25 in. or more. In the illustrated embodiment, each of the openings 204 preferably has a circular shape and defines a diameter that is slightly larger than twice the diameter of the sheath release wire 166 passing therethrough. Additionally, with reference to FIG. 11C, which is an enlarged view of a portion of FIG. 8, each of the openings 204 preferably defines a cut-out or notch 208 formed in a portion of the periphery of each of the openings 204. In some embodiments, the notches 208 are configured to assist the propagation of a tear at each opening 204 when the sheath release wire 166 is withdrawn, as will be understood by one of ordinary skill in the art. In some embodiments, the openings 204 may be formed without any notches or cut-outs. In the illustrated embodiment, each of the notches 208 preferably defines a generally triangular shape. However, the shape of each notch 208 is not so limited, and can define any suitable shape.

However, the shape and the size of each opening 204 is not so limited. Each opening 204 may define any shape that is desired or configured to cause the main branch sheath 186 to tear along the perforated side (i.e., along the openings 204) of the main branch sheath 186. For example, without limitation, each opening may have a triangular, square, or diamond shape and may be larger or smaller than the sizes disclosed above. Additionally, with reference to FIG. 11B, in some embodiments, one or more score lines or depressions 206 may be formed on the inside or the outside surface of the main branch sheath 186 along the tear line (i.e., between each of the openings 204) to help propagate or progress a tear along the main branch sheath 186. In the illustrated embodiment, one or more of the openings 204 define a notch 208 formed in a portion of the opening 204, and a depression 206 has preferably been formed between one or more of the openings 204.

The sheath release wire 166 can be routed through the openings 204 in any of a number of suitable ways. As shown most clearly in FIG. 10, the sheath release wire 166 is preferably routed through the openings 204 in the illustrated embodiment of the main branch sheath 186 as described below. As most clearly shown in FIG. 3, the proximal end 166a of the sheath release wire 166 is preferably routed through the deployment catheter 120 so as to be accessible to the medical practitioner. In the illustrated embodiment, with reference to FIG. 3, the proximal end 166a of the sheath release wire 166 is preferably secured to the tabbed handle 167 so that the sheath release wire 166 can be manipulated by manipulating the preferably removable tabbed handle 167. Once the bifurcated graft 178 is in the desired position, as will be described in greater detail below, the sheath release wire 166 may be pulled or retracted by the medical practitioner to begin propagating tears in the main branch sheath 186, so as to begin deploying the main branch portion 180 of the graft 178. Further, portions of the main branch sheath 186 may define slits in the segments of the sheath 186 between one or more of the openings 204, such that the sheath 186 need not be torn at that portion. FIG. 11D is an enlarged detail view of FIG. 8 taken along the curve 11D in FIG. 8. With reference to FIG. 11D, in the illustrated embodiment, a slit 210 has preferably been formed near the distal end 186b of the main branch sheath 186, connecting three of the openings 204 formed near the distal end 186b of the sheath 186.

The sheath release wire 166 of the illustrated embodiment of the deployment catheter 120 can be routed through the openings 204 of the main branch sheath 186 as illustrated in FIGS. 7 and 8 such that the distal end 166b of the sheath release wire 166 is secured in a knot 212 positioned as shown in the referenced figures. With reference to FIG. 10, one suitable routing of the sheath release wire 166 through the openings 204 is illustrated. In the illustrated embodiment, with reference to FIG. 10, the sheath release wire 166 is preferably looped around the each segment of the sheath 186 between each of the openings (holes) 204 so as to pass through most openings 204 in the sheath 186 at least two times. In this configuration, as the sheath release wire 166 is pulled in the directions of the arrows shown in FIG. 10, each of the segments of the main branch sheath 186 between each of the openings 204 will be sequentially torn by the wire 166 such that the main branch portion 180 of the graft 178 adjacent thereto will be deployed. However, many other routings or configurations of the sheath release wire 166 and the openings 204 are anticipated. For example, without limitation, sheath release wire 166 may also be routed as disclosed in U.S. patent application Ser. No. 11/522,292 referenced above, which is fully incorporated herein by reference.

The main branch sheath 186 can be configured such that the main branch portion 180 of the bifurcated graft 178 can be deployed in a number of different ways. For example, in some embodiments, the main branch sheath 186 can be configured so that the main branch portion 180 can be deployed first at the distal end of the main branch portion 180 and then sequentially deployed toward the proximal end of the main branch portion 180. In some embodiments, the main branch sheath 186 can be configured so that the main branch portion 180 can be deployed first at the proximal end of the main branch portion 180 and then sequentially deployed toward the distal end of the main branch portion 180. Additionally, in some embodiments, the main branch sheath 186 can be configured such that the main branch portion 180 of the graft 178 can be deployed in any combination of deployment directions or sequences described herein or in any other suitable sequences for the deployment of the main branch portion 180.

For example, without limitation, the illustrated main branch sheath 186 is preferably configured so that, as the sheath release wire 166 is retracted, the deployment of the main branch portion 180 of the graft 178 begins at the proximal end of the main branch portion 180 and moves toward the distal end of the main branch portion 180. The tear along the openings 204 in the main branch sheath 186 will preferably be propagated by pulling on the sheath release wire 166 until the tear reaches the opening 204a (illustrated in FIGS. 7 and 8). At opening 204a, the sheath release wire 166 is preferably routed to the distal end 186b of the sheath 186 so as to bypass the openings 204 between the opening 204a and the distal end 186b of the sheath 186. At that point, the sheath release wire 166 is preferably looped back through the opening 204b (illustrated in FIGS. 7 and 8) so as to form a loop around the segment of the sheath 186 between the distal end 186b of the sheath 186 and the opening 204b. In this configuration, after the main branch sheath 186 has been torn open up to opening 204a, further retraction of the sheath release wire 166 will then preferably begin to propagate a tear from the distal end 186b of the sheath 186 toward the constricted end portion 186a of the sheath 186. In particular, further retraction of the sheath release wire 166 will next preferably propagate a tear along the segment of the sheath 186 between the distal end 186b of the sheath 186 and the opening 204b.

As will be described below, in the illustrated embodiment, the main branch portion sheath 186 and the sheath release wire 166 have preferably been configured so that the knot 212 formed at the distal end 166b of the sheath release wire 166 is not positioned adjacent to or aft of the distal end 186b of the main branch sheath 186. Positioning the knot 212 fore of the distal end 186b preferably prevents the knot 212 from getting caught or snagged on the distal end of the main branch portion 180 of the graft 178 after the distal end of the main branch portion 180 of the graft 178 has been deployed. In some embodiments, however, the knot 212 can be positioned adjacent to or distal to the distal end 186b of the main branch sheath 186, or in any other desired or suitable location. For example, without limitation, knot 212 can be positioned adjacent to the distal end of the notch 192 formed in the main branch sheath 186, or at any location between the distal end of the notch 192 and the aft distal end 186b of the main branch sheath 186.

Additionally, in some embodiments, the sheath release wire 166 and inner core 132 may be configured and routed as will be understood by one of ordinary skill in the art so that, after the release wire 166 has caused the sheath 186 to be split and the main branch portion 180 of the graft 178 deployed, further retraction of the release wire 166 will withdraw the main branch sheath 186 partially or fully toward or into the ipsilateral iliac artery.

With reference to FIG. 11D, because a slit 210 has preferably been formed between the openings 204b and 204c, after the segment of the sheath 186 between the distal end 186b of the sheath 186 and the opening 204b has been torn, the distal end of the main branch portion 180 of the graft 178 (i.e., the portion of the main branch portion 180 of the graft 178 adjacent to and distal to the opening 204c) will preferably be substantially deployed. Further retraction of the sheath release wire 166 will preferably propagate a tear in the section of main branch sheath 186 between the opening 204c and the proximal end 186a of the sheath 186. In the illustrated embodiment, the final segment of the sheath 186 that will be torn is preferably the segment of the sheath 186 between the openings 204d and 204a. Note that, as the segment of the sheath 186 between the openings 204d and 204a is torn by further retraction of the wire 166, the main branch portion 180 of the graft 178 will be substantially fully deployed, and the knot 212 formed near the distal end 166b of the branch release wire 166 will preferably be retracted by the medical practitioner away from the main branch portion 180 of the bifurcated graft 178.

As will be more fully described below, proximal retraction of the outer sheath 128 relative to the inner core 132 distal interface of the inner core 132 relative to the outer sheath 186 will preferably release the compressed iliac branches 182 and 184 of the graft 178 so that they are no longer constrained within the outer sheath 128. The iliac branches 182 and 184 will preferably remain compressed and constrained within the ipsilateral and contralateral branch portion sheaths 188, 190, respectively, until the branch sheaths 188, 190 are removed. As mentioned, in the illustrated embodiment, the ipsilateral branch sheath 188 is preferably configured to constrain the ipsilateral branch portion 182 of the graft 178 in the constrained configuration, for implantation at the treatment site. The ipsilateral branch sheath 188 is preferably connected to the inner core 132 or the interface member 168 and is adapted to be axially proximally withdrawn from the ipsilateral branch portion 182 of the graft 178, thereby permitting the ipsilateral branch portion 182 to expand to its implanted configuration. In one embodiment, without limitation, the ipsilateral branch sheath 188 preferably comprises a thin walled PTFE extrusion having an outside diameter of approximately 0.215 in. and an axial length of approximately 2 to approximately 3 in. A proximal end of the ipsilateral branch sheath 188 can be necked down such as by heat shrinking to secure the ipsilateral branch sheath 188 to the interface member 168. Similarly, a distal portion of the interface member 168 can flare outwardly to provide a better securement for the ipsilateral branch sheath 188. In this manner, proximal withdrawal of the inner core 132 (preferably after the main branch portion 180 of the bifurcated graft 178 has been deployed) will in turn preferably proximally retract the ipsilateral branch sheath 188 away from the main branch portion 180 of the graft 178, thereby deploying the preferably self-expandable ipsilateral branch portion 182 of the graft 178. Because the ipsilateral branch sheath 188 is preferably a tubular sheath with an open end, the ipsilateral branch portion 182 of the graft 178 will preferably be deployed in a top-down direction (i.e., the portion of the ipsilateral branch portion 182 closest to the main branch portion 180 will preferably be the first portion to deploy).

In the illustrated embodiment, the main branch sheath 186 and the contralateral branch sheath 190 are preferably connected to the contralateral guidewire 194, as described above. The contralateral branch sheath 190 is preferably adapted to restrain the contralateral branch portion 184 of the graft 178 in the reduced or constrained state. In some embodiments, the contralateral branch sheath 190 preferably has an outside diameter of approximately 0.215 in. and an axial length of approximately 2 to approximately 3 in. In the illustrated embodiment, the contralateral branch sheath 190 can have a smaller cross-section than the ipsilateral branch sheath 188, due to the smaller diameter of the contralateral guidewire 194 positioned on the inside of the constrained contralateral branch portion 184 of the graft 178 as compared to the diameter of the central tube 170 positioned on the inside of the constrained ipsilateral branch portion 182 of the graft 178. Proximal retraction of the contralateral guidewire 194 through the contralateral iliac artery preferably proximally withdraws the contralateral branch sheath 190 from the contralateral graft branch portion 184, thereby deploying the contralateral graft portion 184.

FIG. 12A is a schematic representation of the dual concentric guidewire assembly of the embodiment of the deployment catheter 120 shown in FIG. 3, showing the position of the main branch sheath 186 and the contralateral branch sheath 190 before deployment of the main branch portion 180 of the graft 178. FIG. 12B is an enlarged detail view of FIG. 12A taken along the curve 12B in FIG. 12A. With reference to FIGS. 12A and 12B, in some embodiments, the contralateral guidewire 194 may be a dual concentric guidewire assembly 214 comprising a hollow guidewire sheath 216 and an inner core wire 218 that can be axially advanced through a central lumen 220 in the guidewire sheath 216. The length of the hollow guidewire sheath 216 can be the same as is disclosed for the contralateral guidewire 194 described above, or any other suitable length. Any reference herein the guidewire assembly 214 can be interpreted as a reference to the guidewire 194, since both can be used interchangeably As previously discussed, in some embodiments, as illustrated in FIGS. 12A and 12B, the preferably annular tab 198 may be attached to the outside surface of the hollow guidewire sheath 216 such that, in use, proximal retraction of the hollow guidewire sheath 216 preferably causes the tab 198 to engage the main graft sheath 186 so that the main graft sheath 186 can be retracted through the contralateral iliac artery after deployment of the main branch portion 180 of the graft 178. As most clearly shown in FIG. 12B, the main branch sheath 186 may be formed around an annular ring 222 through which the guidewire sheath 216 preferably passes. The ring 222 preferably helps to prevent the tab 198 from passing through the proximal end 186*a* of the main branch sheath 186 so that the main branch sheath 186 can be engaged when the guidewire sheath 216 is retracted.

Additionally, as mentioned above, the preferably annular tab 200 may be attached to the outside surface of the hollow guidewire sheath 216 such that, in use, further proximal retraction of the hollow guidewire sheath 216 preferably causes the tab 200 to engage the contralateral branch sheath 190 so that the contralateral branch portion 184 of the graft 178 can be deployed, and so that the contralateral branch sheath 190 can be retracted through the contralateral iliac artery. In some embodiments, the contralateral branch sheath 190 may be formed around a ring similar to ring 222 described above to preferably further prevent the tab 200 from passing through the proximal constricted end portion 190*a* of the contralateral branch sheath 190 so that the contralateral branch sheath 190 can be engaged when the guidewire sheath 216 is retracted. Because the contralateral branch sheath 190 is preferably a tubular sheath with an open end, the contralateral branch portion 184 of the graft 178 will preferably be deployed in a top-down direction (i.e., the portion of the contralateral branch portion 184 closest to the main branch portion 180 will preferably be the first portion to deploy).

As shown in FIG. 12A, in the pre-deployment arrangement, the main branch sheath 186 is preferably configured so as to at least partially surround the contralateral branch sheath 190. The tab 198 is preferably positioned on the guidewire sheath 216 approximately adjacent to, but between the proximal distal end 186*a* of the main branch sheath 186 and the proximal constricted end portion 190*a* of the contralateral branch sheath 190. In this configuration, any retraction of the guidewire sheath 216 will preferably cause retraction of the main branch sheath 186 before the contralateral branch sheath 190 is retracted.

Figure 15:
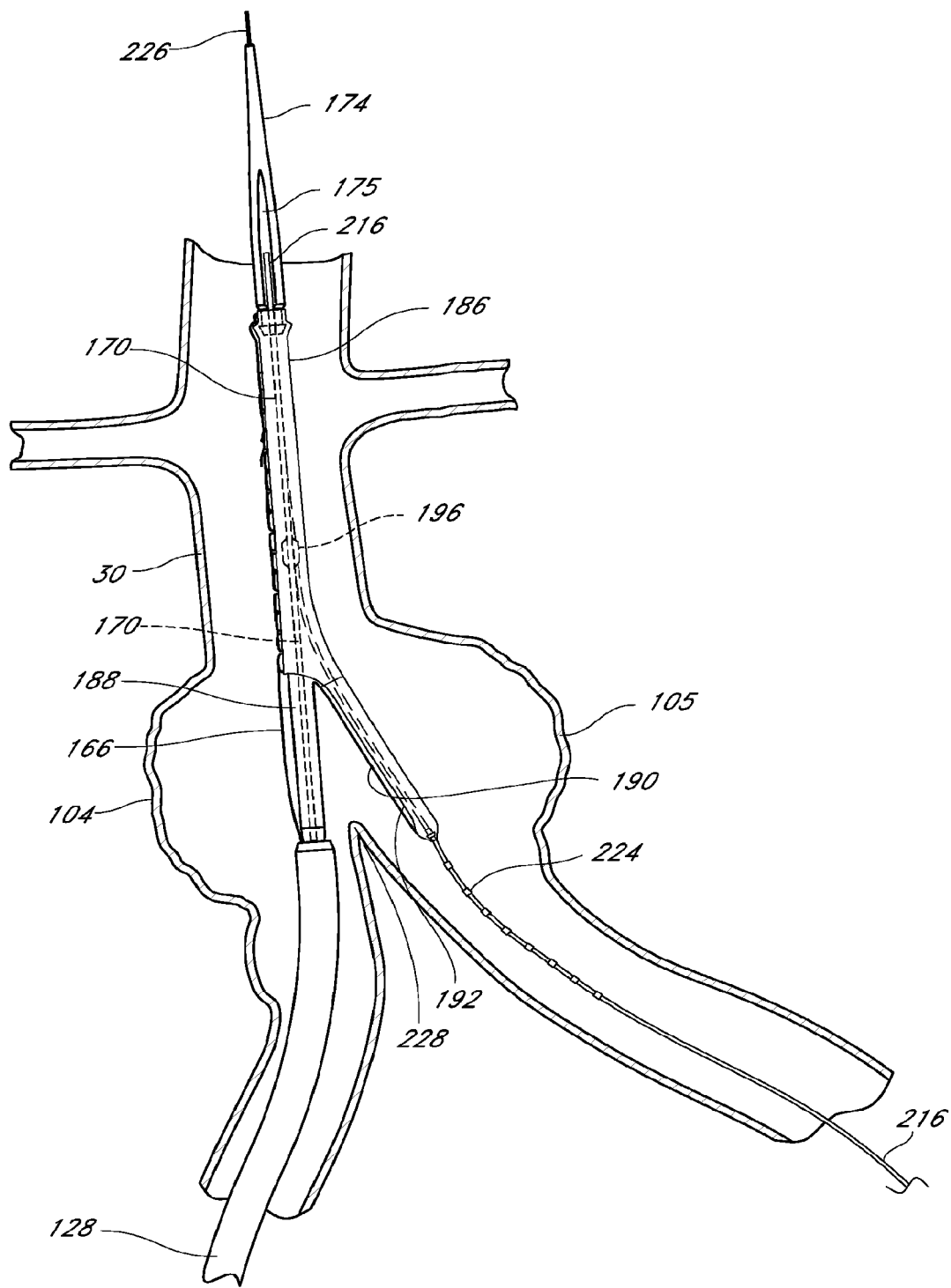
FIG. 15 is a schematic representation, as in FIG. 14, with the compressed iliac branches of the graft positioned partly within the iliac arteries.

In the loaded or pre-deployment state, the guidewire sheath 216 is preferably positioned within the main branch portion 180 of the graft 178 such that the distal end 216*a* of the guidewire sheath 216 extends beyond the distal end of the main branch portion 180 of the graft 178. As is shown most clearly in FIG. 15, in some embodiments, the distal end 216*a* of the guidewire sheath 216 preferably passes between the distal tip 174 and the outer sheath 128 within a depression 175 preferably formed in the distal tip 174. In this configuration, as shown in FIG. 15, a 0.014 in. guidewire may be advanced through the guidewire sheath 216 and into deep thoracic aortic region before (or after) the main branch portion 180 of the graft 178 has been deployed.

Additionally, as mentioned above, the contralateral branch tab 200 is preferably positioned near the distal end 216*a* of the guidewire sheath 216 at a distance away from the main branch tab 198 that is approximately greater than the overall length of the main branch sheath 186. In this configuration, the main branch sheath 186 will preferably be substantially completely retracted so that the distal end 186*b* of the main branch sheath 186 is approximately adjacent to or below (i.e., closer to the contralateral artery puncture site) relative to the proximal constricted end portion 190*a* of the contralateral branch sheath 190. This configuration will preferably prevent the main branch sheath 186 from becoming caught or snagged by the contralateral branch portion 184 of the graft 178 when the contralateral branch portion 184 is deployed. This configuration will also preferably reduce the forces that may be induced on the contralateral iliac artery and other portions of the anatomy during the retraction of the main branch sheath 186 or during the deployment of the contralateral branch portion 184.

In some embodiments, the main graft tab 198 is preferably spaced apart from the contralateral graft tab 200 by a distance that is approximately equal to or greater than the length of the main branch sheath 186. In some embodiments, the main graft tab 198 is preferably spaced apart from the contralateral graft tab 200 by more than approximately 0.5 in. or, alternatively, 0.75 in., less than the approximate length of the main branch sheath 186. In the illustrated embodiment, where the main branch restraint is approximately 7.25 in. in length, the main graft tab 198 is preferably spaced apart from the contralateral graft tab 200 by at least approximately 6.75 in. Further, in the illustrated embodiment, the contralateral graft tab 200 is preferably spaced apart from the distal end 216*a* of the guidewire sheath 216 by approximately 0.75 in. In some embodiments, the main graft tab 198 may be spaced apart from the contralateral graft tab 200 by approximately 6.75 to approximately 7.5 in. or more. Further, in the illustrated embodiment, the contralateral graft tab 200 may be spaced apart from the distal end 216*a* of the guidewire sheath 216 by approximately 1 in. or more.

FIG. 12C is a schematic representation of the dual concentric guidewire assembly 214 of the embodiment of the deployment catheter 120 of FIG. 3, showing the position of the main branch restraint member 186 and the contralateral branch restraint member 190 after the main branch portion 180 of the graft 178 has been deployed. FIG. 12C illustrates a desired position of the main graft tab 198 relative to the contralateral graft tab 200 for the illustrated embodiment of the deployment catheter 120. Accordingly, FIG. 12C illustrates a desired position of the main branch sheath 186 relative to the contralateral branch sheath 190 as both sheaths 186, 190 are being retracted by the guidewire sheath 216 and the main and contralateral graft tabs 198, 200.

As discussed above, the contralateral guidewire assembly 214 can be configured to retract or withdraw the main branch sheath 186 after the main branch portion 180 of the graft 178 has been deployed by retraction of the sheath release wire 166. In some embodiments, however, the contralateral guidewire assembly 214 may be used in place of the sheath release wire 166 to deploy the main branch sheath 186. For example, without limitation, in some embodiments, the contralateral guidewire assembly 214 may be configured to exert a sufficient axial force on the main branch sheath 186 to cause the main branch sheath 186 to tear along a perforated or scored edge of the main branch sheath 186, whether or not the sheath release wire 166 has been routed through the openings 204 in the main branch sheath 186. In these configurations, the contralateral guidewire assembly 214 may provide a parallel or redundant means for tearing the main branch sheath 186 and deploying the main branch portion 180 of the graft 178 where the sheath release wire 166 has either not been provided or has become damaged or failed.

In some embodiments, the length of the hollow guidewire sheath 216 may be from approximately 31 in. to approximately 65 in., or alternatively between approximately 35 in. to approximately 55 in. In some embodiments, the length of the hollow guidewire sheath 216 may be approximately 62 in., or alternatively approximately 54 in. In some embodiments, the axial length of the hollow guidewire sheath 216 is preferably sufficient to extend from a point outside of the body through an ipsilateral iliac puncture across the bifurcation between the contralateral and ipsilateral iliacs to a second point outside the body through a contralateral access site. Thus, the length of the hollow guidewire sheath 216 can vary depending upon the intended access site location along the femoral artery and the desired length of the guidewire sheath 216, which is preferably sized and configured to extend outside of the body, as illustrated most clearly in FIG. 13 discussed below.

The hollow guidewire sheath 216 may be formed in any of a variety of manners which are well known in the art of catheter body manufacturing, such as by braiding and/or extrusion. In the illustrated embodiment, the hollow guidewire sheath 216 is preferably made of a multi-filar wire Nitinol, although any other suitable flexible material may be used and is anticipated herein. Other suitable extrudable materials may include high density polyethylene, medium density polyethylene and other polyethylene blends, nylon, PEBAX, and others well known in the art. Reinforced tubular bodies may be produced by including a braided layer in or on the wall. The braided wall may comprise any of a variety of materials such as stainless steel, Nitinol, composite fibers and others known in the art. Additionally, in some embodiments, the hollow guidewire sheath 216, tabs 198, 200, ring 222, or other components or features on or adjacent to the hollow guidewire sheath 216 or other components of the deployment catheter 120 may further be provided with one or more radiopaque markers 224, such as a gold marker, to facilitate visualization during placement.

In some embodiments, the hollow guidewire sheath 216 preferably comprises a PEBAX extrusion, having a braided wire for reinforcing the lumen. The braid filament preferably comprises a round wire having a cross section of approximately 0.002 in. Alternatively, the hollow guidewire sheath 216 may comprise a stainless steel coil covered by a polyimide tubing that may be covered by PTFE heatshrink. The outer diameter of the hollow guidewire sheath 216 is preferably between approximately 0.025 in. and approximately 0.045 in., alternatively between approximately 0.020 in. and approximately 0.040 in. In some embodiments, the outer diameter of the hollow guidewire sheath 216 is preferably approximately 0.035 in.

As mentioned, in the illustrated embodiment, the hollow guidewire sheath 216 preferably comprises a central lumen 220 extending from the distal end to the proximal end such that the inner core wire 218 may be axially advanced through the central lumen 220. In some embodiments, the central lumen 220 preferably has an inner diameter of between approximately 0.020 in. and approximately 0.016 in., alternatively between approximately 0.019 in. and approximately 0.017 in., in one implementation approximately 0.018 in. such that an inner core wire 218 preferably having a diameter of no more than approximately 0.016 in. can be axially advanced therethrough.

The inner core wire 218 may, in the illustrated embodiment 014 in. guidewire. In other embodiments, the inner core wire 218 may be a 0.018 in. or a 0.035 in. guidewire, or any other suitable guidewire. In some embodiments, the inner core wire 218 can comprise any of a variety of structures, including polymeric monofilament materials, braided or woven materials, metal ribbon or wire, or conventional guidewires as are well known in the art. The inner core wire may have a length of between approximately 59 in. (150 cm.) or less to approximately 142 in. (360 cm.), alternatively between approximately 71 in. (180 cm.) to approximately 134 in. (340 cm.), alternatively between approximately 86 in. (220 cm.) to approximately 118 in. (300 cm.).

For example, in certain embodiments, the inner core wire 218 may be approximately 75 in. (190 cm.), approximately 95 in. (242 cm.), or approximately 118 in. (300 cm.). In general, the length of the inner core wire 218 is preferably between approximately 1.5 to approximately 3 times the length of the hollow guidewire sheath such that in use, positive contact may be maintained with the inner core wire 218 while the hollow guidewire sheath 216 is being withdrawn from a patient over the inner core wire 218. Positive contact with the inner core wire 218 will prevent friction between the inner core wire 218 and the hollow guidewire sheath 216 from inadvertently withdrawing the inner core wire 218 while refracting the as the hollow guidewire. Any of the dimensions, materials, or configurations disclosed herein can be varied widely as will be appreciated by those of skill in the art in view of the desired performance characteristics and manufacturing techniques.

Figure 13:
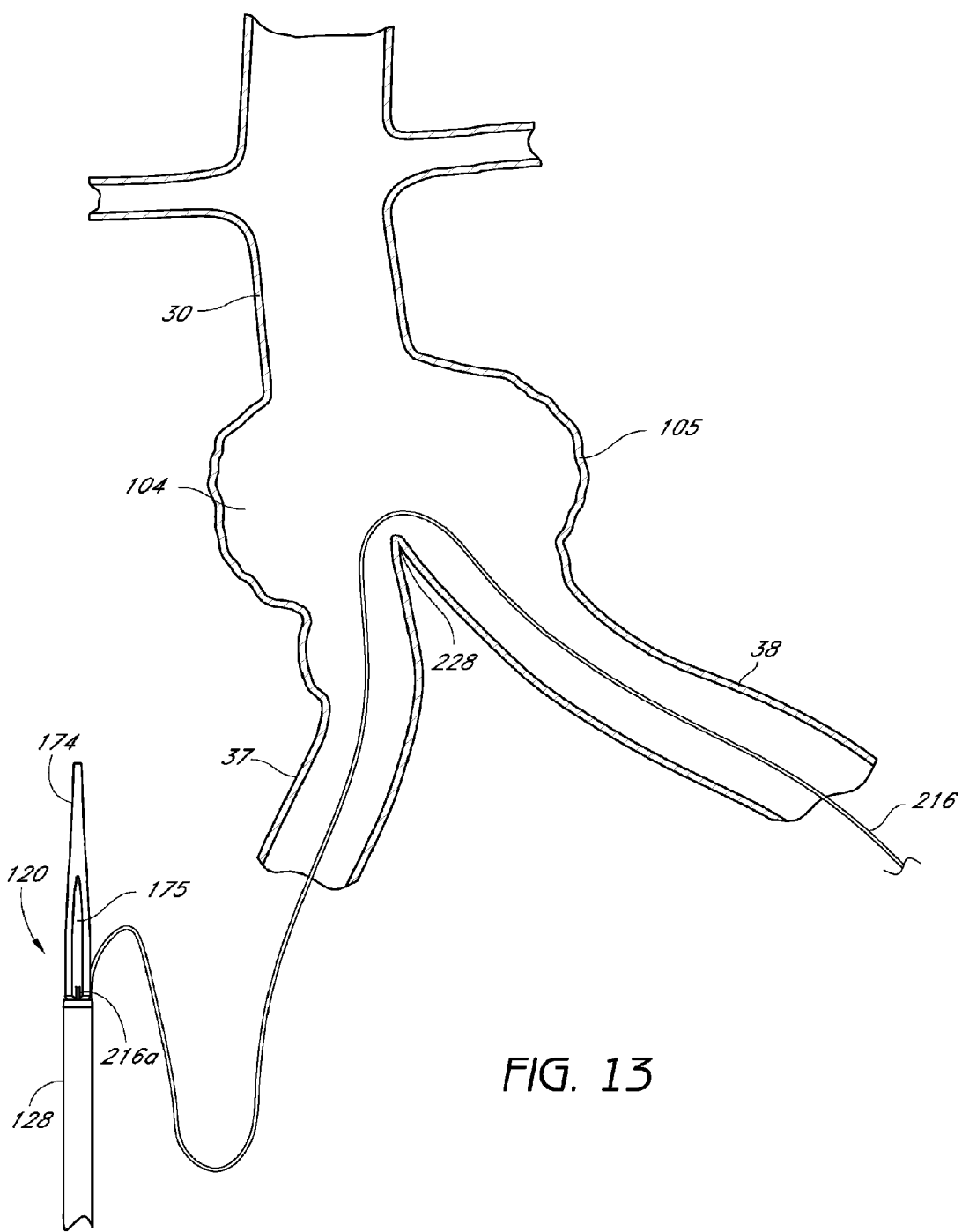
FIG. 13 is a schematic representation of an embodiment of the deployment catheter with the guidewire sheath positioned across the bifurcation.

With reference to the embodiments of the deployment catheter 120 described above, an exemplary procedure or method of using the deployment catheter 120 to treat a patient's abdominal aortic aneurysm using the embodiments of the bifurcated endoluminal graft 178 disclosed above will now be described. FIG. 13 is a schematic representation of an embodiment of the deployment catheter 120 with the guidewire sheath 216 positioned across the bifurcation and within the contralateral iliac artery. The hollow guidewire sheath 216 is preferably introduced into the ipsilateral iliac artery through an ipsilateral access site in the femoral artery, advanced superiorly towards the aorta, and using cross-over techniques known to those skilled in the arts, subsequently advanced inferiorly down the contralateral iliac artery and out a contralateral access site in the contralateral femoral artery. As described above, the distal end 216a of the guidewire sheath 216 is preferably positioned within a groove or depression 175 formed in the distal tip 174 of the deployment catheter 120. Thus, the distal end portion 216a of the hollow guidewire sheath 216 is effectively attached to the deployment catheter 120 while the proximal end 216b of the hollow guidewire sheath extends from the contralateral access site.

Figure 14:
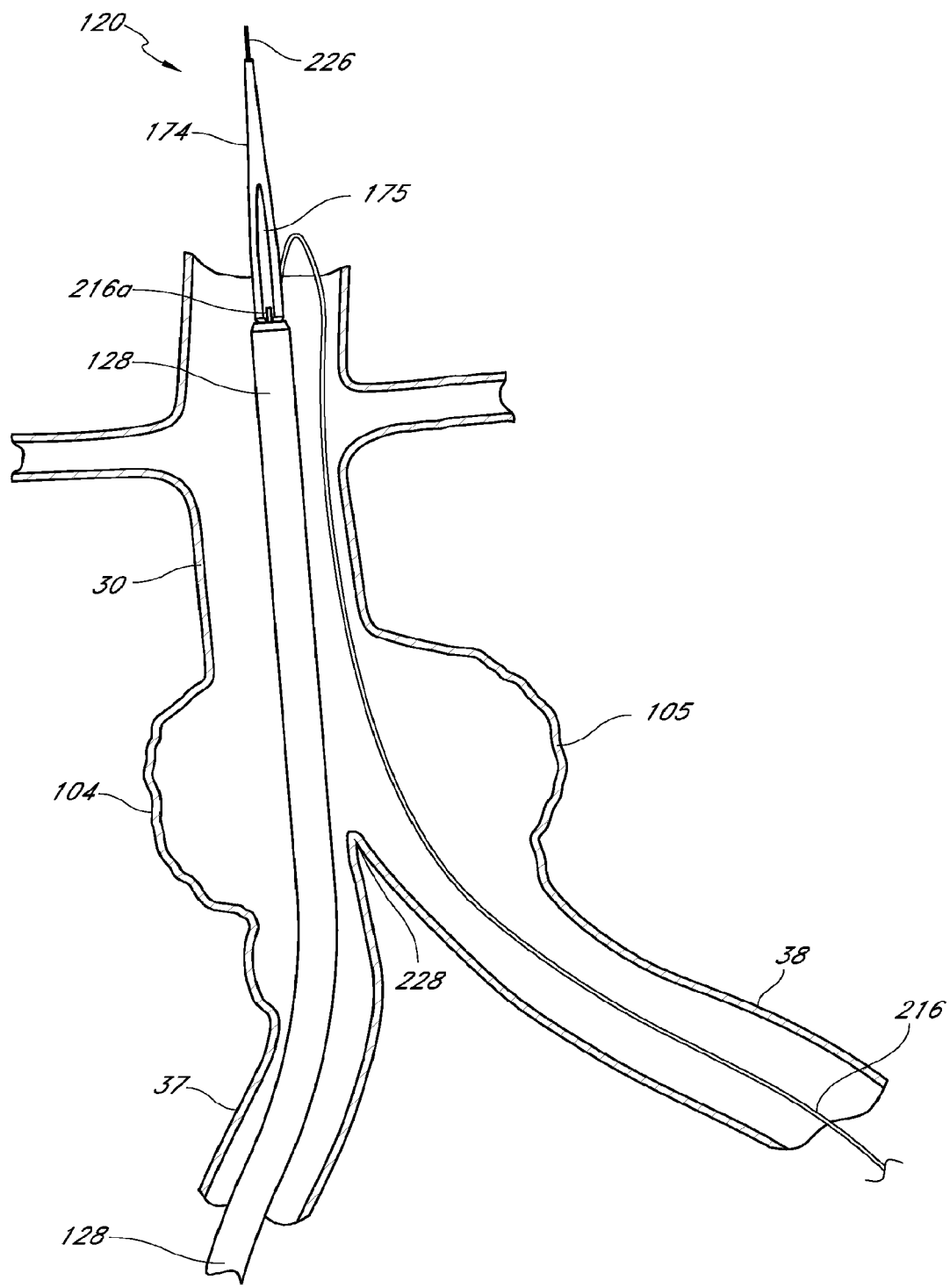
FIG. 14 is a schematic representation, as in FIG. 13, with the deployment catheter positioned in the aorta.

FIG. 14 is a schematic representation, as in FIG. 13, with the deployment catheter positioned in the aorta. Referring to FIG. 14, after the guidewire assembly 214 the has been positioned across the bifurcation in the aorta, the deployment catheter 120 is then preferably advanced over a second guidewire 226, such as but not limited to a standard 0.035 in. guidewire, from the ipsilateral access site into the aorta using techniques known to those skilled in the arts. Traction is preferably applied to the hollow guidewire sheath 216 from the contralateral access site to take up the slack in the hollow guidewire sheath 216 as the deployment catheter 120 is advanced into the aorta.

At this point, an inner core wire 218 (not shown) may be advanced through the hollow guidewire sheath 216, depending on the desires of the medical practitioner. As is illustrated, the hollow guidewire sheath 216 has preferably been positioned across the bifurcation and the deployment catheter 120 has been advanced into the aorta over a second guidewire 226 without the inner core wire being positioned in the hollow guidewire sheath 216. Once the deployment catheter 120 is positioned within the patient's aorta, an inner core wire 270 can be advanced superiorly from the contralateral access site through the central lumen 220 of the hollow guidewire sheath 216. In the illustrated embodiment, the inner core wire 270 can be advanced beyond the distal end 216a of the guidewire sheath 216 such that the inner core wire 270 can extend beyond the outer sheath 128 of the deployment catheter 120.

FIG. 15 is a schematic representation, as in FIG. 14, with the compressed ipsilateral and contralateral branch portions 182, 184 of the bifurcated endoluminal graft 178 positioned partly within the ipsilateral and contralateral iliac arteries, respectively. The ipsilateral and contralateral branch portions 182, 184 of the bifurcated graft 178 may be exposed as is illustrated in FIG. 15 by proximally retracting the outer sheath 128 of the deployment catheter 120 while holding the inner core 132 and, hence, the distal tip 174, in the same approximate axial location. As mentioned above, in the illustrated embodiment, in the compressed state, the bifurcated graft 178 is preferably compressed around the torsion tab 196 that is preferably rigidly attached to the central tube 170. In this arrangement, after the contralateral branch portion 184 has been exposed by retracting the outer sheath 128, the bifurcated graft 178 can be rotated so that the contralateral branch portion 184 is correctly positioned in the patient's anatomy by rotating the proximal end of the inner core 132 or the "Y" connector 169 which, in turn, rotates the central tube 170 and torsion tab 196.

Additionally, because the guidewire sheath 216 preferably forms a half loop within the outer sheath 128 so as to protrude out of the distal end of the outer sheath 128, as the outer sheath 128 is being proximally retracted relative to the inner core 132, traction can be applied to the guidewire sheath 216 from the contralateral access site to take up the slack in the guidewire sheath 216 as the outer sheath 128 is being proximally retracted relative to the inner core 132. Slightly proximally retracting the deployment catheter 120 and, if desired, the guidewire sheath 216, will preferably position the bifurcated graft 178 as illustrated in FIG. 15. The bifurcated graft 178 is preferably configured so that the contralateral branch portion 184 separates or rotates away from the ipsilateral branch portion 182, as shown in FIG. 15, as the outer sheath 128 is proximally retracted.

Alternatively, the ipsilateral and contralateral branch portions 182, 184 of the bifurcated graft 178 can be exposed and positioned as is illustrated in FIG. 15 by advancing the deployment catheter 120 (i.e., advancing the inner core 132 and outer sheath 128 together) up the ipsilateral iliac artery toward the aorta. At the point where the distal end of the outer sheath 128 has extended slightly axially beyond the bifurcation of the aorta 228, the medical practitioner can then axially advance the inner core 132 relative to the outer sheath 128 (i.e., by holding the outer sheath 128 stationary) until the ipsilateral and contralateral branch portions 182, 184 of the bifurcated graft 178 have been fully exposed or deployed. Because the distal end of the outer sheath 128 has preferably been held in position slightly beyond the bifurcation of the aorta 228, the ipsilateral and contralateral branch portions 182, 184 of the graft 178 will preferably be substantially completely above the bifurcation of the aorta 228. Slightly proximally retracting the deployment catheter 120 and, if desired, the guidewire sheath 216, will preferably position the bifurcated graft 178 as illustrated in FIG. 15.

Figure 16:
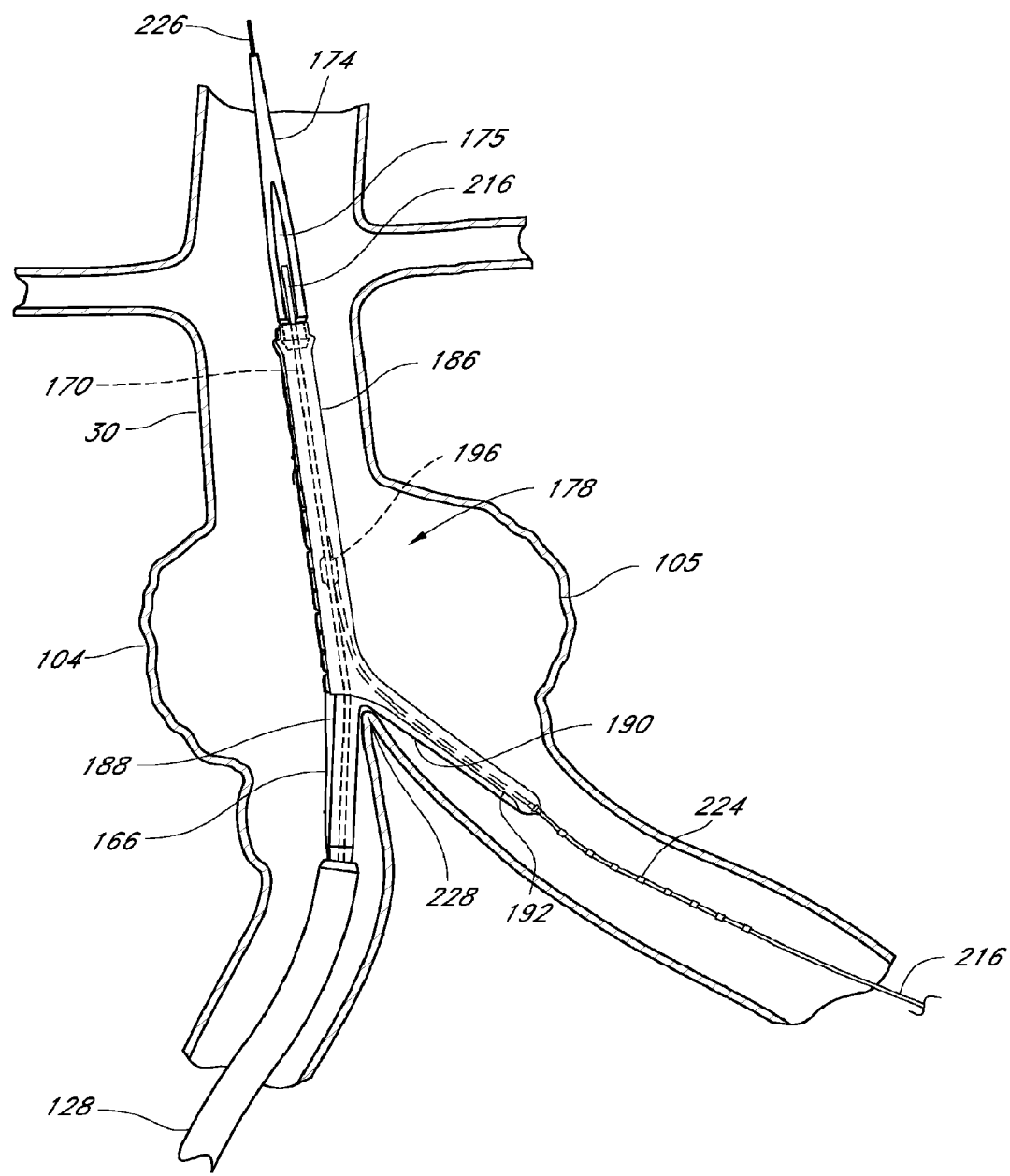
FIG. 16 is a schematic representation, as in FIG. 14, with the compressed iliac branches of the graft positioned substantially entirely within the iliac arteries.

FIG. 16 is a schematic representation, as in FIG. 14, with the compressed ipsilateral and contralateral branch portions 182, 184 of the graft 178 positioned substantially fully within the respective ipsilateral and contralateral iliac arteries. As shown in FIG. 16, the bifurcated graft 178 is preferably configured so as to abut against the bifurcation of the aorta 228 or be positioned in the vicinity of the bifurcation of the aorta 228 by retracting the deployment catheter 120 and, if desired, the guidewire sheath 216 until the bifurcated graft 178 abuts or is in the vicinity of bifurcation of the aorta 228.

Figure 17:
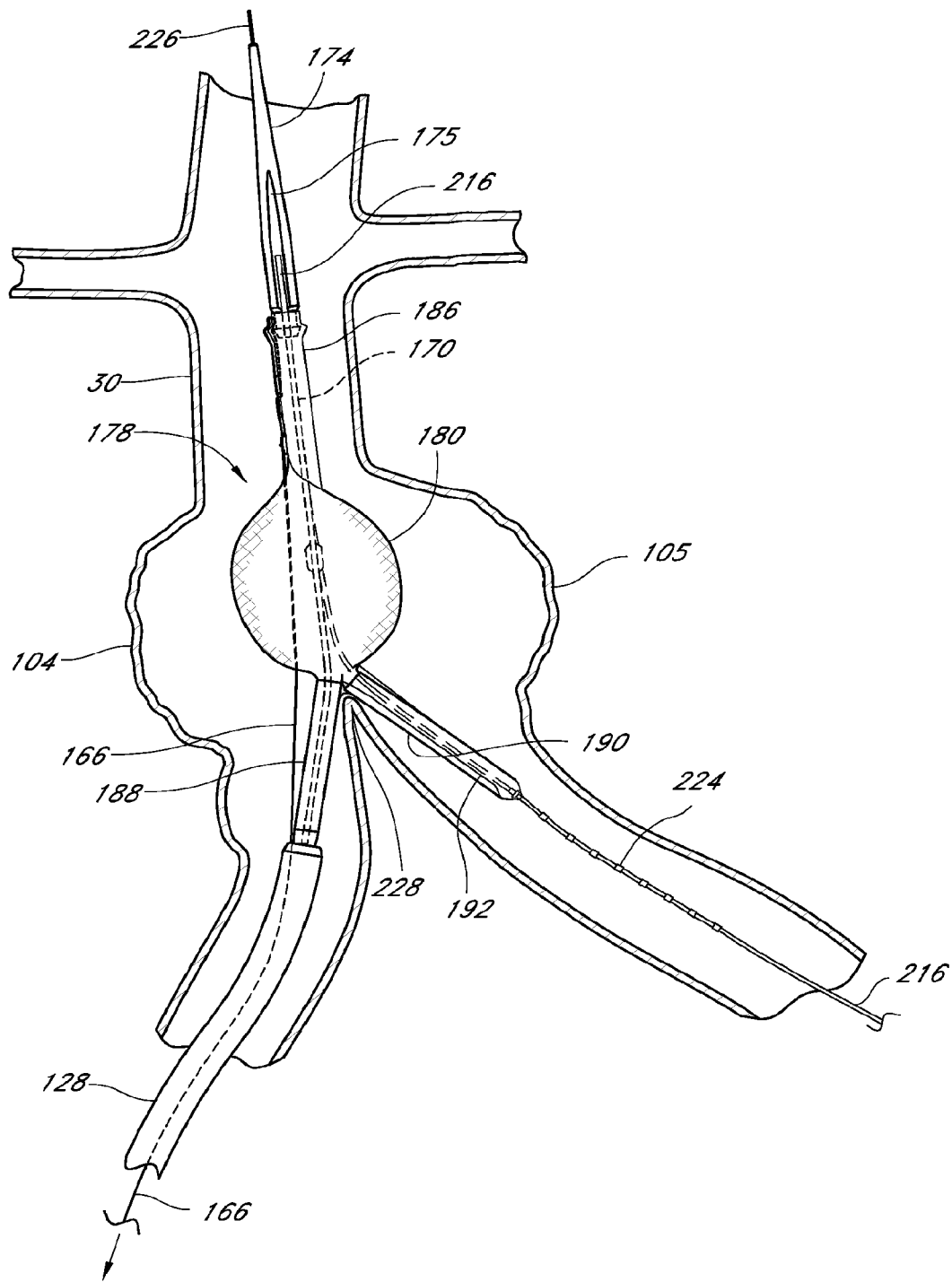
FIG. 17 is a schematic representation, as in FIG. 16, with a proximal portion of the main branch portion of the graft at least partially deployed within the aorta.

FIG. 17 is a schematic representation, as in FIG. 16, with a proximal portion of the main branch portion 180 of the graft 178 or at least partially deployed within the aorta. The proximal portion of the main branch portion 180 of the graft 178 is preferably partially deployed within the aorta as illustrated by proximally retracting the sheath release wire 166, as described above, while preferably holding the inner core 132 in a fixed position relative to the aorta so as to prevent exerting undue force on the bifurcation of the aorta 228 or other portions of the anatomy. Deploying the graft 178 in a bottom up sequence, as illustrated herein, may help mitigate the "wind socking" effect that can cause proximal migration of the graft 178. Additionally, deploying the graft 178 and a bottom up sequence may allow for either axially or rotationally repositioning of a partially deployed graft 178 without causing significant or any damage to the arterial wall. In some embodiments, this may partly be due to the fact that the deployed middle portion of the graft 178 may move against the arterial wall more easily than a deployed end portion of the graft 178.

Figure 18:
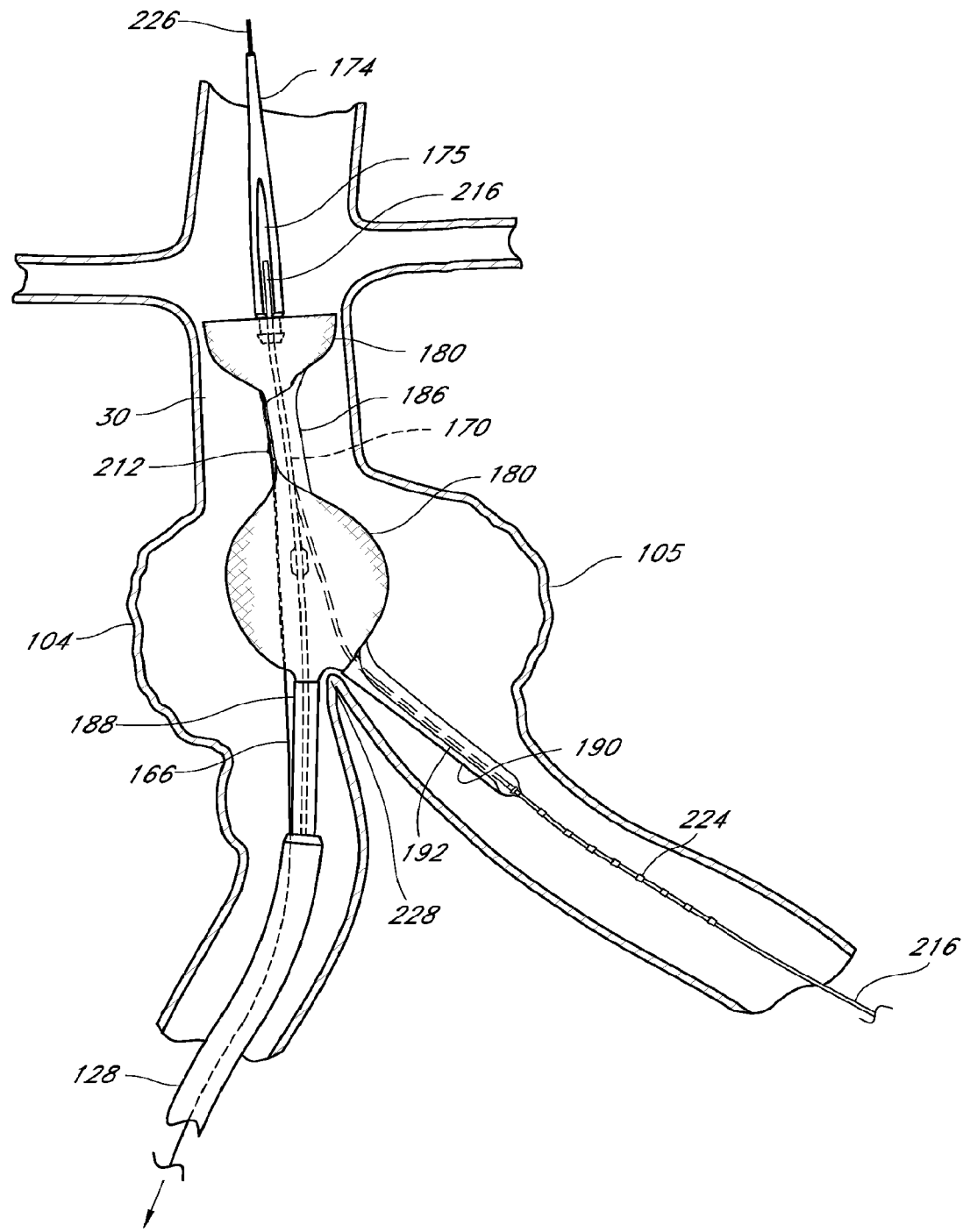
FIG. 18 is a schematic representation, as in FIG. 17, with a proximal portion and a distal portion of the main branch portion of the graft partially deployed within the aorta.

FIG. 18 is a schematic representation, as in FIG. 17, with a proximal portion and a distal portion of the main branch portion 180 of the graft 178 partially deployed within the aorta. The distal portion of the main branch portion 180 of the graft 178 is preferably partially deployed within the aorta as illustrated by further proximally retracting the sheath release wire 166, as described above, while still preferably holding the inner core 132 in a fixed position relative to the aorta so as to prevent exerting undue force on the bifurcation of the aorta 228 or other portions of the anatomy.

Figure 19:
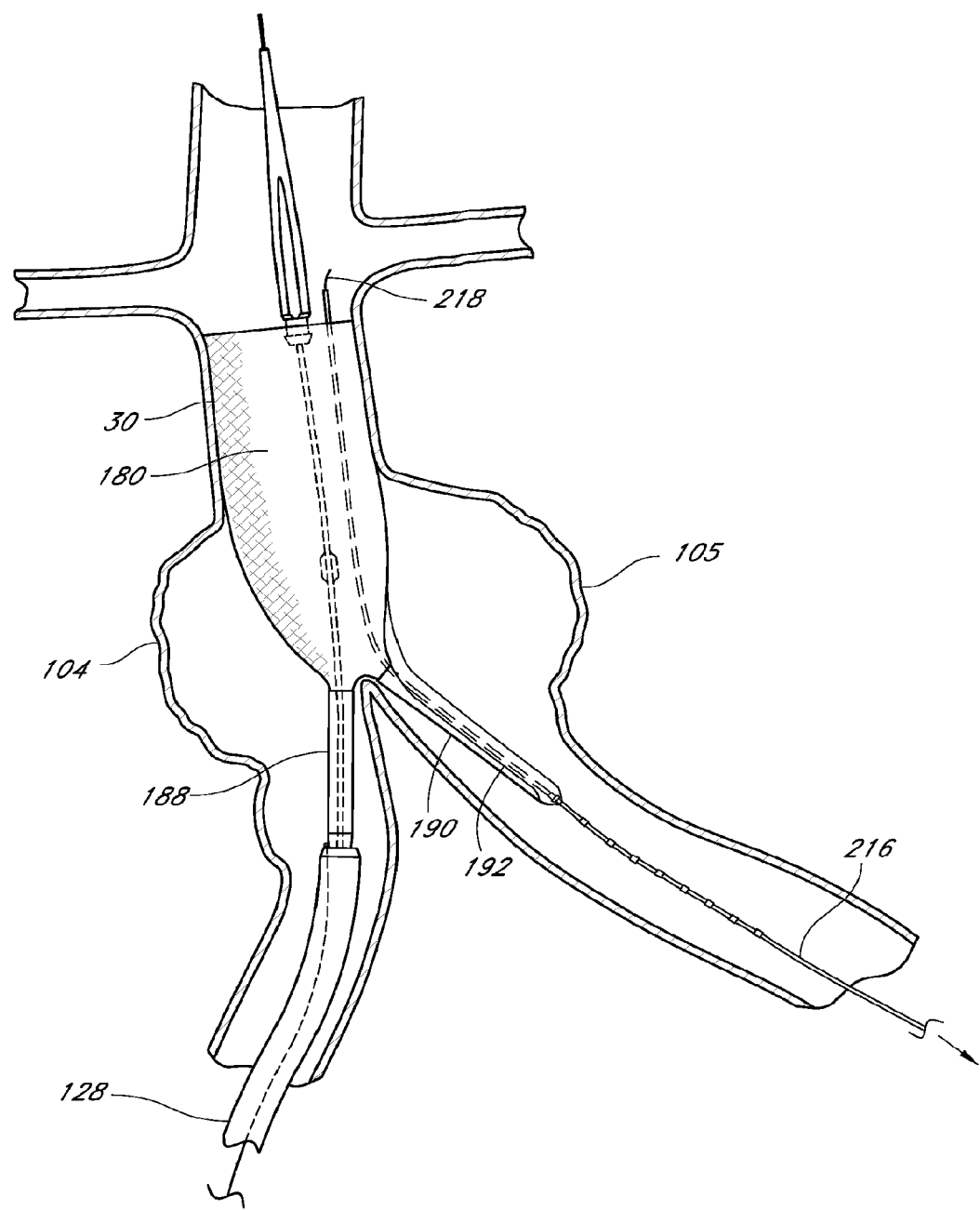
FIG. 19 is a schematic representation, as in FIG. 17, following deployment of substantially the entire length of the main branch portion of the graft within the aorta.

FIG. 19 is a schematic representation, as in FIG. 18, following deployment of substantially the entire length of the main branch portion 180 of the graft 178 within the aorta. The remaining constrained portion of the main branch portion 180 of the graft 178 is preferably deployed within the aorta as illustrated by further proximally retracting the sheath release wire 166, as described above, while still preferably holding the inner core 132 in a fixed position relative to the aorta so as to prevent exerting undue force on the bifurcation of the aorta 228 or other portions of the anatomy.

Because the distal end the hollow guidewire sheath 216 extends beyond the distal end of the main branch portion 180, an inner core wire 218 can now be advanced through the guidewire sheath 216 so that the tip of the inner core wire 218 will not catch on the endoskeleton or wireframe of the expanded main branch portion 180 as the inner core wire 218 as it is advanced distally through the lumen of the main branch portion 180. The inner core wire 218 may be advanced through the distal end of the hollow guidewire sheath 216 such that, when the hollow guidewire sheath 216 is withdrawn, the inner core wire 218 will preferably remain positioned through the central lumen of the expanded main branch portion 180 of the bifurcated graft 178 to provide subsequent access to the main graft 178 as well as superiorly within the patient's aorta. In some embodiments, the inner core wire 218 preferably has a length at least twice as long as that of the guidewire sheath 216, such that physical contact can be maintained with the inner core wire 218 while the hollow guidewire sheath 216 is being withdrawn over the inner core wire 218. In this configuration, potential friction between the inner core wire 218 and the hollow guidewire sheath 216 is preferably prevented from inadvertently withdrawing the inner core wire 218 as the guidewire sheath 216 is withdrawn. Note that the inner core wire 218 could also have been advanced distally through the lumen of the guidewire sheath 216 during any of the previous steps described above.

As such, FIGS. 17-19 illustrate an embodiment of the main branch sheath 186 in which the main branch portion 180 of the graft 178 is initially deployed in a bottom-up sequence and then in a top-down sequence. However, the embodiments of the main branch sheath 186 and the deployment catheter 120 are not so limited. The main branch sheath 186 and the deployment catheter 120 can be configured to deploy the main branch portion 180 of the bifurcated graft 178 in any desired or suitable sequence to address different clinical situations or needs, such as, but not limited to, a top down sequence. For example, for a thoracic aneurysm, it may be beneficial to configure the main branch sheath 186 so that the main branch portion 180 deploys in a bottom-up sequence. Additionally, as mentioned above, for some clinical situations, deploying the main branch portion 180 of the graft 178 as described above may be beneficial because it may mitigate a "wind socking" or "sailing" effect and also preferably prevent the knot 212 from becoming caught on the distal edge or distal portion of the main branch portion 180 of the bifurcated graft 178 or between the distal portion of the main branch portion 180 and the wall of the aorta after the main branch portion 180 of the bifurcated graft 178 has been deployed.

Figure 20:
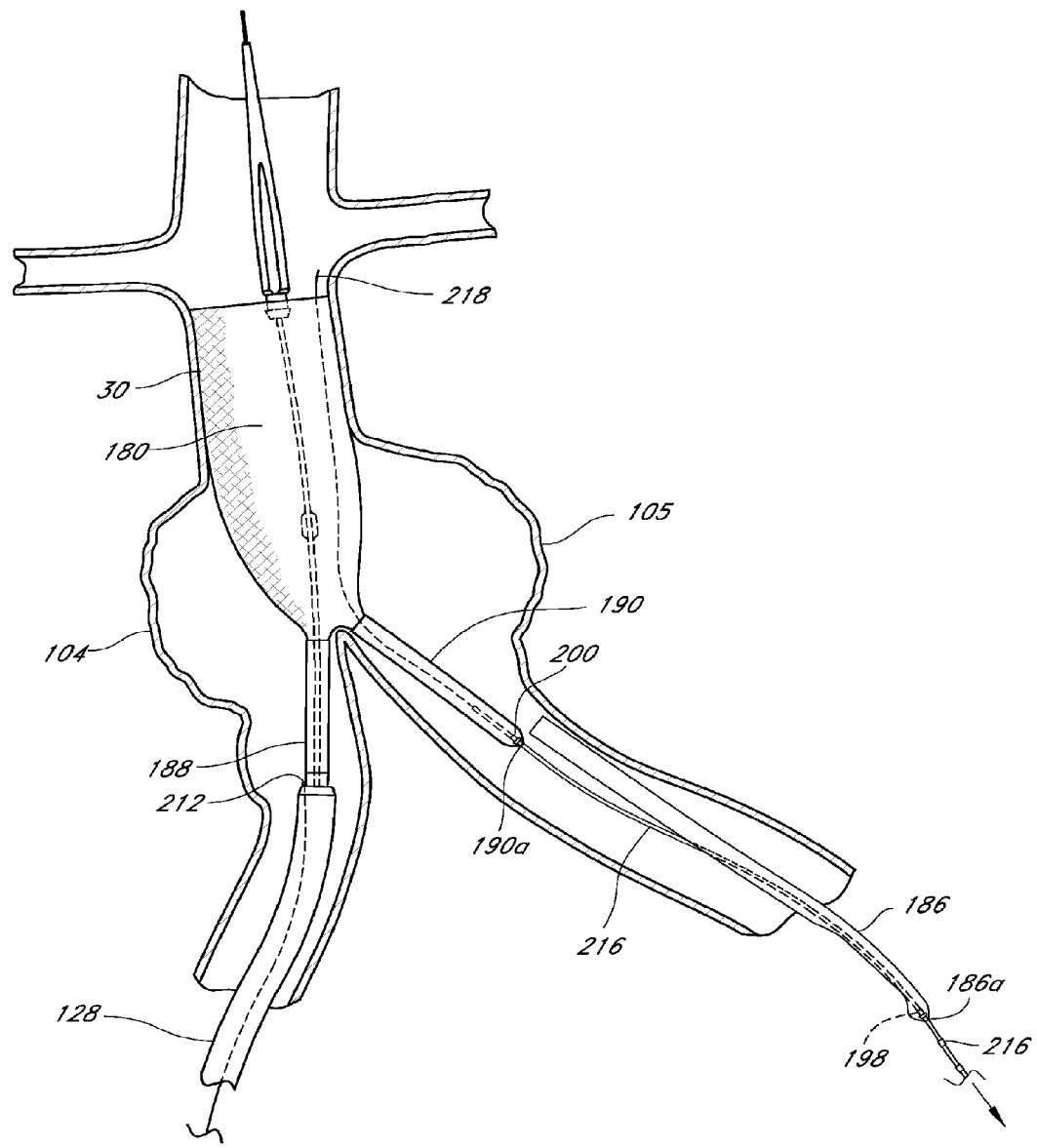
FIG. 20 is a schematic representation, as in FIG. 19, following the partial retraction of the guidewire sheath and the main graft sheath through the contralateral iliac artery.

FIG. 20 is a schematic representation, as in FIG. 19, following the partial retraction of the guidewire sheath 216 and the main graft sheath 186 through the contralateral iliac artery. Note that, as illustrated in FIG. 20, the main graft sheath 186 has preferably been split apart as described above so that a tear has been propataged along substantially the entire length of one side the main graft sheath 186. As the guidewire sheath 216 is preferably proximally retracted through the contralateral artery, once the main branch tab 198 abuts the proximal end 186a of the main branch sheath 186, further proximal retraction of the guidewire sheath 216 will preferably also retract the main graft sheath 186. Withdrawing the main graft sheath 186 through the contralateral iliac artery, when the deployment catheter 120 has been routed through the ipsilateral iliac artery as shown prevents any interference between the main graft sheath 186 and the outer sheath 128 or other components of the deployment catheter 120 as the main graft sheath 186 is being withdrawn.

In the illustrated embodiment, the main graft tab 198 is preferably positioned on the guidewire sheath at a sufficient axial distance away from the contralateral branch tab 200 such that the main branch sheath 186 will preferably be substantially retracted past the contralateral branch sheath 190 before the contralateral branch portion 184 is deployed. As illustrated in FIG. 20, the guidewire sheath 216 has preferably been proximally retracted to the point where the contralateral branch tab 200 has first abutted the proximal end 190a of the contralateral branch sheath 190.

Figure 21:
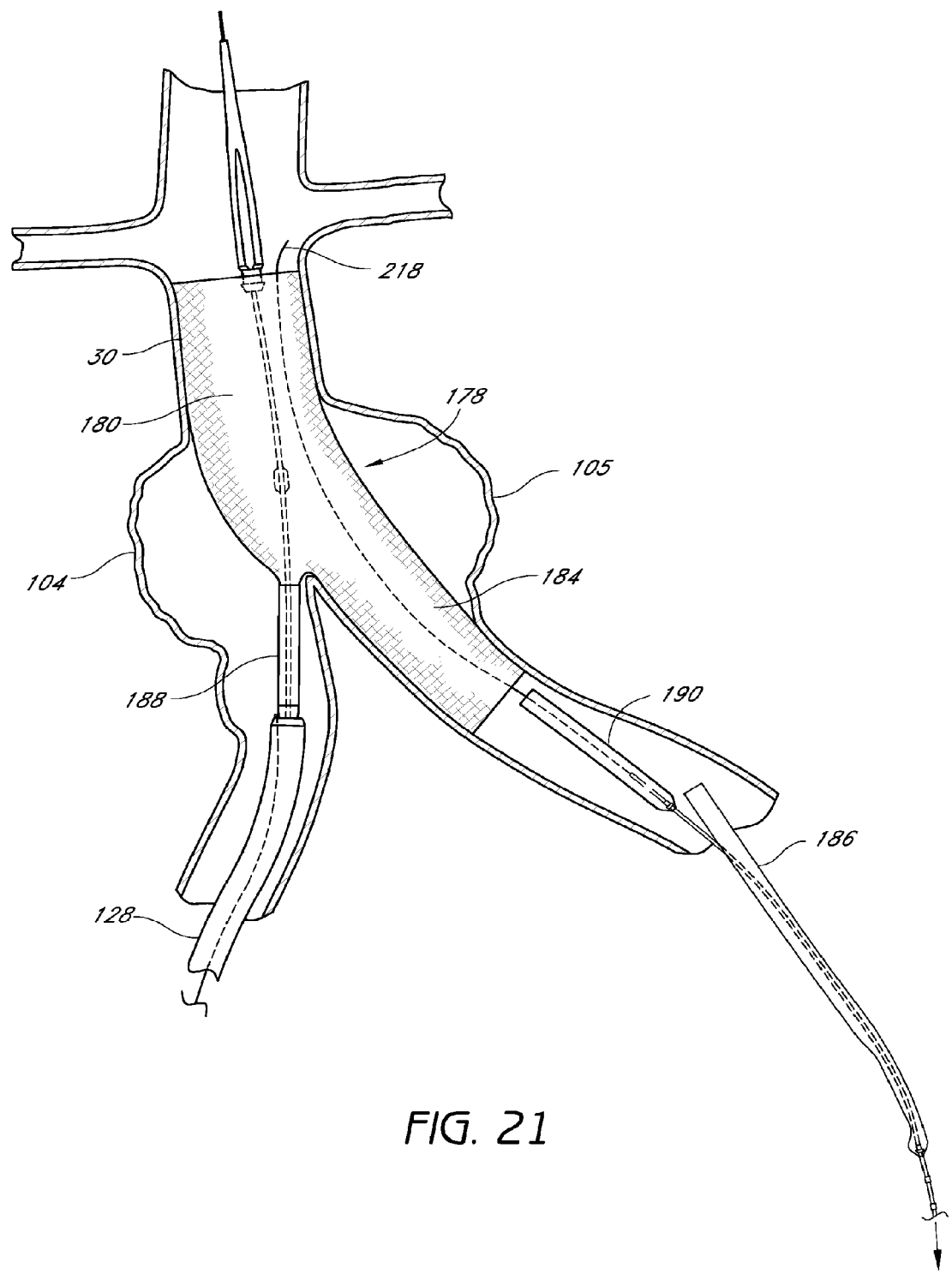
FIG. 21 is a schematic representation, as in FIG. 20, following the further proximal retraction of the guidewire sheath and the contralateral branch sheath through the contralateral iliac artery, causing the deployment of the contralateral branch portion of the graft.

FIG. 21 is a schematic representation, as in FIG. 20, following the further proximal retraction of the guidewire sheath 216 and, consequently, the contralateral branch sheath 190, through the contralateral iliac artery. As illustrated therein, the contralateral branch sheath 190 has been retracted so as to completely deploy the contralateral branch portion 184 of the bifurcated graft 178. If desired, the inner core wire 218 can be manipulated as described above so as to remain in the position illustrated in FIG. 21. The main branch sheath 186 and the contralateral branch sheath 190 can be then withdrawn from the patient through the contralateral access site. Accordingly, in the illustrated embodiment the main branch sheath 186 and the contralateral branch sheath 190 are introduced into the patient through the ipsilateral access site and then removed from the patient through the contralateral access site. In modified embodiments configured for other portions of the patient's anatomy, the main branch sheath 186 and the contralateral branch sheath 190 are introduced through a first vessel and then removed from the patient though a second vessel.

Figure 22:
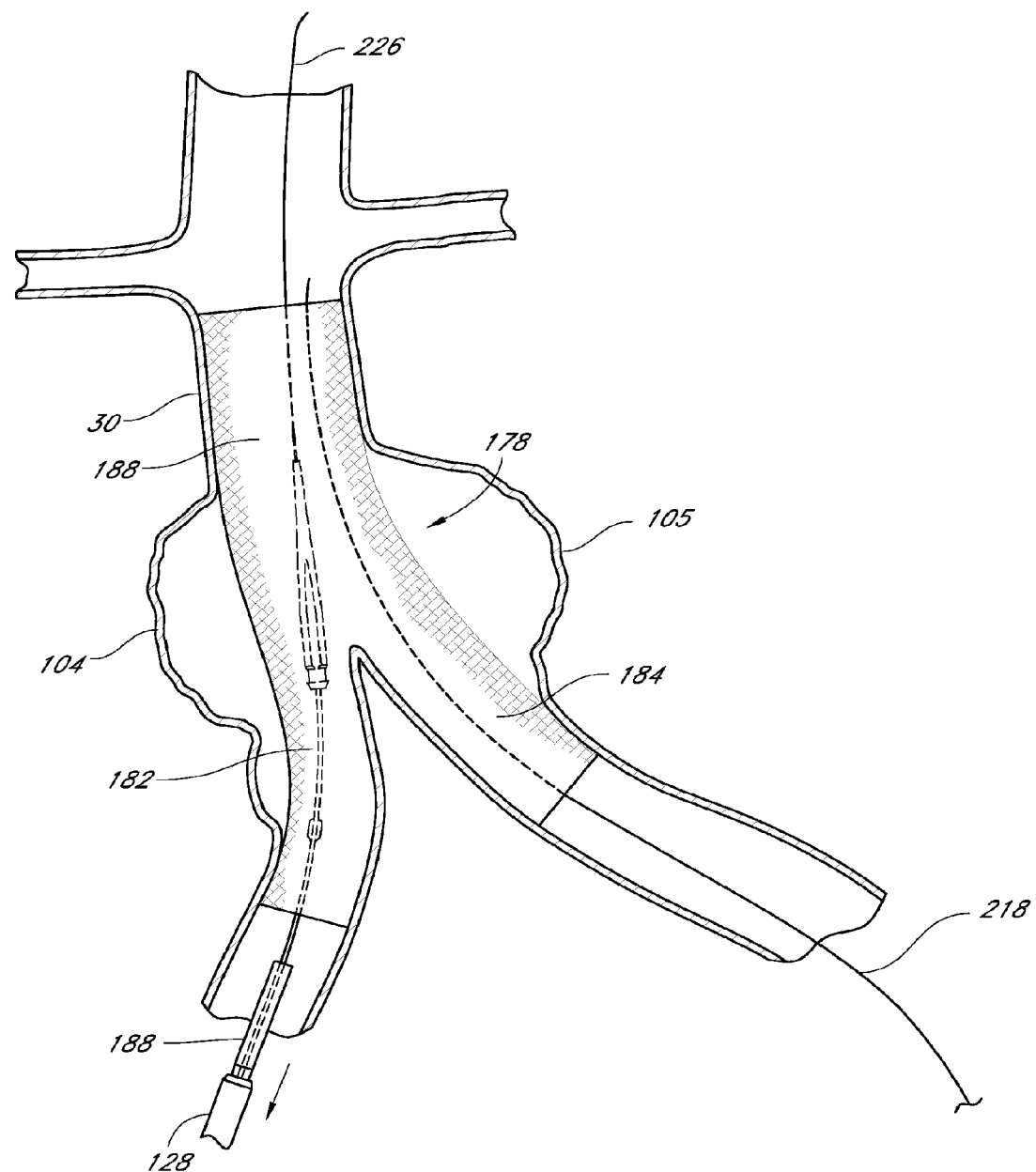
FIG. 22 is a schematic representation, as in FIG. 21, following the proximal retraction of the ipsilateral branch sheath and deployment of the ipsilateral branch portion of the graft.

FIG. 22 is a schematic representation, as in FIG. 21, following the proximal retraction of the ipsilateral branch sheath 188 and deployment of the ipsilateral branch portion 182 of the graft 178. The ipsilateral branch portion 182 of the graft 178 may be deployed by proximally retracting the inner core 132 which, as described above, is preferably directly or indirectly rigidly attached to the ipsilateral branch sheath 188. Because the ipsilateral branch sheath 28 is preferably an open-ended tubular sheath, the ipsilateral branch portion 182 of the graft 178 is preferably deployed in a top down sequence.

However, the ipsilateral branch sheath 188 (and the contralateral branch sheath 190) can be configured to accommodate any other desired or suitable sequence. For example, in some embodiments, the ipsilateral branch sheath 188 (and the contralateral branch sheath 190) can be configured to be a perforated sheath similar to the main branch sheath 186 described above, wherein a sheath release wire could be routed through the perforations to deploy each of the branch sheaths 188, 190 in either a top-down, a bottom-up, or in any other desired direction or combination thereof. Also, note that the ipsilateral guidewire 226 can be retracted simultaneously with the deployment catheter 120, or can be retracted at any time preferably after the deployment catheter 120 has been positioned in the desired location within the aorta.

Figure 23:
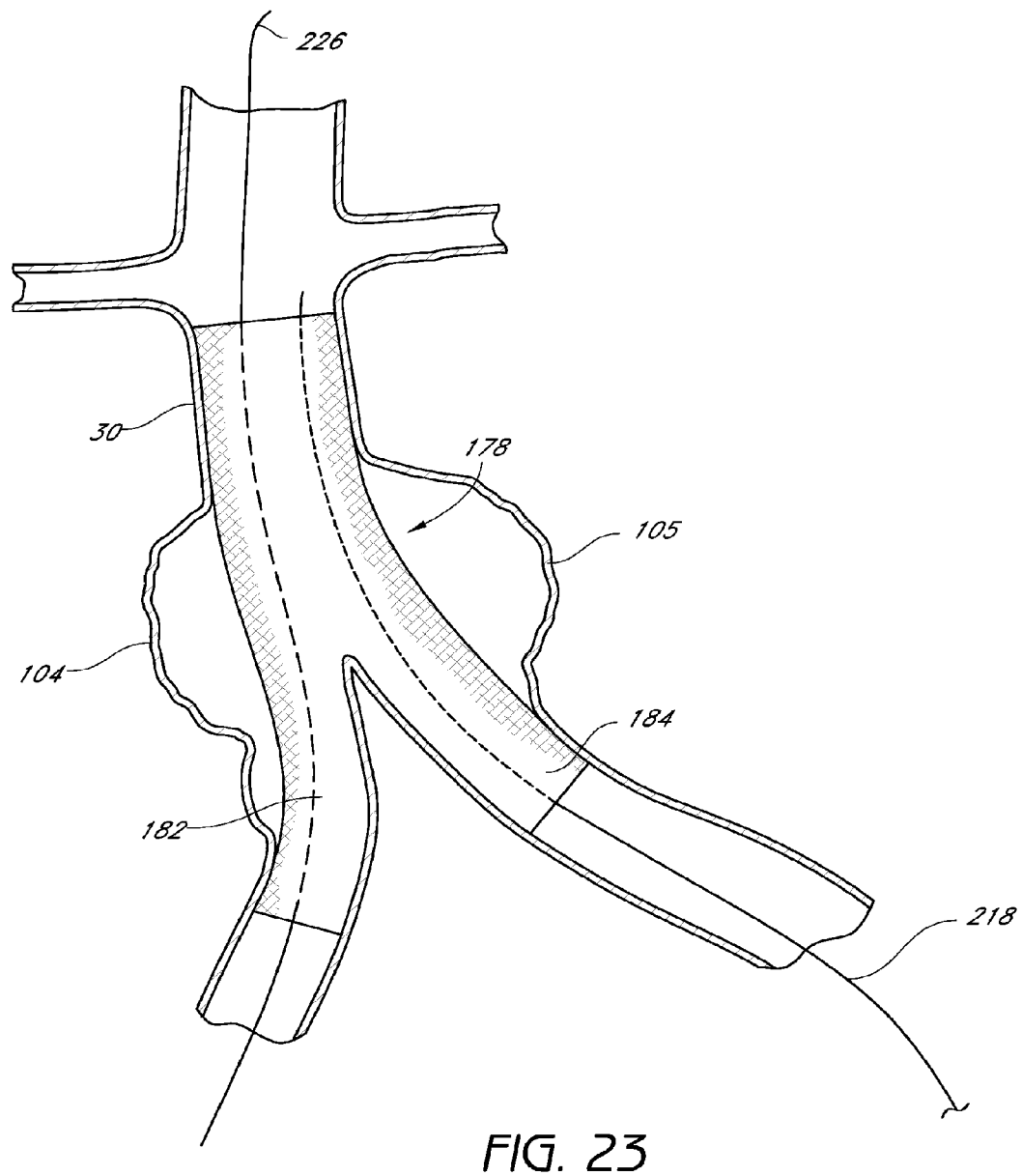
FIG. 23 is a schematic representation, as in FIG. 22, of the deployed bifurcated graft with the inner core wire positioned within the main branch portion of the deployed graft.

FIG. 23 is a schematic representation, as in FIG. 22, of the deployed bifurcated graft 178 with the inner core wire 218 positioned within the main branch portion of the deployed graft. As shown in FIG. 23, the inner core wire 218 can remain positioned in the patient's aorta, providing continued access to the graft and the aorta through the contralateral iliac artery. Thus, any variety of diagnostic and/or therapeutic procedures may be accomplished following the implantation of the bifurcated graft and that require guidance can use the inner core wire 218. For example, the inner core wire 218 may be used to guide a balloon dilation catheter to the graft site to dilate a stenosis, re-expand a portion of the graft or perform other touch up procedures. Alternatively, the inner core wire may be used to guide a subsequent catheter to the graft location for deploying a cuff either in the aorta, for example at the distal end of the main graft segment, or alternatively in the iliac artery at the proximal end of one of the branch graft portions. In addition or in the alternative, those of skill in the art will recognize that a variety of other therapeutic and/or diagnostic catheters or instruments that require guidance can also utilize the inner core wire 218.

For certain post-implantation procedures, the catheters, such as the dilation catheter or cuff deployment catheter described above, may be configured to be advanced over a smaller diameter, more flexible wire such as the inner core wire 218. However, for certain devices, the smaller diameter of the inner core wire may not provide enough strength or stability to guide the catheter to the treatment site. For example, many catheters are currently designed to be delivered over a 0.035 in. guidewire, and thus an inner core wire which has a diameter of approximately 0.014 in. may not provide enough stability over which to guide the catheter.

In such cases, an exchange catheter having an inner diameter greater than the diameter of the desired guidewire may be advanced through the contralateral access site over the inner core wire 218. Once the exchange catheter has been advanced to the distal end of the inner core wire 218, the inner core wire 218 may be proximally retracted through the contralateral access site. A larger guidewire, such as a 0.035 in. guidewire may then be advanced through the exchange catheter to the main branch portion. Once the larger guidewire has been advanced through the exchange catheter, the exchange catheter may be proximally withdrawn from the contralateral access site, leaving the larger diameter guidewire in position in the patient's contralateral iliac and extending through the main branch portion. Thus, the smaller diameter inner core wire may be exchanged for a larger diameter guidewire more suitable for use with larger instrument catheters without encountering any of the complications associated with trying to advance a guidewire having a curved distal tip through a deployed graft portion.

The exchange catheter may comprise an elongate flexible tubular body having a single lumen with an inside diameter of at least approximately 0.003 in. greater than the outer diameter of the desired procedure guidewire. The body may include a helical coil, braid, or weave within the tubular wall, to resist kinking, as is understood in the art. A proximal hub may be provided on the tubular body, to facilitate grasping and removal of the exchange catheter following placement of the desired procedure guidewire.

While the above description has shown, described, and pointed out novel features as applied to various embodiments, it will be understood that various omissions, substitutions, and changes in the form and details of the device or process illustrated may be made without departing from the spirit of the disclosure. Additionally, the various features and processes described above may be used independently of one another, or may be combined in various ways. All possible combinations and subcombinations are intended to fall within the scope of this disclosure.

As will be recognized, certain embodiments described herein may be embodied within a form that does not provide all of the features and benefits set forth herein, as some features may be used or practiced separately from others. The scope of the inventions is indicated by the appended claims rather than by the foregoing description. All changes which come within the meaning and range of equivalency of the claims are to be embraced within their scope.

For example, while the delivery system is described with respect to deploying a bifurcated stent in the abdominal aortic and leaving a guidewire positioned through the expanded stent, it is further envisioned that the delivery system could be used to deliver a prosthesis having a main portion and at least one branch portion, or alternatively a prosthesis having only a straight, main branch portion, to other branched intravascular vessels (e.g., the thoracic aorta and a cardiac artery) and leave a guidewire positioned through the expanded prosthesis.

What is claimed is:

1. A method of deploying a bifurcated prosthesis in a patient's vasculature, comprising:

supporting the bifurcated prosthesis with a deployment catheter;

advancing at least a distal end portion of the deployment catheter and the prosthesis through a first access site in a first vessel in the patient's vasculature to a bifurcation region of the patient's vasculature;

positioning a main body portion of the bifurcated prosthesis in a main vessel;

positioning a first branch portion of the bifurcated prosthesis in a first branch vessel, a diameter of the first branch portion being smaller than a diameter of the main body portion;

positioning a second branch portion of the bifurcated prosthesis in a second branch vessel, wherein the first and second branch vessels branch off the main vessel, a diameter of the second branch portion being smaller than the diameter of the main body portion;

releasing a main body portion of the bifurcated prosthesis from a main body restraint so that the main body portion of the bifurcated prosthesis expands in the main vessel; and withdrawing the main body restraint from the patient's vasculature through a second access site in a second vessel, wherein the second access site is at a different location than the first access site.

2. The method of claim 1, comprising advancing the main body restraint into the patient's vasculature through the first access site.

3. The method of claim 1, comprising releasably restraining the first branch portion of the prosthesis with a first branch restraint and releasably restraining the second branch portion of the prosthesis with a second branch restraint.

4. The method of claim 3, comprising withdrawing the first branch restraint from the patient's vasculature through the first access site in the first branch vessel and withdrawing the second branch restraint from the patient's vasculature through the second access site in the second branch vessel.

5. The method of claim 1, wherein supporting the bifurcated prosthesis with the deployment catheter comprises supporting the bifurcated prosthesis on an outside surface of a portion of an inner core, the deployment catheter further comprising an outer sheath extending over at least a portion of the inner core and being axially advanceable relative to the inner core, the outer sheath being configured to surround the prosthesis until the outer sheath is proximally retracted.

6. The method of claim 1, comprising opening at least a portion of the main body restraint by retracting a release wire attached to the main body restraint.

7. The method of claim 1, further comprising opening at least a portion of the main body restraint by retracting a release wire configured to tear one or more portions of the main body restraint when the release wire is proximally retracted.

8. The method of claim 1, wherein withdrawing the main body restraint from the patient's vasculature through the second access site in the second vessel comprises retracting a retraction wire coupled with the main body restraint through the second access site.

9. The method of claim 8, wherein the retraction wire is a hollow retraction wire and wherein the method of deploying the bifurcated prosthesis in the patient's vasculature further comprises positioning an inner wire within the hollow retraction wire.

10. The method of claim 9, further comprising generally maintaining a position of the inner wire in the patient's vasculature while retracting the retraction wire.

11. The method of claim 1, comprising withdrawing a second branch restraint from the patient's vasculature through the second access site in the second vessel by retracting a retraction wire through the second access site, the retraction wire being configured to engage and withdraw the second branch restraint as the retraction wire is withdrawn.

12. The method of claim 1, wherein the first access site is an opening in one iliac artery, establishing it as the ipsilateral iliac artery, and the second access site is an opening in the contralateral iliac artery.

13. The method of claim 1, wherein the main vessel is the abdominal aorta, and wherein the first branch vessel and the second branch vessel are common iliac arteries.

14. A method of deploying a prosthesis in a patient's vasculature, comprising:
   supporting the prosthesis with a deployment catheter;
   advancing at least a distal end portion of the deployment catheter and the prosthesis through a first access site in a first vessel in the patient's vasculature to a target vessel of the patient's vasculature, a diameter of the first vessel being smaller than a diameter of the target vessel;
   releasing the prosthesis from a restraint so that at least a portion of the prosthesis self-expands in the target vessel; and
   withdrawing the restraint from the patient's vasculature through a second access site in a second vessel, wherein the second access site is at a different location than the first access site, a diameter of the second vessel being smaller than the diameter of the target vessel.

15. The method of claim 14, comprising advancing the restraint into the patient's vasculature through the first access site.

16. The method of claim 14, comprising releasably restraining a first branch portion of the prosthesis with a first branch restraint and releasably restraining a second branch portion of the prosthesis with a second branch restraint, the prosthesis being a branched or bifurcated prosthesis.

17. The method of claim 15, comprising withdrawing the second branch restraint from the patient's vasculature through the second access site in the second vessel.

18. The method of claim 14, comprising tearing open at least a portion of the restraint by retracting a release wire attached to or coupled with a portion of the restraint.

19. The method of claim 14, further comprising opening at least a portion of the restraint by retracting a release wire attached to the restraint through the first access site.

20. The method of claim 14, wherein withdrawing the restraint from the patient's vasculature through the second access site in the second vessel comprises retracting a retraction wire coupled with the restraint through the second access site and wherein the retraction wire is a hollow retraction wire and wherein the method of deploying the prosthesis in the patient's vasculature further comprises positioning an inner wire within the hollow retraction wire.

21. The method of claim 14, wherein the first access site is an opening in one iliac artery establishing it as the ipsilateral iliac artery, and the second access site is an opening in the contralateral iliac artery.

22. The method of claim 14, wherein the main vessel is the abdominal aorta, and wherein the first vessel and the second vessel are common iliac arteries.

* * * * *

UNITED STATES PATENT AND TRADEMARK OFFICE
CERTIFICATE OF CORRECTION

PATENT NO. : 8,764,812 B2  
APPLICATION NO. : 13/745682  
DATED : July 1, 2014  
INVENTOR(S) : Mayberry et al.

Page 1 of 1

It is certified that error appears in the above-identified patent and that said Letters Patent is hereby corrected as shown below:

In the Specification

In column 21 at line 40, After "the" delete "aft".

In column 23 at line 55, Before "end" delete "distal".

In the Claims

In column 34 at line 6, In Claim 17, change "15," to --16,--.

Signed and Sealed this
Twenty-fourth Day of March, 2015

Michelle K. Lee
*Director of the United States Patent and Trademark Office*